(12) United States Patent
Southern et al.

(10) Patent No.: US 8,372,629 B2
(45) Date of Patent: Feb. 12, 2013

(54) DEVICES AND PROCESSES FOR ANALYSING INDIVIDUAL CELLS

(75) Inventors: Edwin Southern, Oxford (GB); Wouter Meuleman, Oxford (GB); Dietrich Wilhelm Karl Lueerssen, Oxford (GB); Natalie Milner, Oxford (GB)

(73) Assignee: Oxford Gene Technology IP Limited, Oxford (GB)

( * ) Notice: Subject to any disclaimer, the term of this patent is extended or adjusted under 35 U.S.C. 154(b) by 547 days.

(21) Appl. No.: 11/919,761

(22) PCT Filed: May 3, 2006

(86) PCT No.: PCT/GB2006/001593
§ 371 (c)(1),
(2), (4) Date: Feb. 20, 2008

(87) PCT Pub. No.: WO2006/117541
PCT Pub. Date: Nov. 9, 2006

(65) Prior Publication Data
US 2009/0098541 A1    Apr. 16, 2009

(30) Foreign Application Priority Data
May 3, 2005  (GB) ................... 0508983.4

(51) Int. Cl.
*C12M 3/00*   (2006.01)
*C12M 1/00*   (2006.01)
*C12M 1/22*   (2006.01)

(52) U.S. Cl. ............. 435/288.3; 435/288.5; 435/287.1; 435/287.2; 435/287.3; 435/305.1; 435/287.9

(58) Field of Classification Search ............. 435/288.5, 435/288.7, 287.1, 287.2, 287.3, 288.3, 305.1, 435/287.9
See application file for complete search history.

(56) References Cited

U.S. PATENT DOCUMENTS
(Continued)

FOREIGN PATENT DOCUMENTS

| EP | 1 391 241 | 2/2004 |
|---|---|---|
| JP | 2004-271331 | 9/2004 |

(Continued)

OTHER PUBLICATIONS

N. R. Munce et al., "Microfabricated System for Parallel Single-Cell Capillary Electrophoresis", Anal Chem., vol. 76, pp. 4983-4989, 2004.

(Continued)

*Primary Examiner* — Nathan Bowers
(74) *Attorney, Agent, or Firm* — Wenderoth, Lind & Ponack, L.L.P.

(57) ABSTRACT

A device for individually analysing cells of interest, comprising (a) a channel for receiving the contents of a cell of interest, wherein the channel has an input end and an output end, and (b) a cell trapping site in proximity to the input end of the channel, wherein (i) the input end of the channel is adapted such that an intact cell of interest cannot enter the channel; and (ii) the channel contains one or more analytical components for analysing the contents of the cell of interest. In use, a cell is applied to the device, where it is trapped by the cell trapping means. The cell cannot enter the channel intact, but its contents can be released in situ to enter the channel's input end. The contents can then move down the channel, towards the output end, and they encounter the immobilised reagents, thereby permitting analysis of the cell contents.

88 Claims, 37 Drawing Sheets

U.S. PATENT DOCUMENTS

| | | | |
|---|---|---|---|
| 5,635,358 | A | 6/1997 | Wilding et al. |
| 6,156,576 | A | 12/2000 | Allbritton et al. |
| 6,184,029 | B1 | 2/2001 | Wilding et al. |
| 6,193,647 | B1* | 2/2001 | Beebe et al. ............. 600/33 |
| 6,524,456 | B1 | 2/2003 | Ramsey et al. |
| 6,538,810 | B1 | 3/2003 | Karanfilov |
| 6,586,253 | B1 | 7/2003 | Harrison et al. |
| 6,692,952 | B1 | 2/2004 | Braff et al. |
| 6,695,765 | B1* | 2/2004 | Beebe et al. ............. 600/33 |
| 6,846,306 | B1 | 1/2005 | Haas et al. |
| 2002/0142323 | A1 | 10/2002 | Allbritton et al. |
| 2003/0104466 | A1* | 6/2003 | Knapp et al. ............. 435/6 |
| 2003/0153067 | A1* | 8/2003 | Stett et al. ............. 435/285.2 |
| 2004/0029258 | A1* | 2/2004 | Heaney et al. ............. 435/287.2 |
| 2004/0037739 | A1* | 2/2004 | McNeely et al. ............. 422/58 |
| 2004/0067492 | A1 | 4/2004 | Peng et al. |
| 2006/0275782 | A1* | 12/2006 | Gunderson et al. ............. 435/6 |

FOREIGN PATENT DOCUMENTS

| | | |
|---|---|---|
| WO | 93/22053 | 11/1993 |
| WO | 93/22055 | 11/1993 |
| WO | 93/22058 | 11/1993 |
| WO | 96/14934 | 5/1996 |
| WO | 01/35071 | 5/2001 |
| WO | 01/88087 | 11/2001 |
| WO | 03/006948 | 1/2003 |
| WO | 03/074740 | 9/2003 |
| WO | 03/093791 | 11/2003 |
| WO | 2005/030997 | 4/2005 |
| WO | 2005/037425 | 4/2005 |
| WO | 2005/043154 | 5/2005 |

OTHER PUBLICATIONS

UK Search Report dated Oct. 28, 2005.

International Search Report dated Sep. 15, 2006.

International Search Report issued Sep. 15, 2006 in the International (PCT) Application of which the present application is the U.S. National Stage.

Krylov SN et al. Correlating cell cycle with metabolism in single cells: combination of image and metabolic cytometry. Cytometry. Sep. 1, 1999;37(1):14-20.

Bao G, Suresh S. Cell and molecular mechanics of biological materials. Nat Mater. Nov. 2003;2(11):715-25.

Andersson H, van den Berg A. Microtechnologies and nanotechnologies for single-cell analysis. Curr Opin Biotechnol. Feb. 2004;15(1):44-9.

Wu H et al. Chemical cytometry on a picoliter-scale integrated microfluidic chip. Proc Natl Acad Sci U S A. Aug. 31, 2004;101(35):12809-13.

Fu AY et al. An integrated microfabricated cell sorter. Anal Chem. Jun. 1, 2002;74(11):2451-7.

Munce NR et al. Microfabricated system for parallel single-cell capillary electrophoresis. Anal Chem. Sep. 1, 2004;76(17):4983-9.

Khine M et al. A single cell electroporation chip. Lab Chip. Jan. 2005;5(1):38-43.

Braff et al. (2002) Microsystems Technology Laboratories, MIT, Annual Report May 2002. 'Microfabricated Cell Analysis Device'.

Karen Cheung et al., Individually Addressable Planar Patch Clamp Array, $2^{nd}$ Annual International IEEE-EMBS Special Topic Conference on Microtechnologies in Medicine and Biology, pp. 71-75. (Corresponding to .pdf pp. 1-5), May 2002.

Kitagawa S et al. Manipulation of a single cell with microcapillary tubing based on its electrophoretic mobility. Electrophoresis. Aug. 1995;16(8):1364-8.

Di Carlo D et al. Reagentless mechanical cell lysis by nanoscale barbs in microchannels for sample preparation. Lab Chip. Nov. 2003;3(4):287-91.

Przekwas et al. Electrodynamic Transport, Electroporation and Lysis of Cells in Pharmacological and Bioanalytical Microsystems, Modeling and Simulation of Microsystems 2001, ISBN 0-9708275-0-4.

Sims CE et al. Laser-micropipet combination for single-cell analysis. Anal Chem. Nov. 1, 1998;70(21):4570-7.

Prinz C et al. Bacterial chromosome extraction and isolation. Lab Chip. Nov. 2002;2(4):207-12.

Leffhalm et al. "Single cell manipulation in microfluidic networks by optical tweezers" (2005) AKB 200.15 Di 17:00 Poster TU C. Berlin 2005, "Physik seit Einstein", Deutsche Physikialische Gesellschaft.

Lu et al. "Microfabricated Fluidic Devices for Cell Lysis and Subcellular Component Separations" (2002) Microsystems Technology Laboratories, MIT, Annual Report May 2002.

Lu et al. "Microfluidic Devices for Cell Lysis and Isolation of Organelles" (2001) pp. 297-298 of Micro Total Analysis Systems. Eds. Ramsey et al.

Lettieri & de Rooij "A Novel Microfluidic Concept for Bioanalysis Using Recirculating Flows" (2003) Centre Suisse d'Electronique et de Microtechnique (CSEM) Scientific and Technical Report 2003, p. 83.

Chiou PY et al. Massively parallel manipulation of single cells and microparticles using optical images. Nature. Jul. 21, 2005;436(7049):370-2.

* cited by examiner

FIGURE 3
FIGURE 3A
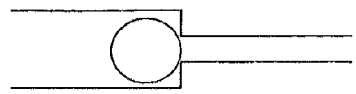
FIGURE 3B
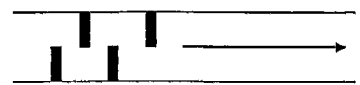
FIGURE 3C
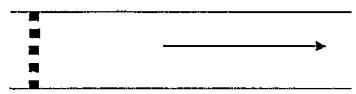
FIGURE 3D
FIGURE 3E
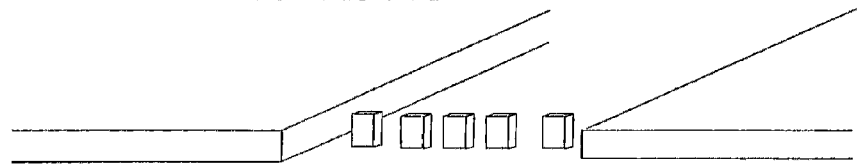
FIGURE 4
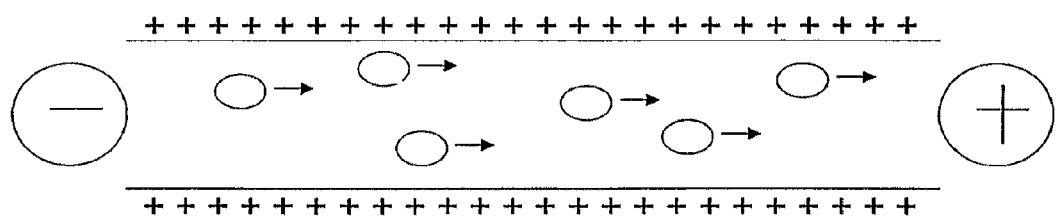
FIGURE 5
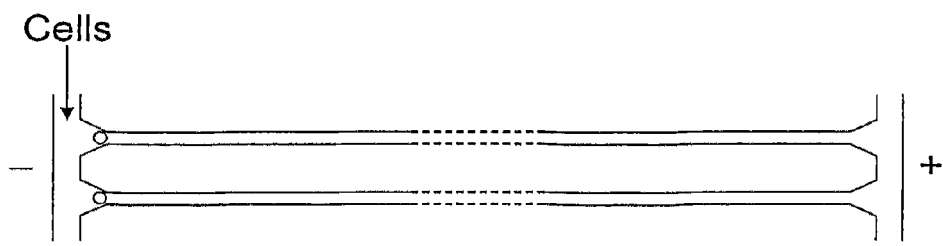

FIGURE 6
FIGURE 6A
Lysis solution
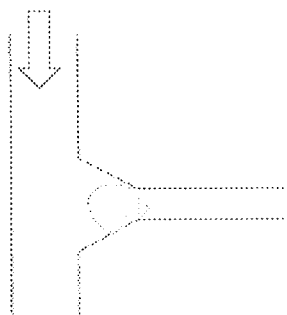
FIGURE 6B
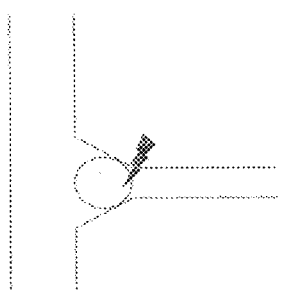
FIGURE 6C
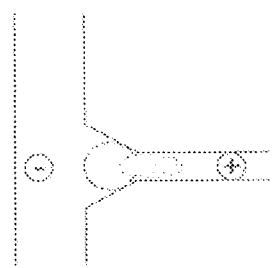
FIGURE 7
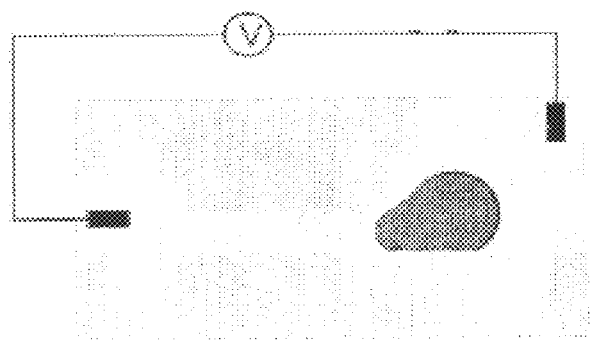
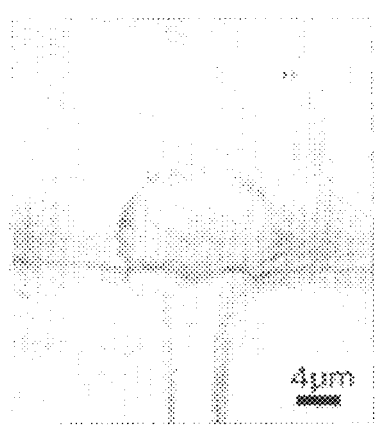
4μm
FIGURE 8
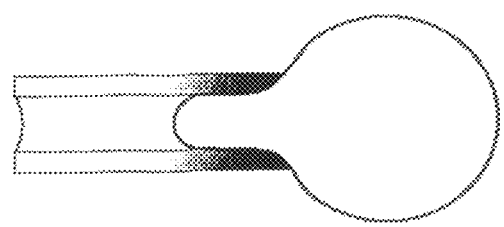

FIGURE 12
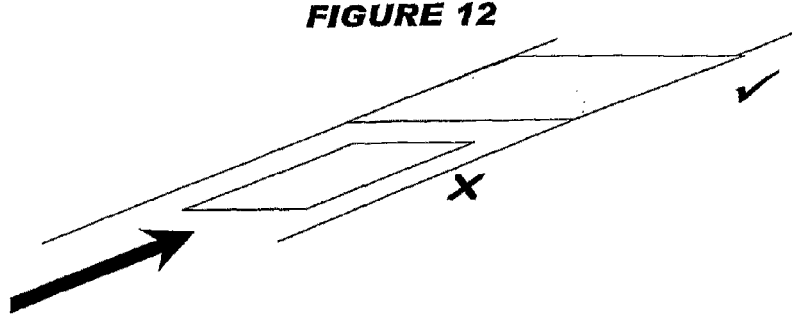
FIGURE 13
FIGURE 13A
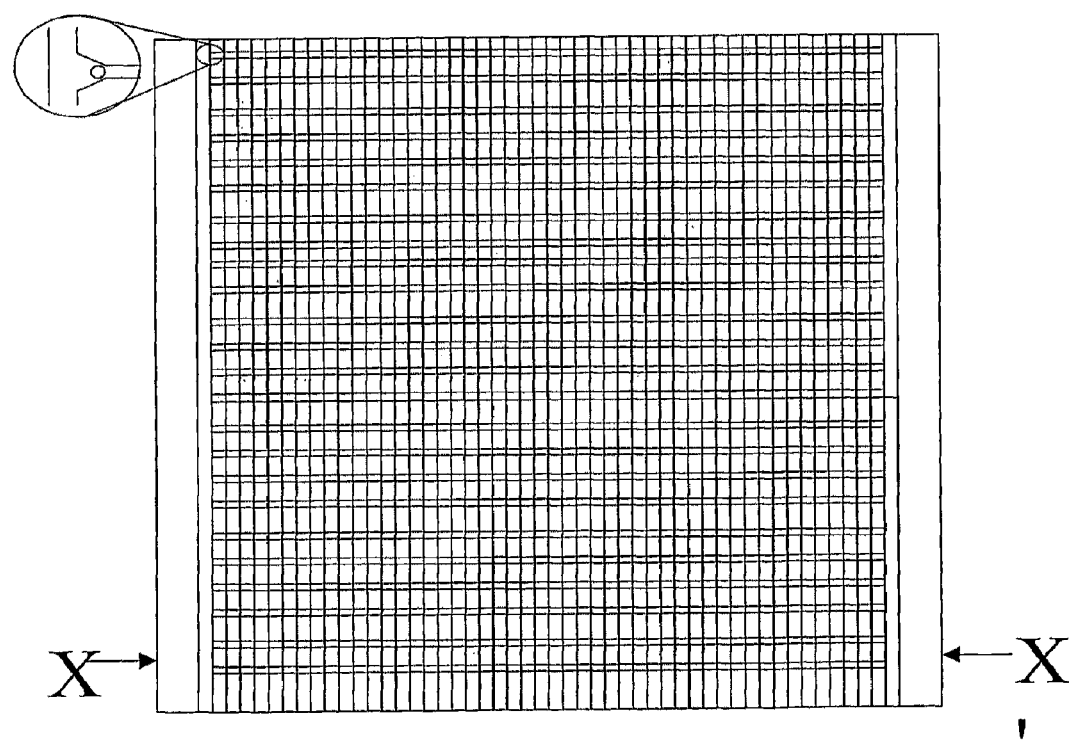
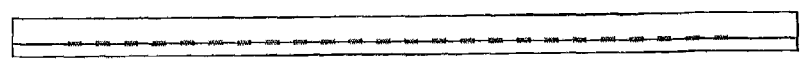
FIGURE 13B

3'-end recaptured    Reverse transcription

Repeat

Waste

Suction

FIGURE 32
FIGURE 32A
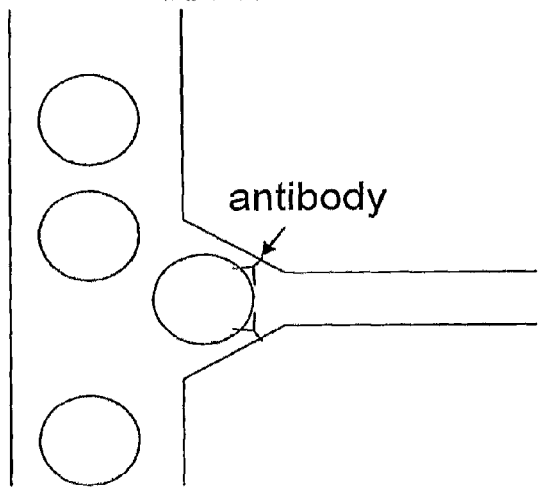
FIGURE 32B
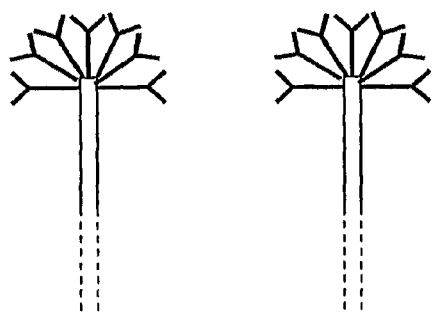
FIGURE 33
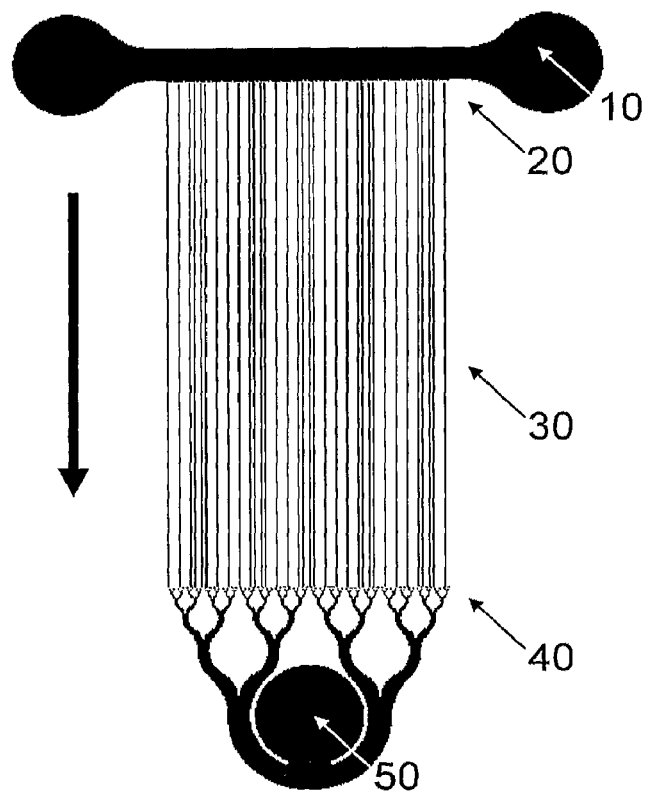

FIGURE 38
FIGURE 38A
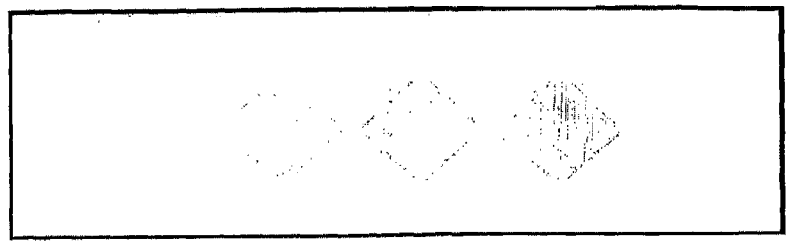
FIGURE 38B
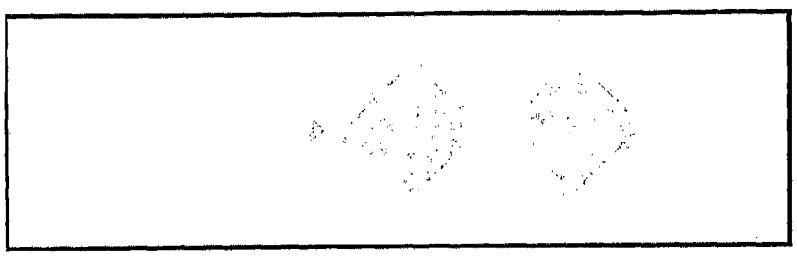
FIGURE 39
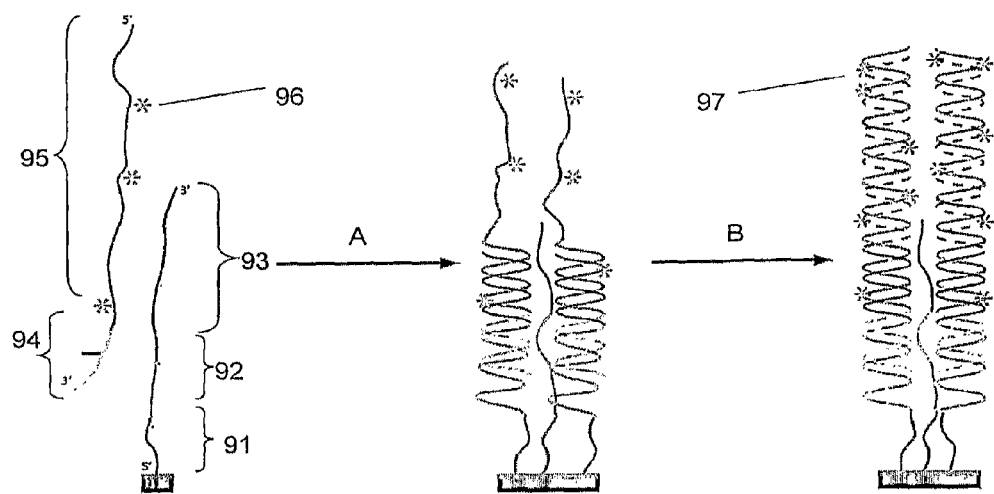

Increasing poly dT tract

FIGURE 43
FIGURE 43A
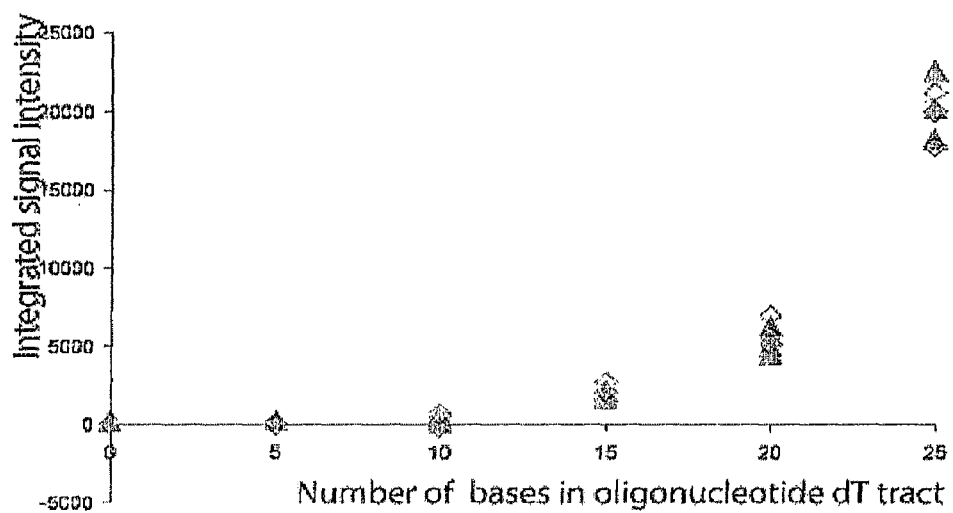
FIGURE 43B
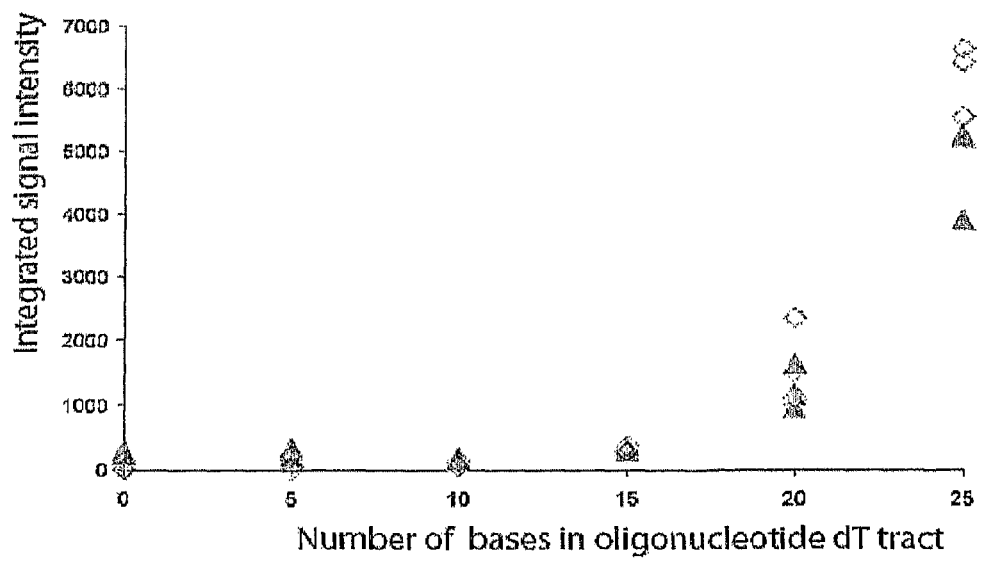

FIGURE 50
FIGURE 50A
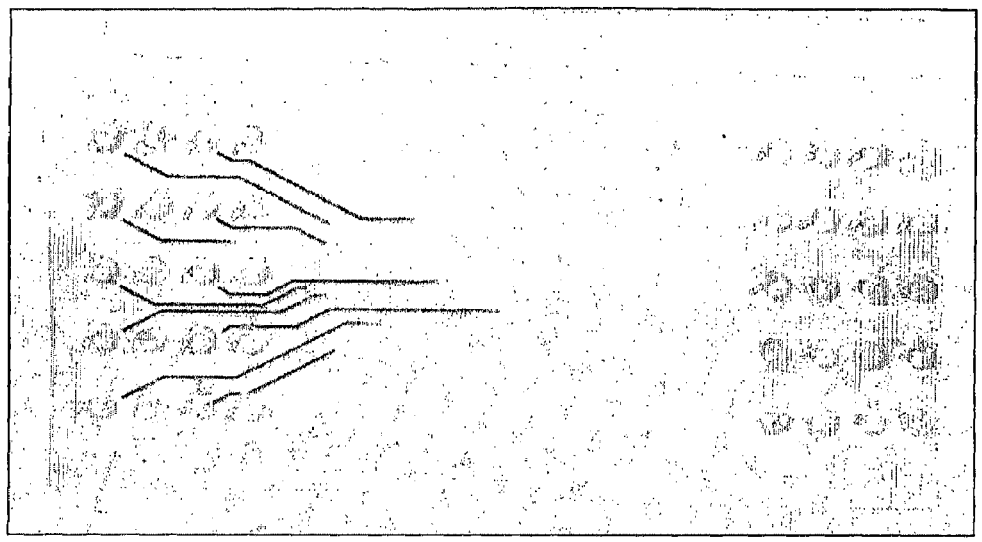
FIGURE 50B
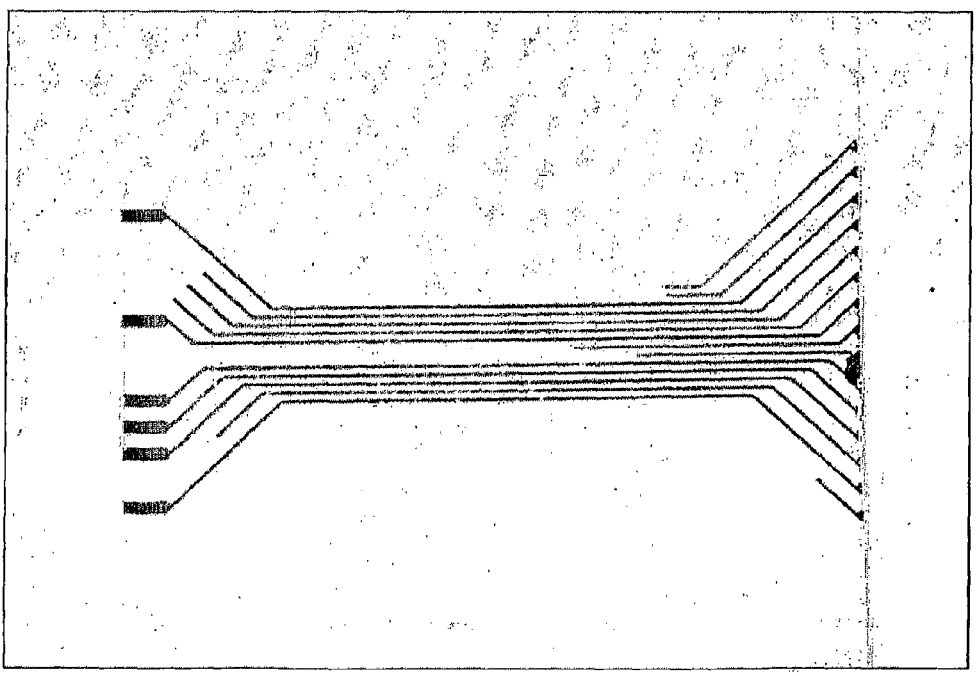

FIGURE 60
FIGURE 60A
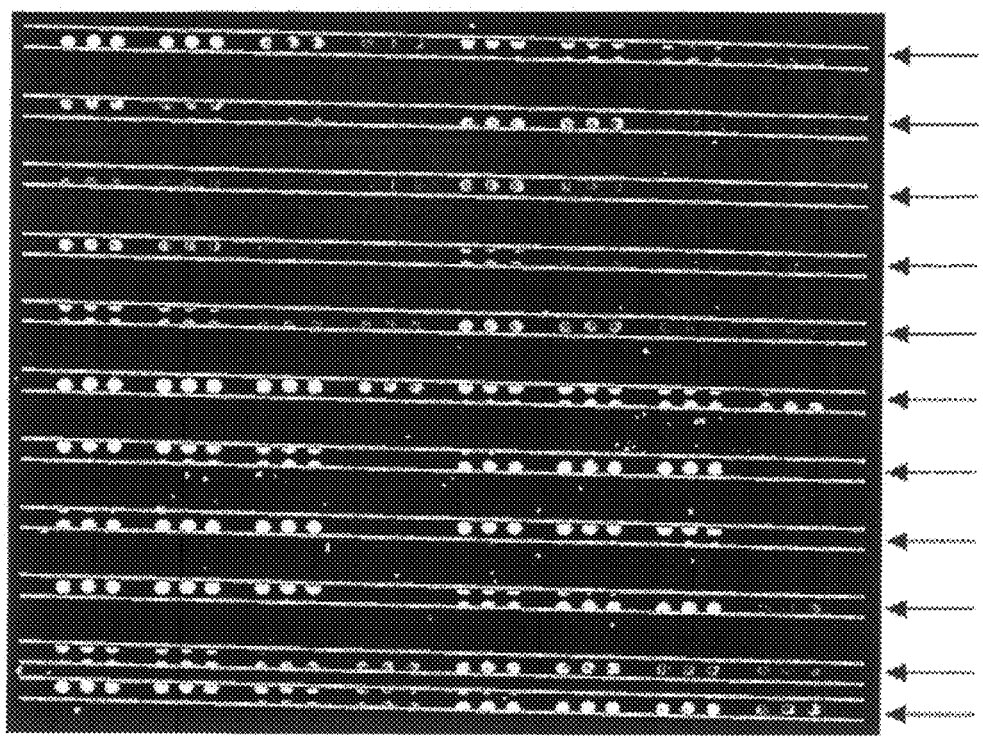
FIGURE 61
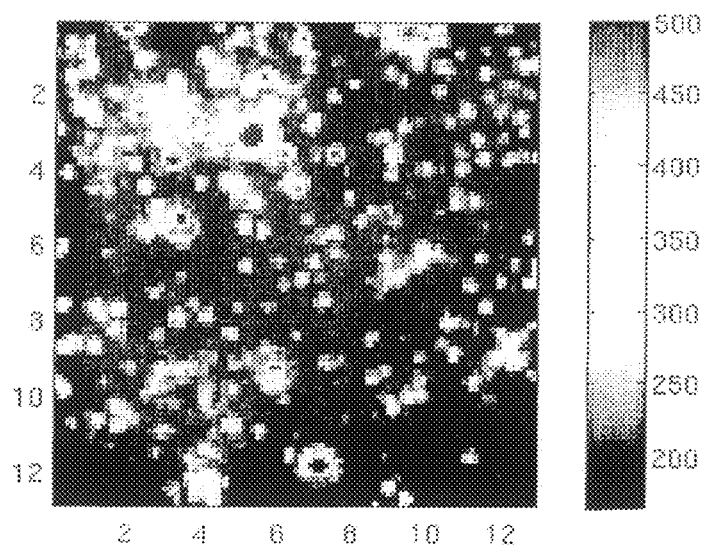

FIGURE 60B
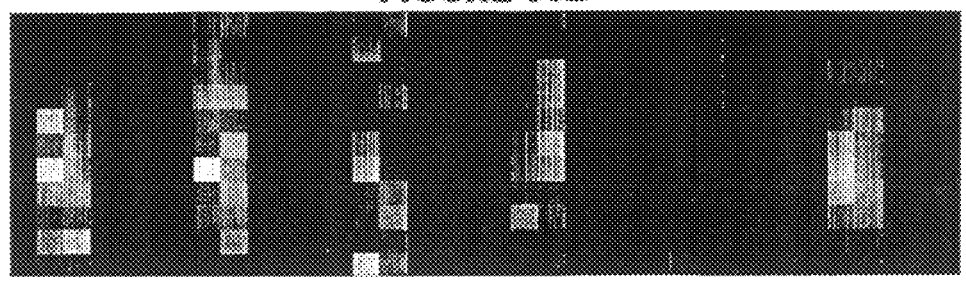
FIGURE 62
FIGURE 62A
FIGURE 62B
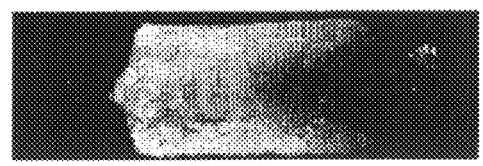
FIGURE 62C
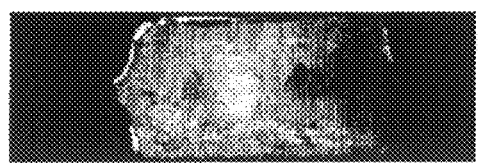
FIGURE 62D
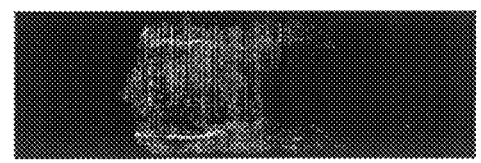
FIGURE 62E
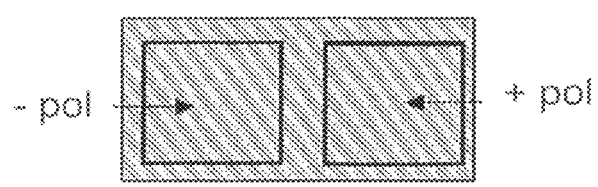
FIGURE 62F
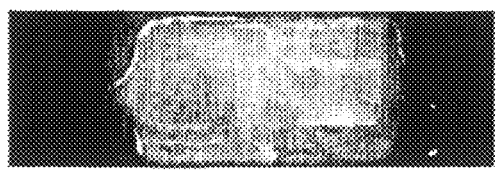
FIGURE 62G
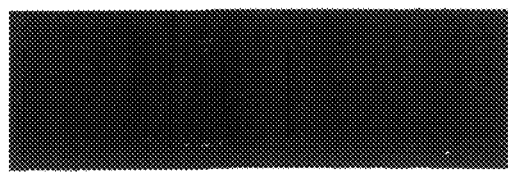

FIGURE 71
FIGURE 71A
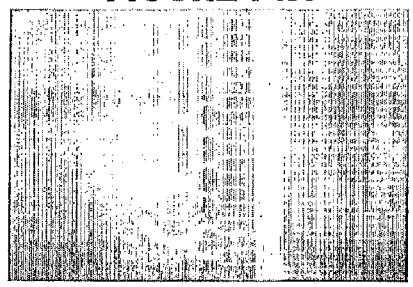
FIGURE 71B
FIGURE 71C
FIGURE 71D
FIGURE 73
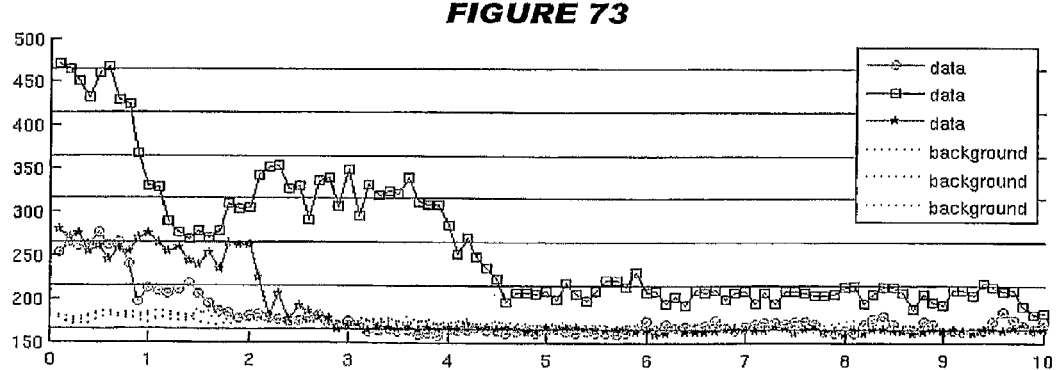

FIGURE 72
FIGURE 72A
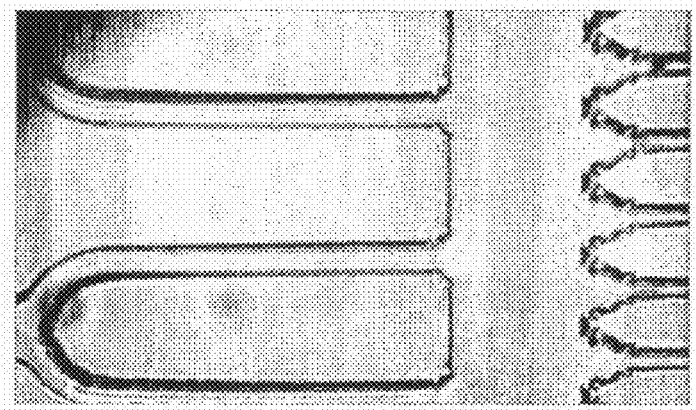
FIGURE 72B
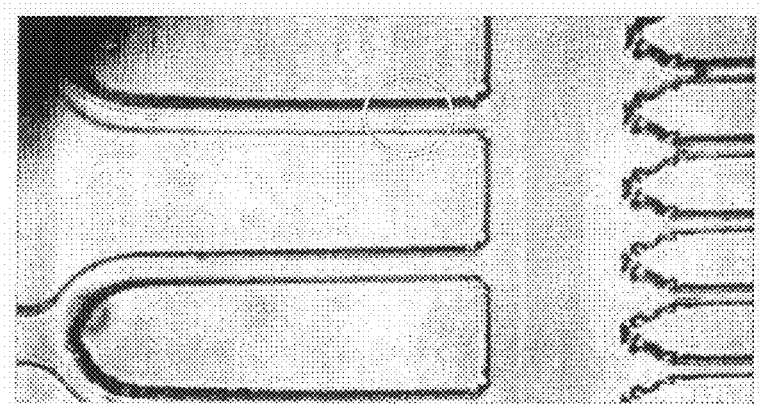
FIGURE 72C
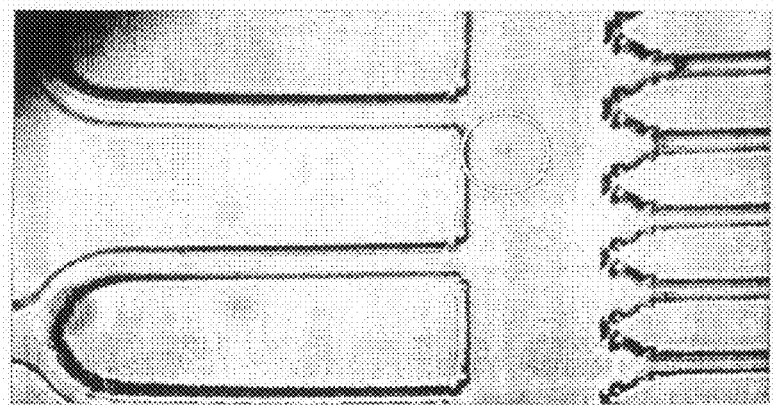

DEVICES AND PROCESSES FOR ANALYSING INDIVIDUAL CELLS

This application is a U.S. national stage of International Application No. PCT/GB2006/001593 filed May 3, 2006.

All documents and on-line information cited herein are incorporated by reference in their entirety.

TECHNICAL FIELD

This invention is in the field of cell analysis, and in particular the analysis of individual cells.

BACKGROUND ART

There are many methods for biochemical characterisation of cells and tissues. Methods such as electrophoresis, chromatography, mass spectrometry, microarrays, etc. are used to analyse the molecular composition of cells or tissues. The results of such analyses may indicate a disease state, for example. Analyses are most often carried out after lysing cells to release their contents, and it is usually necessary to use a large number of cells, because it is difficult to isolate single cells and because normal methods of detection are not sensitive enough to measure the contents of single cells.

It is rare, however, to find a living system comprising cells that are all in the same state: cell cultures artificially synchronised in the laboratory may approach homogeneity, but cells even of the same type in a natural situation will be in different states e.g. at different stages in the cell cycle, etc. Typical analyses thus represent an average of cells being analysed.

For a more complete description of the state of any system, it would be advantageous to analyse individual cells. For example, many disease states in humans elicit changes to the white blood cells, and in Hodgkin's lymphoma it has been shown that the gene expression pattern of individual lymphocytes is not representative of the population as a whole [1]. Analysis of a mixture of cells thus masks heterogeneity within the mixture, and fails to provide information which is likely to be important for understanding the disease state. Subtle but important variations between cells are lost within experimental noise.

There are many examples in biology and medicine where analysis of individual cells would be more useful than analysis of a complete population or collection. It is a major objective of developmental biology to have a description of the molecular changes that accompany growth and differentiation of an organism. Embryological studies by definition begin with a single cell. Processes in living cells are organised into systems that respond to stimuli: to study such systems and their controls it is necessary to measure levels of molecules involved—mRNAs, proteins, metabolites etc.—in a number of cells. Disease states are often reflected in the composition of cells and tissues. Cancer cells differ from their normal counterparts in the genes that are expressed at the mRNA and protein levels. Fetal blood cells can escape into maternal circulation and must be analysed separately from the maternal cells. Autoimmune and infectious diseases result in changes to the composition of the white blood cells. Circulating white blood cells are themselves heterogeneous and comprise several different functional types, including neutrophils, lymphocytes, monocytes and platelets. A description of the molecular compositions of such collections of cells will advance basic understanding of biological systems and processes and can inform research into the causes and treatment of disease.

Reference 2 coined the term "chemical cytometry" to describe the use of high-sensitivity chemical analysis techniques to study single cells, and reference 3 reviews basic features of single cell analysis. Reference 4 reviews microtechnologies and nanotechnologies for single-cell analyses. Reference 5 describes microfluidic devices for manipulating single cells. Single cell isolation apparatuses are disclosed in references 6 & 7.

It is an object of the invention to provide further and improved devices and processes for analysing individual cells, and in particular their genomes, transcriptomes and proteomes.

DISCLOSURE OF THE INVENTION

The invention provides in general a convenient way of isolating individual cells in an apparatus which permits individual analysis of their contents. Single cells are trapped, their contents are released, and the contents of individual cells are then analysed along a channel containing suitable analytical components e.g. immobilised nucleic acid probes, immobilised antibodies, etc. Analysis of a single cell's genome, transcriptome, proteome, etc. thus becomes possible. Moreover, by arranging multiple channels on the same device, multiple cells can simultaneously be treated and analysed in parallel, allowing individual cells within a population to be compared rapidly and conveniently. Where the multiple channels share a common input line, a population of cells can easily be separated into single cells, with one cell being associated with each channel.

Thus the invention provides a device for individually analysing cells of interest, comprising:
- a channel for receiving the contents of a cell of interest, wherein the channel has an input end and an output end; and
- a cell trapping site in proximity to the input end of the channel, wherein:
- the input end of the channel is adapted such that, during use, an intact cell of interest cannot enter the channel;
- the channel contains one or more analytical component(s) for analysing the contents of the cell of interest; and
- the contents of the cell of interest can be moved along the channel, in a direction from the input end towards the output end.

In use, a cell is applied to the device, and it is trapped at the cell trapping site. The cell cannot enter the analysis channel intact, but its contents can be released in situ to enter the channel at the input end. The contents can then be moved along the analysis channel, where they encounter the analytical component(s), thereby permitting analysis of the cell contents.

As described above, in a preferred embodiment the device has a plurality of channels, such that the contents of multiple cells can be separately analysed in parallel. Thus the invention provides a device for individually analysing cells of interest, comprising:
- a plurality of channels, each of which is for receiving the contents of an individual cell of interest, wherein each of the channels has an input end and an output end; and
- a cell trapping site in proximity to the input end of each channel, wherein:
the input ends of the channels are adapted such that intact cells of interest cannot enter the channel;
each channel contains one or more analytical component(s) for analysing the contents of the cells of interest; and
the contents of a cell can be moved along the channels, in a direction from the input ends towards the output ends.

Preferably the channels are substantially identical to each other (e.g. in terms of dimensions, material, analytical component(s), etc.) such that, during use, cells in different channels are separately subjected to substantially the same treatment and analysis as each other, allowing direct comparison of results. The channels are preferably parallel to each other. In an alternative arrangement, however, channels may radiate from a central point (FIG. 23). It is also possible to arrange parallel channels extending in different directions from a central point (FIG. 24). An arrangement where channels run in the same direction is preferred, however, as electrokinetic movement of material is then easier to achieve. Where channels run from a delivery line in different directions then valves etc. may be required in order to achieve equivalent movement through different channels.

Performing identical individual analysis in parallel on different cells is particularly powerful and readily allows differences to be detected in apparently identical cells. Thus the invention provides a device for individually analysing a plurality of cells, comprising a plurality of channels, each of which is for receiving the contents of an individual cell, wherein each channel contains a sequence of analytical components along the channel, and wherein the sequence of analytical components in one channel is the same as in another channel. Thus different cells will experience a common analysis regardless of the channel which they encounter, and the results from one channel can readily and directly be compared to the results of another channel.

The invention provides a process for analysing an individual cell of interest, comprising the steps of: trapping the cell in proximity to the input end of a channel that has an input end and an output end, the input end being adapted such that the cell of interest cannot enter the channel intact; releasing the cell's contents such that they enter the input end of the channel; allowing the released contents to move from the input end towards the output end, such that they interact with one or more analytical component(s) within the channel, thereby permitting analysis of the contents.

The invention also provides a process for analysing a plurality of individual cells of interest, comprising the steps of: trapping individual cells in proximity to the input ends of a plurality of channels that each have an input end and an output end, the input ends being adapted such that the cells of interest cannot enter the channels intact; releasing the cells' contents such that they individually enter the input ends of the channels; allowing the released contents to move from the input ends towards the output ends, such that they interact with one or more analytical component(s) within the channels, thereby permitting analysis of the contents.

The invention also provides a process for analysing a plurality of individual cells, comprising the steps of: individually releasing the contents of a plurality of individual cells; applying the individual contents to individual channels within a single device, wherein each channel contains a series of sequential analytical components, and wherein the sequence of analytical components in one channel is the same as in another channel.

Different analyses can require different devices within the scope of the invention. For instance, different cell types may require devices with different dimensions. Different analyses of the same cell type may use different analytical components e.g. for proteome analysis vs. transcriptome analysis, or for cell cycle analysis vs. cell signalling analysis. Moreover, devices can be designed based on previous experimental data, and can be used in different ways depending on previous experience. For example, if a device fails to give useful data in an initial experiment, variables such as flow rate, temperature of operation, the type of analytical component, etc. can be altered in further experiments, and signal amplification techniques can be used, as described in more detail below. Different experiments can thus use different features, as described herein, depending on the desired analysis.

The Device

Devices of the invention have several features, including analysis channels, cell trapping sites, etc. These features can be formed by assembling separate components and/or by forming them from a single piece of material (e.g. by casting, etching, etc.). Because the dimensions of the device are in the cellular range, microfabrication methods will typically be used. Advantageously, the various features described herein form an integrated device.

The choice of materials for the device is influenced by a number of design considerations, and suitable materials can readily be selected by the skilled person based on the requirements of a particular device. For example, the material(s) should be amenable to microfabrication, stable to the reagents used in cellular manipulation analysis, and compatible with the methods used for observing and measuring cells and molecules. Materials impermeable to the reagents used during analysis will generally be used. For some applications, it will be necessary to attach reagents covalently to the surface of a material. For some applications it will be desirable to use a hard material; other applications may need a flexible material. Where fluorescence is used for detection then the material should be transparent to the excitation and emission wavelengths, and also have low intrinsic fluorescence at these wavelengths. Where electroosmosis is used to move material about the device then the material should be charged during use, or should be able to carry charge. For example, the skilled person can choose to give a positive or negative charge to silicon, glass and PDMS surfaces by derivatising them with appropriate silanising reagents. Materials that can propagate an illuminating evanescent wave (by total internal reflection) may be preferred for use with certain detection techniques.

Suitable materials and fabrication methods are well known. Hard materials such as silicon and glass, for which microfabrication methods have been in use for many years, can be used. Recent developments in 'soft lithography', which exploits the potential to mould devices in polymers, such as polydimethylsiloxanes (PDMS), have enabled convenient methods for fabrication of microfluidic devices at the cellular scale (e.g. reference 8 discloses an integrated microfabricated cell sorter formed by multilayer soft lithography, including peristaltic pumps, dampers, switch valves, input wells and output wells, to perform cell sorting in a coordinated and automated fashion, with the active volume of an actuated valve being as small as 1 pl and the volume of optical interrogation being ~100 fl). Such devices have channels similar to those in devices of the present invention, and incorporate other features used in some embodiments of the invention, such as flow cells illuminated by lasers for measurement of fluorescence.

Thus devices of the invention can be made from a variety of materials, including but not limited to silicon oxides, polymers, ceramics, metals, etc. and mixtures thereof. Specific materials that can be used include, but are not limited to:

glass; polyethylene; PDMS; polypropylene; and silicon. PDMS is a particularly useful material, and the devices can be conveniently made by using casting, injection molding or UV-patterning and curing.

In addition to having channels and cell trapping sites, other features of devices can include:

- A delivery line in communication with the cell trapping site(s). Cells can be introduced into the device via the delivery line, from which they can access and be trapped by the cell trapping sites, from where their contents can then enter the analysis channels. Cells that are not trapped can be flushed out of the waste end of a delivery line. The use of a common delivery line is particularly advantageous for a device with multiple channels, as the different channels all receive cells from the same source. Where the channels are parallel to each other, the delivery line may run perpendicular to the channels (e.g. FIG. 1) but, in an alternative arrangement, may branch into delivery channels that are parallel to the channels (e.g. FIGS. 53 & 54). To minimise accidental lysis, delivery lines should be larger in all dimensions than the cells to be analysed e.g. 25-250 μm high.
- A reagent supply line in communication with the cell trapping site(s), for applying chemical reagents (e.g. lysis reagents, or chemical stimuli) to cells, and in particular to trapped cells. The reagent supply line may be the same as the delivery line (e.g. FIG. 1), or it may be separate from the delivery line (e.g. FIGS. 53 & 54). Where the analysis channels are parallel to each other, the reagent supply line will typically run perpendicular to those channels.
- An exhaust in communication with the output ends of the analysis channels. Material leaving the channels can thus be directed towards waste. Exhausts can also be used for controlling flow through channels.
- One or more electrodes. Electrodes can be used to generate an electrical potential across a device, and in particular along an analysis channel e.g. to move cells by electrokinesis, to allow electroporation, etc. As an alternative, the device can include contacts for the connection of external electrodes.
- A piezoelectric device in order to lyse cells.
- A light source e.g. a laser. This can be used for various purposes e.g. for cell lysis, to view the progression of a meniscus in channels, to excite fluorophores, etc.
- An image capturing element, such as a camera. This may capture still and/or moving images. It will typically be a digital camera.

Where the device includes a plurality of channels, these will generally be arranged next to each other within a single plane. It is possible to stack planes of channels, such that the channels will be arranged three-dimensionally, but ease of manufacture (particularly applying reagents to the insides of analysis channels) and result gathering (particularly reading analysis data within channels) means that substantially planar arrangements of channels are preferred. The overall device, however, may extend beyond the plane of the channels e.g. delivery lines, exhausts, etc. may be outside the plane of the channels.

Cell Trapping Sites

Rather than rely on simple diffusion of cells into channels to provide material for analysis, the device of the invention includes cell trapping sites. Cells are individually trapped such that, when their contents are released for analysis, they can enter individual channels. A cell trapping site is thus physically connected and located in proximity to the input end of a channel such that, when released, the trapped cell's contents can enter the channel via its input end.

The cell trapping site can be arranged such that it can trap only a single cell. This will typically be achieved by using dimensions that can accommodate only a single cell of interest, and/or by using a cell trapping site that becomes unable to trap further cells once one cell has been trapped.

Cell trapping sites can take various forms, provided that they can trap a cell such that its contents can be released for entry to an analysis channel. In a simple device, the cell trapping site could be the entrance to the analysis channel at its input end. It is known, for instance, to trap cells on the end of a glass micropipette. In general, however, the cell trapping sites will take the form of a tapered inlet before the input end of an analysis channel, having a larger diameter that a cell can enter and a smaller diameter that a cell cannot leave (e.g. diameters of 15 μm and 3 μm for a human lymphocyte; see further below). Thus a cell can enter the tapered inlet, but it cannot continue into the analysis channel, as reported in reference 9. The smaller diameter of the taper can lead straight into an analysis channel. See FIGS. 1 & 2. The taper can be in one dimension or in two dimensions e.g. a taper could have a constant height and a narrowing width (FIG. 15A; also FIG. 35), or can have narrowing height and width (FIG. 15B). The taper can be linear (e.g. FIG. 2) or non-linear (e.g. FIG. 70). It can be smooth or stepped. Further advantages of a tapered cell trapping means arise from the ability to extend a small portion of the cell down the taper, as described in further detail below (see also FIGS. 8 & 70). The same effect as a taper can be achieved by having a site which is initially closed (at least partially) at its downstream end, such that a cell can enter but cannot continue downstream, but can later (e.g. after lysis) be opened (e.g. by the use of a valve) to permit further downstream movement.

Further ways of physically trapping cells are illustrated in FIG. 3. In FIG. 3A, a stepped reduction in diameter is used rather than a tapered one. In FIG. 3B, baffles are arranged in a channel such that a cell gets caught as it moves. In FIGS. 3C, 3D and 3E, posts are arranged across a channel, and these catch cells.

The trapping sites allow single cells to be captured due to the movement of fluid within the device, rather than being maneuvered into place by a user. Occupancy of a cell trapping site can be at random, but is preferably assisted e.g. by using a motive or attractive force, particularly when using a tapered inlet. For instance, an electrical (e.g. electroosmotic; see further below) or mechanical (e.g. suction, conveniently through the analysis channels) force can be applied, to encourage cells to enter trapping sites. This force can facilitate efficient analysis by increasing the likelihood that all cell trapping sites are occupied when analysis begins, and by accelerating the process by which the trapping sites become occupied. The use of suction pressure to facilitate hydrodynamic trapping of single cells at the entrance to a channel (FIG. 8) has been described in reference 10. The use of electrical potential to move individual cells is familiar from the Coulter counter.

To prevent multiple cells being attracted into the same trapping site then the attractive force for a site may be arranged to cease once it becomes occupied; in addition, should a cell escape from a cell trapping site then the attractive force should resume e.g. if suction is used then a trapped cell can block and stop the suction from attracting further cells, but if the cell leaves then the suction will begin again and can re-attract the leaving cell.

For electroosmotic movement of cells into a cell trapping site, an electrical potential is applied to the device, generally with the cathode upstream of the trapping site (e.g. in the delivery line) and the anode downstream (e.g. downstream of the analysis channel). A potential gradient of 1-2 v/cm will typically cause a cell to lyse, and so the potential used to move a cell intact will be lower than this e.g. 0.1-0.3 v/cm. A cell moving by electroosmosis will enter a tapered trapping site and move into the narrow end of the taper, where it will be trapped. With the taper being blocked then current can no longer flow and so electroosmosis will cease. If the cell disengages from the narrow end of the taper, however, current flow will resume and the cell will again move towards the anode and will be re-trapped. Electroosmosis therefore permits efficient trapping of cells. See FIG. 5.

Occupancy of a cell trapping site can be facilitated by including cell retention means. These will not actively attract cells, but will keep cells in place once they have occupied the cell trapping site. Examples of cell retention means include immobilised antibodies that recognize cell-surface molecules on a cell of interest. See FIG. 32.

In general, therefore, the $k_{on}$ and/or $k_{off}$ of a cell trapping site can be manipulated with the overall goal of trapping an individual cell in proximity to a channel's input end e.g. by the use of suction (improves $k_{on}$) or by the use of immobilised antibody (improves $k_{off}$).

A microfabricated device formed from PDMS with individual lateral cell trapping sites that can selectively immobilise single cells is disclosed in reference 10. A MEMS device that traps single cells in wells and uses microbubbles to release them is described in refs 11 & 12. Microfabricated devices formed from silicon wafer for patch clamp analysis of individual trapped cells is reported in reference 13, with nozzle sizes of 1 μm, 3 μm and 10 μm. Rather than use physical trapping sites, however, individual cells be trapped by non-contact means e.g. by the use of opposing electrokinetic and pressure-driven forces [26].

Reference 14 describes trapping and manipulation of a single cell using capillary tubing and an electrostatic field. A single cell migrates with its electrophoretic mobility into capillary tubing against the flow of electroosmosis coming out of the capillary. After trapping the cell in the capillary, it is pulled out into a microreservoir by applying a reverse electric voltage. When a negative voltage was applied to the microreservoir, a cell in it can keep floating for a relatively long period due to electrostatic repulsion.

In a preferred arrangement, a device includes a tapered inlet, into which cells (e.g. coming from a delivery line) are moved by the use of electrokinesis, and especially electroosmosis. The cells become physically trapped at the bottom of the taper, at the entrance to a channel, into which their contents can later be subjected to analysis.

Releasing the Contents of a Cell

When a cell has been trapped, its contents can be released e.g. by cell lysis. The contents can be released in various ways. For instance, a lysis solution can be applied to the device (e.g. via the delivery line), and a cell will be lysed in situ within a cell trapping site (FIG. 6A). As an alternative, the cell trapping site can be adapted to mechanically rupture a trapped cell (FIG. 6B) e.g. using the 'nanoscale barbs' described in reference 15. As a further alternative, the cell contents can be removed by electroporation (FIG. 6C) and, depending on the magnitude of the electric field used for electroporation, a membrane may simply be opened, allowing access to a cell's contents, or may rupture, leading to cell lysis [16]. A field strong enough to cause lysis is preferred.

Typical lysis solutions that can be used may comprise components such as: a surfactant e.g. an ionic detergent such as SDS when analysing nucleic acids, or a non-ionic detergent such as Triton-X100 when analysing proteins; an enzyme to digest proteins e.g. proteinase K; an enzyme to digest nucleic acids e.g. a DNase and/or RNase; a chaotrope to inactivate enzymes and solubilise cellular components e.g. a guanidine salt, such as guanidinium isothiocyanate; etc. Such reagents are commonly used in existing techniques for bulk cell lysis. The choice of reagent(s) will depend on the nature of the analytes of interest e.g. if the aim is to analyse mRNA then proteases and DNase may be included in the lysis solution, but not reagents that degrade mRNA.

Mechanical rupture of single cells has been described. Reference 17 discloses a method for fast lysis of a single cell (or cellular component thereof) by generating a shock wave, and to minimise manipulation trauma the cell is either positioned by laser tweezers or is cultured as an adhered cell. Ultrasonic vibration can also be applied to the device in order to lyse cells, as can laser light, which has previously been used to lyse single cells [18,19]. Lysis of single cells in a microfluidic device by osmotic shock is reported in reference 20. Reference 21 describes navigation and steering of single cells with optical tweezers to different areas of a microfluidic network where the flow properties can be controlled by electrophoresis and electroosmosis. A cell is captured between two electrodes where it can be lysed by an electric pulse.

Microfluidic devices which use electroporation to lyse small numbers of cells have been reported, using a device comprising multiple metal posts and a narrow flow channel [22,23]. Electroporation of single cells for removal of the contents has also been described e.g. see references 10 & 24. Although the focus of references 10 & 24 is to facilitate the delivery of materials into cells, the same principles apply to the removal of cellular contents because opening of the cell's membrane allows two-way traffic, as shown in FIG. 9. Human cells can be electroporated in situ using low applied voltages (<1 volt) for removal of their contents. By trapping individual cells before electroporation and by extending a small portion of the cell forwards, localized electroporation can be achieved at low voltages because the electric field is focused such that the greatest potential drop occurs across the leading membrane of the cell. Because resistance is inversely proportional to surface area, the small extended portion of the cell has a much higher resistance (e.g. at least 50-fold greater) than the unextended portion. The greatest potential drop therefore occurs across the extended portion of the cell membrane. Low applied voltages are sufficient to achieve electroporation with a high electric field across the leading membrane (e.g. greater than 500 kV/cm), which is within the range (300-1000 kV/cm) reported in reference 25 for the dielectric strength of a bilipid membrane. To achieve the greatest partial extension of a cell in this way, the cell trapping means is preferably tapered, and is more preferably tapered in two dimensions. See FIG. 7.

Electroporation of single cells is a preferred method for releasing a cell's contents.

Before a cell's contents are applied to analytical reagents within the device's channels (or after some analysis has taken place, but before the analysis is complete), it may be desired to remove certain components from the contents and/or modify certain components. Biochemical analysis is often preceded by such purification or modification steps to remove substances which may interfere, either in terms of an analyte's interaction with a reagent, or accessing or interpreting results. One aspect of the invention, however, is that these removal steps may not be required. It has been found that mRNA analytes can reliably be captured for detectable hybridisation even against a background of cellular contents (e.g. see FIGS. 60 & 62). Thus the invention provides a process for individually analysing one or more cell(s) of interest, comprising the steps of: (i) releasing the contents of a cell; and (ii) capturing mRNA from the released contents by hybridisation to an immobilised nucleic acid, wherein there is no step of mRNA purification between steps (i) and (ii). Thus step (ii) can take place in the presence of released cell contents, lysis reagents used in step (i), etc.

Where a removal step is included, however, there are two preferred positions for performing it. In a first embodiment, a device can include an expansion chamber upstream of a channel's input end (e.g. between the cell trapping site and the channel's input end) or immediately downstream of an input end. A cell's contents can enter the expansion chamber where treatment reagents can be introduced e.g. via the same route by which the cell's contents entered (FIG. 10). The use of an expansion chamber avoids the diffusion of released contents back into the delivery line, as may happen if the lysed cells are left in trapping sites. In a second embodiment, treatment reagents can be introduced along the analysis channel, without the need for an expansion chamber.

In a further embodiment, cells can be halted in the device while fluid movement continues. For example, reference 26 describes the use of opposing electrokinetic and pressure-driven forces for halting a cell within microfluidic devices. Fluid movement can continue while cells remain stationary, trapped by non-contact means, and so treatment reagents can be introduced into the moving fluid and applied to the stationary cells. Different cells can require different operating electric fields and applied pressures in order to be trapped in this way e.g. it was found that $E.\ coli$ cells require a buffer with a larger $\mu^{eof}$ than for yeast cells, as in a pH 7 Tris buffer ($\mu^{eof}=4\times 10^{-4}\ cm^2/Vs$) $E.\ coli$ can oppose the electroosmotic flow whereas yeast follow the flow.

Suitable treatment reagents include, but are not limited to: nucleases (e.g. DNase), proteases, lipases, amylases, cation exchangers, anion exchangers, detergents, chaotropes, etc. These reagents can be introduced into the device after the cell's contents have been released, or they can already be in place. In a preferred arrangement, treatment reagents are immobilised in the device e.g. enzymes immobilised on the internal surfaces of the device, plugs of resins in powder form or as frits, etc.

The treatment reagents are preferably arranged such that the cell's contents are treated to remove proteins and DNA, to leave enriched mRNA for analysis. As mentioned above, however, this removal is not always necessary.

Before interacting with analytical reagents, it is also possible to separate components within the cell contents. For example, a channel may contain a mRNA-specific capture reagent (e.g. immobilised poly-T nucleic acids). Other cellular components (e.g. proteins) will continue to move past the mRNA-specific capture reagent, and can then interact with analytical components within the channels. If nucleic acid hybridisation is then disrupted (e.g. temperature is increased, salt concentration is decreased, etc.), mRNA will be released and can follow the proteins down the channels. Other reagents for reversibly capturing classes of cellular components (e.g. for capturing DNA, proteins, mRNA, sugars, etc.) while letting others pass can be used similarly.

The time between trapping and lysis is preferably short e.g. to prevent the cell from dividing after being trapped. As an alternative, the device can be used at low temperatures (e.g. 2-8° C.) to inhibit cell division and other cellular processes.

Before lysis begins, it is preferred that delivery of cells to channels should cease, otherwise there is a risk that a second cell might be trapped by a cell trapping site which has already been used, thus leading to the contents of more than one cell entering a channel.

The Channels

Devices of the invention include channels, down which the contents of a cell can pass for analysis. The channels have an input end and an output end. The input end receives the contents of a cell, released from a trapped cell. The cell contents move along the channel from the input end towards the output end. At the output end, contents of the cell that remain (after preparative and/or analytical processes have been performed along the channel) can exit the channel.

The input end of the channel is adapted such that an intact cell of interest cannot enter the channel. This will typically be achieved by the input end being smaller than the cell of interest. As cells are not rigid bodies, a portion of the cell may extend into the channel (FIGS. 7 & 8), but the cell as a whole will not be able to enter the channel intact.

The channel's input end may be directly downstream of the cell trapping site. In an alternative arrangement, the cell trapping site and the input end may be separated by an intermediate region. For example, this intermediate region can take the form of an expansion chamber (see above; FIG. 10) into which a cell's contents may pass for treatment with reagents prior to analysis.

The dimensions of analysis channels can have an important impact on a device's performance. The dimensions are important not only for preventing entry of the cell, but also to reduce the distance through which molecules released from the cell's contents must diffuse to meet analysis components within the channels. Further details of dimensions are given below.

Channels will typically have a substantially constant cross-sectional area, and preferably a substantially constant cross-section shape. Variations in cross-sectional area lead to variations in flow rate through the channel, which is not usually desirable. A rectangular cross-section area is preferred, as explained in more detail below.

If electroosmosis is used to move material along a channel then at least one wall of the channel will have an appropriately charged surface during use. The polarity and magnitude of the charge can be selected depending on the direction and rate of movement desired in any particular analysis. Polarity can depend on both the underlying material used to make the channel, on any surface-attached material (e.g. immobilised nucleic acids) and on any surface modifications. If a positively-charged material is used for one wall of a channel, and DNA and/or RNA is immobilised in discrete locations on the opposite wall, localised zeta potential variations will result in contraction and expansion of the bulk flow streamline distribution, giving rise in turn to differential transverse mass transfer rates and hence mixing. A similar effect can also be obtained using embedded electrodes, as demonstrated in references 27 and 28, by using pulses of electrical potential across a channel between the electrodes. Mixing effects and turbulent flow may be desirable in some assays but may be undesirable in others. The skilled person can choose these conditions according to their needs, and suitable conditions can be determined empirically.

The channels are preferably closed, except in the direction of flow. Thus a liquid introduced into the channel will be able to flow only along one axis—lengthways, and not up/down or sideways—although the direction of flow along that axis may change (forwards/backwards).

In a device with a plurality of channels for analysing a plurality of cells, it is preferred to have channels that are substantially identical to each other (e.g. in terms of dimensions, material, immobilised reagent(s), etc.) such that, during use, cells are subjected to substantially the same treatment and analysis, allowing direct comparison of results. It is preferred that all analysis channels are substantially identical.

In some embodiments of the invention, a channel can branch (e.g. FIG. 25) into two or more sub-channels. Contents may pass into each branch. Each branch can be arranged to receive substantially the same materials as the others, or different cell contents can be directed down different branches e.g. mRNA down one branch and DNA down another, or positively charged proteins down one branch and negatively charged proteins down the other. The sub-channels may or may not re-join i.e. a branched channel can have more than one output end for a single input end.

Branching can also be used in another way. A cell's contents can be separated in a first dimension, and can progress to a 'T junction' branch. If the two branches have opposite polarities then proteins and RNA, which in general have different charges, can flow down different branches, thus permitting proteomic analysis on one branch and genomic analysis on the other branch (FIG. 31).

In addition to analysis channels, a device can include further channels which are not used for analysis e.g. for reagent delivery or movement, or unused channels.

Analytical Components within the Channels

The channels in the device are for the analysis of a cell's contents, and they include analytical components that can interact with the cell's contents to give analytical results. The analytical components in any given device will generally be chosen based on knowledge of the cell of interest in order to give analytical data of interest.

Typical analytical components that can be situated within a channel include, but are not limited to: chromatographic separation media; electrophoretic separation media; immobilised binding reagents; etc. Reagents that have been used in chemical cytometry [2] can also be included. Preferred analytical components are immobilised binding reagents, such as nucleic acids for hybridisation, antibodies for antigen binding, antigens for antibody binding, lectins for capturing sugars and/or glycoproteins, etc. Preferred binding reagents are specific for a chosen target e.g. a nucleic acid sequence for specifically hybridising to a target of interest, an antibody for specifically binding a target antigen of interest. The degree of specificity can vary according to the needs of an individual experiment e.g. in some experiments it may be desirable to capture a target with nucleotide mismatch(es) relative to an immobilised sequence, but other experiments may require absolute stringency.

Analytical reagents are preferably immobilised along only one side of a channel. In a channel with a rectangular cross-section, a reagents will typically be located on only one of the four walls, and preferably on one of the long walls.

Different immobilised binding reagents are preferably arranged in discrete cells or patches, to facilitate data analysis—if different reagents are located within the same patch then it will not be clear which of the reagents gives rise to a signal. It is possible, however, for neighbouring patches to overlap slightly, or not to have tight boundaries, provided that the signal arising from one immobilised reagent can be distinguished from the signal arising from a different immobilised reagent.

Preferred channels include a series of different immobilised nucleic acids for hybridising to specific nucleic acids within a cell's contents. The sequence of the nucleic acids will be chosen according to the targets of interest. More preferably, the analytical components retain specific mRNA transcripts. The immobilised nucleic acids are preferably DNA, are preferably single-stranded, and are preferably oligonucleotides (e.g. shorter than 200 nucleotides, <150 nt, <100 nt, <50 nt, or shorter). Retention of mRNA rather than DNA can conveniently be achieved by removing DNA before analysis.

Other preferred channels include a series of different immobilised reagents for capturing proteins. These will typically be immunochemical reagents, such as antibodies, although other specific binding reagents can also be used e.g. receptors for capturing protein ligands and vice versa. Techniques for the specific capture of proteins by immobilising reagents to solid surfaces are well known in the art e.g. from ELISA, surface plasmon resonance, protein arrays, antibody arrays, etc. Antibody arrays for analysing blood (e.g. by specific capture and analysis of cytokines and intracellular signalling proteins) are already available [29] (e.g. the TranSignal™ Cytokine Antibody Arrays from Panomics [30]), and electrochemical enzyme immunoassays based on immobilised capture antibodies have been reported with a sensitivity of 10 pg/ml [31]. To detect binding in an immunochemical assay format then it is typically necessary to use a second antibody (a 'sandwich' assay).

A single channel can include reagents for analysing both nucleic acids and proteins.

Methods for immobilising analytical reagents onto surfaces are well known in the art. Methods for attaching nucleic acids to surfaces in a hybridisable format are known from the microarray field e.g. attachment via linkers, to a matrix on the surface, to a gel on the surface, etc. The best-known method is the photolithographic masking method used by Affymetrix for in situ synthesis of nucleotide probes on a glass surface, but electrochemical in situ synthesis methods are also known, as are inkjet deposition methods. Methods for attaching proteins (particularly antibodies) to surfaces are similarly known. These methods have been applied at the scale appropriate for single cell analysis.

Immobilised nucleic acids can be pre-synthesised and then attached to a surface, or can be synthesised in situ on a surface by delivering precursors to a growing nucleic acid chain. Either of these methods can be used according to the invention.

Preferred immobilised nucleic acids are formed by in situ synthesis using electrochemical deprotection of a growing nucleic acid chain, as described in references 32, 33 & 34.

One analytical procedure used with the invention involves capture of mRNA within the channel by hybridisation to an immobilised capture DNA, followed by reverse transcription of the mRNA using the immobilised and hybridised DNA as a primer. In this procedure, therefore, a reverse transcriptase has to be present within the channel, and this can be introduced into the channel together with dNTPs and other reagents after mRNA has been immobilised. The reverse transcription process extends the immobilised primer to synthesise an immobilised cDNA and thus leads to covalent modification of the device of the invention. Further details of this technique are given below. The capture DNA will generally have two portions: a poly-T portion that allows mRNA-specific capture and second portion for sequence-specific hybridisation to a target of choice.

In order to facilitate chain extension of a DNA on the device by reverse transcription, it will be immobilised via its 5' end or via an internal nucleotide, such that it has a free 3' end.

Devices preferably contain at least $10^N$ different analytical reagents, wherein N is selected from 0, 1, 2, 3, 4, 5, 6, 7, 8 or more. Immobilisation of at least 106 different oligonucleotides onto a single surface is well known in the field of microarrays. The $10^N$ different reagents will typically be arranged in $10^N$ different patches.

Each patch of immobilised reagent preferably has an area of less than $10 \times m^2$, where X is selected from −6, −7, −8, −9, −10, −11, −12, etc. Microarrays with patch sizes in the order of 10 μm×10 μm (i.e. $10^{-10}$ m²) are readily prepared using current technology. Patches with a small area improve the sensitivity of detection. When materials bind to the immobilised analysis reagent they are confined to a small area, increasing signal to noise ratio.

The centre-to-centre separation of patches is preferably less than $10^Y$m, where Y is selected from −3, −4, −5, etc. Adjacent patches may abut or may overlap, but it is preferred that adjacent patches are separated by a gap. Overlapping patches are not preferred.

Patches preferably have a rectangular or square shape. For a channel with width W and area A, the length of such a patch will thus be A÷W. For abutting patches of the same size, the centre-to-centre separation will be A÷W, and to allow a gap between patches then the centre-to-centre separation will more typically at least 1.5(A÷W) or 2(A÷W).

Patches are preferably arranged such that they are encountered singly in series along the direction of movement of a cell's contents, as illustrated in FIG. 11. Thus neighbouring patches will preferably be arranged along the direction of movement (lengthways), and not along the perpendicular direction (widthways).

Similarly, patches are preferably arranged such that they occupy the full width of a channel (FIG. 12). This minimises the potential for a rare analyte to progress through the channel without encountering the patch.

In a device with a plurality of channels for analysing a plurality of cells, it is preferred that the selection, series and amount of immobilised reagent(s) along each channel should be substantially identical such that, during use, each cell is subjected to substantially the same treatment and analysis, allowing direct comparison of results. Further details of this aspect of the invention are given below.

In a preferred device, comprising a plurality of channels and a plurality of immobilised analysis reagents, the channels are straight and are substantially parallel to each other, and the analysis reagents are immobilised in straight lines that run substantially orthogonal to the channels (see also ref. 34). See FIG. 13. This arrangement, discussed further below, ensures that the patches occupy the full width of the channels, and that all channels contain the same series of analysis reagents.

Thus the invention provides a device comprising: (a) a plurality of channels; and (b) a plurality of immobilised analysis reagents, wherein: (c) the channels are substantially parallel to each other; and (d) an immobilised analysis reagent is arranged in a line running orthogonal to the channels. The channels preferably have an input end and an output end, and, as described above, the input end is adapted such that an intact cell of interest cannot enter the channel.

Because channels are preferably closed, except along their length, access to their internal surfaces cannot easily be performed, which has an impact on the methods used for attachment of analysis reagents. Preferred devices are assembled from a base member and a lid member. The base member includes channels with an open upper side, allowing access to the channel's internal surfaces. After reagents have been immobilised onto the base member the lid member is attached to close the channel's upper side (FIG. 16). The lid and base members will join to seal the channel, to prevent materials leaking between channels. In an alternative arrangement, reagents are applied to the lid rather than to the base. Where the lid covers the channel, it may be flat. In an alternative arrangement, the lid may itself include part of the channel (FIG. 17). Preferred base members are made from PDMS, and preferred lids are made from glass.

Analysing Results

The detection methods used to analyse results depend on the nature of the molecular targets and on any label that may be used. They may also depend on the strength of the signal at a given analysis site, as explained in more detail below. Quantitative detection methods are preferred.

Detection may occur in situ within the device or may occur in a disassembled device. For instance, in a device having a channel member and a lid member (see above), with capture reagents immobilised on the lid member, the lid can be removed after analytes have passed through the channels, and the lid can be analysed separately e.g. using the reagents, techniques, devices and software already used to analyse microarrays.

For the preferred analyses (RNA and protein), further biochemical processing may be needed in order to introduce detectable labels after a target analyte has interacted with an immobilised binding reagent. Fluorescent labels are preferred for use with the invention.

Fluorescence in the channels can be excited using an evanescent wave. These waves extend out of the surface of a material by ~½ of the wavelength of the illuminating light i.e. they will extend outwards by ~150-350 nm, which is more than enough to extend illumination throughout a patch of immobilised oligonucleotides. Other sources of light for excitation can also be used e.g. lasers, lamps, LEDs, etc.

Proteins can be detected by one of several known methods that exploit antibodies. For example, a protein that has been captured by an immobilised antibody can be detected by applying a second labelled antibody specific for a different epitope from the first antibody, to form a 'sandwich' complex.

For RNA analytes, detection can be achieved by incorporating fluorescent nucleotides into a complementary strand using an enzyme such as reverse transcriptase. cDNA may be made from mRNA in a solution reaction within the area where the cells are lysed or in the expansion chamber, by introducing nucleotide precursors and RT. An alternative is to hybridise the mRNA to the oligonucleotide probes and to synthesise cDNA in situ using the immobilised probe as a primer. The reverse transcription reaction preferably incorporates labelled nucleotides into the cDNA in order to facilitate detection of the hybridisation [35]. This can be achieved by the use of dNTPs with suitable fluorophores attached. Unlike a sequencing reaction, it is not necessary to use different coloured fluorophores for different nucleotides, because individual nucleotides do not need to be distinguished. Similarly, there is no need to label every nucleotide, and so 1, 2, 3 or 4 of dATP, dCTP, dGTP and dTTP may be labelled, and a mixture of labelled and unlabelled dNTPs can be used. Incorporation of a large number of fluorophores into the cDNA (e.g. in at least 5% of incorporated dNTPs, such as ≧10%, ≧20%, ≧30%, ≧40%, ≧50%, ≧75%, or more) means that the cDNA can readily be detected within the channel by any of the familiar means of fluorescence detection, thereby revealing a positive signal even for a single hybridisation event. Thus even low-abundance mRNAs can be detected.

Rather than incorporate fluorophores directly, it is also possible to incorporate a specific functional group to which fluorophores can later be coupled ('post-labeling') e.g. after steps such as reverse transcription, washing, etc.

As mentioned above, the detection methods used to analyse results may depend on the strength of the signal at a given analysis site. Taking a patch of immobilised oligoDNA as an example, which has been extended using fluorescently labelled dNTPs using a hybridised mRNA transcript as the template, a different detection technique may be used depending on whether the signal on the patch is strong or weak: for a strong signal then integration of total signal from the whole patch can be used, with the strength of signal being proportional to the number of hybrids (and thus proportional to the number of transcripts in the original cell); for a weak signal, however, integration of total signal can be inappropriate, and so is not suitable for quantitative analysis, particularly for low abundance transcripts. The main difference between the strong and weak signals is the signal/noise ratio: for a strong signal then the noise has little effect, but noise can obscure quantitative analysis of a weak signal.

For example, with human mRNAs of moderate to high abundance then a 10 μm×10 μm patch will generally capture enough signal for integration to suffice, and there will be enough fluorescent signal to allow accurate measurement if most of the RNA is captured. This size of a patch is approximately the same as a mammalian cell, and it is well known that mRNAs of moderate abundance can be detected by in situ hybridisation when probed with fluorescent cDNA; e.g. FISH methods are available for detecting as few as 50-60 transcripts in a cell. For less abundant mRNAs, however, the integrated signal generated by a photomultiplier or a conventional CCD array is unsuitable.

For example, an average transcript is about 300 nm long (1000 nucleotides; 10 nucleotides every 3 nm), and its diameter is about 1 nm. The "area" of a transcript is thus $0.3 \times 0.001$ $\mu m = 3 \times 10^{-4}$ $\mu m^2$. A 10 μm×10 μm (110 μm$^2$) patch can thus accommodate a maximum of $100/3 \times 10^{-4}$ transcripts, which is $3.3 \times 10^5$ transcripts per patch. As the dynamic range for conventional fluorescence detection is around $10^4$, even if the full area of a RNA transcript is exposed for detection (e.g. by the flow embodiment described above and illustrated in FIG. 29) then at least 30 transcripts would be needed for detection. Thus transcripts present at fewer than ~50 per cell cannot be detected by conventional detection means.

Sensitive techniques are available for detection of single fluorophores [36,37], however, and so detection of an individual cDNA/mRNA hybrid containing multiple fluorophores is well within current technological capabilities. Current apparatuses that can identify single fluorophores have a pixel resolution of ~150 nm. For example, references 38 & 39 describe a single molecule reader (commercially available as the 'CytoScout' from Upper Austrian Research GmbH) in which a CCD detector is synchronized with the movement of a sample scanning stage, enabling continuous data acquisition to collect data from an area 5 mm×5 mm within 11 minutes at a pixel size of 129 nm. As described in more detail below, the fluorescent signal from a single nucleic acid can extend over a 300 nm length, and so can be distinguished from background using current technology. These signals can be counted, with the total number of signals corresponding to the total number of transcripts.

Rather than analyse a patch as a whole, however, signals can be counted by high resolution scanning of the patch. For instance, a laser spot (200-300 nm diameter) can illuminate a precisely-controlled path along a patch (FIG. 28) and fluorescence can be counted as the spot progresses, without suffering from the same signal/noise ratio as when detecting total fluorescence for the patch as described above. In general, the individual fluorescence spots will be smaller than the illuminating laser spot. For detection, a cooled CCD or photomultiplier tube or other means may be used to measure the low light intensity of the fluorescent emission. Counting of spots can be performed for the total patch area; as an alternative, counting can continue until a specific number of spots has been located, and the area scanned up to that point can then be compared to the patch's total area and the total count for the whole patch can be estimated by extrapolation.

Sensitivity of this detection method can be further improved by using the serial in situ reverse transcription method described in more detail below.

For abundant transcripts, however, single molecules cannot be distinguished in the crowded field. A patch of area of 10 μm×10 μm is equivalent to ~3-4,000 pixels in the single fluorophore detector described above. It is not possible to count individual signals if more than a few hundred occupy this area, as it is necessary to have empty space around a signal in order for it to be counted (i.e. 1 'on' pixel surrounded by 8 'off' pixels in a square arrangement). However, there is no difficulty in measuring the amount of captured molecules using a conventional microarray reader, or a confocal microscope with a scanning stage adapted to scan integrate pixel intensities. Thus scanners that are already used to analyse microarrays can be used. Suitable analysers for use with flow channels are already incorporated in equipment that is readily available e.g. in the Agilent Bioanalyzer.

At intermediate densities, where it is possible to identify empty spaces in the image, but the density is such that there is high probability of multiple occupancy of a pixel, statistical methods can be used to compute the most likely number of molecules from the density of objects in the image.

Thus data can be collected in various ways. With abundant analytes, each pixel in a CCD dataset has an intensity proportional to the number of fluorophores (and thus analytes) present; with rarer analytes, data will typically be analysed by counting the number of pixels where a fluorescent signal is present, with each 'on' pixel representing a single analyte. The method used to measure signal can combine these various approaches, thus attaining a substantial extension of the dynamic range of the measurement—standard integration methods in some cases and counting methods in others. At low signal intensities the dynamic range can be increased 100-fold and, surprisingly, a 10-fold increase in dynamic range is also possible at high signal intensities.

The device of the invention can also be interfaced with a mass spectrometer. For example, a channel's output end could feed directly into an electrospray ionisation spectrometer, for MS analysis of cellular contents as they emerge from the analysis channel. Integration of microfluidic devices with MS is known e.g. reference 40 describes a microfluidic chip for peptide analysis with an integrated HPLC column, sample enrichment column, and nanoelectrospray tip, and this 'HPLC-Chip/MS Technology' is available from Agilent.

A device may include a laser source and/or an in-line laser detector. The laser can shine through multiple channels, and light deflected upwards can be read by a detector above the channels. The laser can be used to excite molecules as they pass through its path in a channel, or as they emerge from a channel's output end.

A major advantage of the invention is its capacity to analyse the contents of a cell even though the analytes can range from zero to many thousand copies per cell. As mentioned above, the invention provides improvements in fluorescence detection where signal strengths span several orders of magnitude, and one aspect of the invention is an integrated fluorescence detector for implementing this method. Thus the invention provides an apparatus for detection of fluorescence on a reaction substrate, comprising a light source, a fluorescence detector, a receptacle for a substrate of interest, and a computer programmed to select between an integrating detection mode and a counting detection mode. The light source will typically be a laser. The fluorescence detector will typically be a fluorescence microscope. The substrate of interest will typically be a device of the invention, or a portion thereof (e.g. a lid member). Selection between integrating and counting modes may be made manually, but is preferably made automatically depending on one or more pre-selected criteria e.g. signal intensity, etc. The apparatus will usually be able to move the substrate, the light source and/or the detector relative to each other e.g. in a way that is adapted to the specific format of the substrate and the disposition of the probes. For example, ignoring the empty regions between lines of probes will speed up the reading process.

The fluorescence being detected preferably results from specific binding of two biological molecules e.g. two nucleic acids, an antibody & antigen, etc.

When analysing results in a single channel, this apparatus can operate in various ways. For instance, it can move along the channel scanning individual patches in an integration mode, and then return to patches that did not reach a signal threshold in order to analyse them in a counting mode. As an alternative, it can make this selection at each patch along the channel, rather than making a crude 'first sweep' and requiring a second measurement of some patches. Similarly, the apparatus can operate in either of these ways, but scanning orthogonally to the channels. Further variations will be apparent.

Common Analytical Components

As mentioned above, a powerful aspect of the invention is to perform identical individual analysis in parallel on different cells, and the invention provides a device for individually analysing a plurality of cells, comprising a plurality of channels, each of which is for receiving the contents of an individual cell, wherein each channel contains a series of sequential analytical components along the channel, and wherein the sequence of analytical components in one channel is the same as in another channel.

Thus a cell will experience a common series (e.g. A, B, C, D, E, F, G, ...) of analytical components regardless of which channel it enters. This common arrangement of analytical components within multiple channels means that each cell being analysed experiences the same analytical reagents, meaning that the results for one cell can readily and directly be compared to the results for another cell.

Preferably, at least 10 (e.g. 10, 50, 100, 250, 500, 1000 or more) analysis channels, and more preferably all of the analysis channels, contain a common sequence of analytical components.

Preferably the common series of analytical components has the same composition and spatial arrangement in each of the channels (e.g. all patches of immobilised reagent have substantially the same size, spacing, position, reagent concentration, etc. as each other). Thus the results from multiple channels can readily be aligned with each other. For instance, if all channels are parallel straight lines, and if the first analytical components of all channels are aligned (e.g. FIG. 13), a straight line running perpendicular to the channels will cross the same analytical component in each of the channels. A detector running in a straight line perpendicular to and above the channels will therefore be able to scan in turn the results of the same single analytical test for each cell. It can then move along the direction of the channels to the position of the next analytical component and can repeat the straight line scan to obtain the results of the next single analytical test, etc.

Although each channel may have a common series of analytical components, this does not mean that all of the contents of each channel must be identical. For instance, two channels might have different components upstream of the first member of the common series (e.g. a unique component that can be used to identify the particular channel). Similarly, individual members of the common series of components may be separated by non-common components, but the common series will be found in each channel, regardless of any other components. For instance, FIG. 26 shows an arrangement of seven analytical components per channel, with four common components.

A common series of immobilised binding reagents is particularly preferred.

If a device includes branched channels that are designed to receive different types of material (e.g. one branch for DNA, one branch for mRNA) then a common series in a branched region will generally apply to only one branch per channel e.g. all of the DNA sub-channels have a common series, but the same common series is not seen in the mRNA sub-channels. The advantage of linear scanning parallel to the channels is still manifested in the branched arrangement, but as the detector moves from one channel to the next then it will see two sub-channels.

Moving Cell Contents Through the Device

After a cell's contents have been released, they pass into a channel for analysis. They enter at the input end of a channel and move along the channel towards the output end. In some situations it may be desired to reverse the direction of movement after the contents have entered a channel, but at least the initial movement will be from input end to output end.

Various techniques can be used to move a cell's contents along the channel e.g. based on pumping, suction, electrokinesis, etc. Preferred techniques move the cell's contents electrokinetically (e.g. by electroosmosis or by electrophoresis) and require a potential to be applied across the channel, with the polarity dictating the direction of movement. Electrokinetic movement in microfabricated devices is reviewed in reference 41. When electrophoresis is used within the context of this invention, it will usually be for moving material through the device rather than for separating molecules from each other based on their mobility.

Electroosmosis is a process by which fluid flows through a charged channel when a potential is applied across the channel. If a channel's surface is positively charged (e.g. along one or more walls) then, when a potential is applied across the channel, fluid within the channel can move by electroosmosis towards the anode. See FIG. 4. Movement of bulk fluid can bring about movement of things within the fluid e.g. of cells, of components in suspension, of dissolved material, etc.

Electrophoresis is a process by which charged particles move within an electric field. Cells are generally negatively charged at neutral pH and so will move by electrophoresis towards an anode. Electrophoresis within the device can take place in an open channel, or can take place in a gel or viscous material situated within the channel.

Electroosmosis and electrophoresis can be experienced at the same time. For instance, a negatively charged mRNA molecule will move towards an anode by electrophoresis. If a channel's walls are positively charged then fluid movement within the channel will also be towards the anode, and so the mRNA will move towards the anode by both electroosmosis and electrophoresis. If a channel's walls are negatively charged, however, the mRNA will experience electroosmotic flow towards the cathode, which will oppose the electrophoretic flow. The net effect of the opposing electroosmotic and electrophoretic flows on mRNA movement will depend on factors such as the magnitude of the electric field, the charge on the channel's walls, the solvent being used (e.g. depending on viscosity), the temperature (again, viscosity can change), ionic strength, presence of surfactants, pH, etc. These factors can be varied during design of the device (e.g.

choice of materials, etc.) and/or during use (e.g. choice of temperature, electric field, etc.) in order to achieve the desired movement of particular components. Alteration of pH during use is a preferred way of controlling movement.

Electroosmotic movement of material through the device is preferred. Movement of mRNA through the device is advantageously achieved by having (a) a negative potential at the input end relative to the output end (cathode at input side, anode at output side) and (b) a positive charge on the channel wall(s). Charged walls can be achieved by using a positively charged material for their manufacture.

As nucleic acids are charged molecules then they can cause changes in electroosmotic properties when immobilised on channel walls. If required then, in such situations, uncharged analogs of nucleic acids can be used instead e.g. PNA.

Electrokinetic movement can be controlled precisely, and movement speed and direction can be varied simply by varying the potential as required. Electrokinetic movement can also be stopped, which can be used e.g. to allow introduction of reagents by mechanical means (e.g. injection, pumping, etc.).

At a voltage gradient of 20 V/cm, DNA travels at 125 μm/s in a microchannel [42]. A suitable rate of transfer for nucleic acids over a linear array of nucleic acid patches would thus be at around 2 V/cm.

Advantageously, nucleic acids (with their phosphodiester backbone) are negatively charged at low pH where most proteins are positively charged. Under low pH, therefore, most proteins move towards a cathode while nucleic acids move towards an anode. Using an electric field with appropriate polarity thus allows proteins and nucleic acids to be separated from each other, thereby facilitating the analysis of one without interference from the other. The channel arrangement in FIG. 31 facilitates this analysis (see further below).

Dielectrophoresis can also be used for moving analytes. Non-contact cell-trapping using this technique has been reported [11], although field geometry can be difficult to optimise. Reference 43 uses an image-driven dielectrophoresis technique to perform high resolution patterning of electric fields on a photoconductive surface for manipulating single cells.

As mentioned above, in some situations it may be useful to move cell contents within a channel in both forwards and backwards directions. For sensitive detection of low abundance molecules within a cell then it is useful to capture for analysis as many of those molecules as possible. If material is moved one way and then the other then it can pass a particular binding reagent twice, thereby offering a second chance to capture any molecules that avoided capture on the first pass.

The ability to reverse bulk fluid movement within a channel also offers advantages in relation to avoidance of background noise and non-specific binding. As shown in FIG. 29, when the flow direction is reversed then the position of a specifically-hybridised nucleic acid molecule is shifted relative to its point of attachment, and a high resolution detector can detect this change. In contrast, the non-specifically-bound signal is not affected by the change in fluid movement. By comparing signals obtained with forward and reverse flow, therefore, specific binding can be distinguished from non-specific binding. The same effect can be achieved by stretching the attached nucleic acid molecule in an electric field; reversal of polarity will shift the position of the tethered nucleic acid, but will not shift non-specifically bound noise.

Thus the invention provides a method for analysing the results of a nucleic acid hybridisation assay arising from interaction between (i) a nucleic acid immobilised on a hybridisation substrate and (ii) a free nucleic acid, wherein the immobilised nucleic acid and/or the free nucleic acid includes a detectable label, and wherein the method comprises the steps of: (i) obtaining a first image of the hybridisation substrate, under conditions where liquid is flowing over, or an electric field is applied across, the substrate in a first direction; (ii) obtaining a second image of the hybridisation substrate, under conditions where liquid is flowing over, or an electric field is applied across, the substrate in a second direction; and (iii) comparing the first and second images. A detectable label which is aligned with the first direction in the first image and with the second direction in the second image represents a specific hybridisation signal; a detectable label which shows no such alignment represents experimental noise or a non-specific hybridisation signal. The first and second directions are preferably in substantially the same plane, and the smaller angle between the two directions in that plane (i.e. as seen from above, for measurement purposes) will generally be $\geq 45°$, preferably $\geq 90°$, more preferably $\geq 135°$, and most preferably will be about 180° (i.e. reversal of flow or field). The change in flow or field direction can readily be achieved by changing the electrical polarity of a channel, such that the direction of electrokinetic movement is reversed. Comparison of the first and second images will typically be performed by a computer.

In a development of this method, two labels with distinguishable signals are used, one being an early label and one being a late label. As chain extension occurs, initial extension will use the early label and later extension will use the late label. When the direction of flow changes then specific hybrids will exhibit a change in the relative positions of the early and late labels. One way of introducing the labels is to initially provide only a subset of the four nucleotide precursors. Chain extension will proceed until a 'missing' nucleotide is required. The missing nucleotide(s) can then be provided, permitting further chain extension, with incorporation of a different detectable label. Thus a nucleic acid chain could, for instance, have a red 5' region and a green 3' region, and the relative positions of the red and green regions in a specific hybrid will change with flow direction. Having different detectable labels along a linear nucleic acid chain thus facilitates detection of a reverse in direction.

Taking 1000 nt as an average length for a transcript, and about 10 nucleotides per 3 nm of RNA, an average transcript is about 300 nm long. Apparatuses capable of identifying single fluorophore molecules are available, and these have a pixel resolution limit of ~150 nm [38]. Reverse transcription of a captured mRNA molecule using fluorescent dNTP substrates incorporates multiple (e.g. >100) fluorophores into the cDNA. By elongating the molecule by liquid flow as described above (or by using an electric field) then the signal will extend over up to 300 nm length, with a relatively intense fluorescence signal. The intense fluorescence will thus occupy more than one pixel in the detector, allowing it to be distinguished from background.

Non-specific binding to nucleic acid arrays can also be distinguished by analysis of its hybridisation kinetics, as described in reference 44.

Cells to be Analysed

The invention is suitable for the analysis of various cells, including both eukaryotic cells and prokaryotic cells. The invention is particularly suitable for analysing a plurality of cells which, although of the same type, are asynchronous i.e. at different stages of the cell cycle.

The invention can be used to analyse prokaryotic cells, such as bacteria, including, but not limited to: *E. coli; B. subtilis; N. meningitidis; N. gonorrhoeae; S. pneumoniae; S.*

*mutans; S. agalactiae; S. pyogenes; P. aeruginosa; H. pylori; M. catarrhalis; H. influenzae; B. pertussis; C. diphtheriae; C. tetani;* etc.

Within the eukaryotes, the invention can be used to analyse animal cells, plant cells, fungi cells (particularly yeasts), etc. Preferred animal cells of interest are mammalian cells. Preferred mammals are primates, including humans.

Specific cell types of interest, particularly for human cells, include but are not limited to: blood cells, such as lymphocytes, natural killer cells, leukocytes, neutrophils, monocytes platelets, etc.; tumour cells, such as carcinomas, lymphomas, leukemic cells; gametes, including ova and spermatozoa; heart cells; kidney cells; pancreas cells; liver cells; brain cells; skin cells; stem cells, including adult stem cells and embryonic stem cells; etc. Cell lines can also be analysed. The invention is particularly useful for studying stem cells. The ability to subject individual cells to different treatments prior to individual analysis in separate channels is particularly useful for cells such as stem cells e.g. separate cells can be treated with different stimuli (growth factors, etc.), either in situ (e.g. by supplying stimuli through a reagent supply line) or before entering the device, and the effect on gene and/or protein expression can be analysed.

From a practical standpoint, it is easier to separate and capture cells which are in free suspension, such as unicellular organisms or circulating cells from animals. Often, however, the cells of interest will not naturally be separated in this way. In such cases, however, methods for preparing cell suspensions are well known from techniques applied to FACS.

The invention is used to analyse the contents of these cells. This does not mean that the invention must be used to analyse total cell contents e.g. as described above, unwanted materials can be removed prior to analysis. Nor must total cell contents be removed from the cell e.g. only particular fractions need to be removed, and only a partial extract need be taken. In general, however, the invention will involve cell lysis to release total cell contents, and analysis will be performed on at least mRNA transcripts and/or proteins from the cell.

It may be advantageous to treat a population of cells prior to introducing them to the device of the invention. For example, cells may be separated into fractions e.g. based on size, cell markers, etc. Separation can be achieved by a number of methods known in the art. A particularly favourable method is fluorescence activated cell sorting (FACS). Methods have been developed for FACS in so-called 'lab-on-a-chip' devices [8], and such a device could readily be incorporated into and utilised with the present invention. It could be advantageous to stain the cells in order to identify specific types. For example, the cells could be stained with fluorescent antibodies to cell surface markers, before or after they are introduced into the device. If the antibodies are used after the cells enter the device then they can bind to cells before or after they have become immobilised in the apparatus, allowing the cell associated with each microchannel to be characterised.

For certain applications, it would be advantageous to prefractionate the cells according to size prior to feeding them to the apparatus, so that different sizes of channels could be used to analyse cells of different sizes. Cells can be prefractionated according to size by directing a cell suspension through a system of sieves before the buffer stream arrives at the system of funnels and channels (FIG. 22). Methods for extracting single cells from larger cell masses are disclosed in reference 45.

There are a number of ways to introduce cells into devices of the invention. In most cases, the cells will be suspended in a buffer solution e.g. to ensure that they retain their integrity, and a characteristic size and shape. The suspension may be applied to a receptacle that feeds into the delivery line. The dimensions of the delivery line will be such that the cells are free to travel in the buffer flow or under the influence of an electric field. The flow-path of the carrier solution or the electric field runs from the delivery line and through the channels. Hence the cells travel through the delivery line and are then directed into cell trapping sites funnels which then lead into the channels.

Cells can enter the device direct from other cell separating apparatuses e.g. from a cell sorter such as a MACS or FACS device, from a cell fractionation column such as those used to separate red and white blood cells, etc.

Observation of Cells

When it is desired to observe cells within a device, a microscope will usually be used. Because of the small optical contrast with respect to the buffer and typical microfluidic structures, it may be desirable to use contrast enhancement e.g. using techniques such as phase contrast microscopy, differential interference contrast microscopy, fluorescence microscopy, etc. In many cases, however, a conventional light microscope can be used.

In a simple embodiment, detection uses a long working distance microscope objective. In some configurations, in particular when the channels are deep, a telecentric microscope objective may be used in order to avoid both the casting of shadows and parallax errors. It is desirable to use a tube lens with zoom in order to have flexibility in selecting the field of view without the need to change microscope objectives. The microscope may have a camera port to which a camera can be attached. When the contrast in the images is low, the use of a camera with an enhanced bit-depth such as 10 bit per pixel, 12 bit per pixel, or more, can be desirable.

If transmission microscopy is possible in the chosen sample geometry, this is the preferred configuration. A white light source will usually be shone through the sample, but in some configurations coloured light (either filtered or from a coloured light source such as from an light emitting diode (LED)) may be advantageous.

In the case of reflection microscopy, it is desirable to coat the back side of the sample with a reflective surface such as a metal, or by supporting the microfluidic structure on reflective surface such as a mirror, a silicon wafer, etc. In a preferred embodiment, the incident light is coaxial with the optical axis of the microscope in order to avoid casting shadows, but in some configurations ring-light or dark-field illumination may enhance the contrast in the images as well.

Conventional methods for sample movement such as a positioning stage perpendicular to the optical axis, and methods for focusing the microscope, can be used.

Depending on the requirements of the experiment, the microscope may be operated manually (focus, positioning, selection of the field of view, etc.), or it can be fully automated. The images may be used for diagnostic purposes and fault detection (accidental capture of two cells, capture of contaminants, clogging of the structure with genomic DNA after premature cell lysis, etc.), as well as for documentation purposes. Image analysis may be used to distinguish between different captured cell types.

Laying Down Stripes of Analytical Reagents

As mentioned above, preferred devices comprise a plurality of channels and a plurality of immobilised analysis reagents, wherein (a) the channels are straight and are substantially parallel to each other, and (b) the analysis reagents are immobilised in straight lines that run substantially orthogonal to the channels. Such a device is illustrated in FIG. 13.

Various techniques can be used to immobilise reagents such as nucleic acids in a series of parallel straight stripes. These techniques will typically be used to prepare stripes on a support surface that will then be assembled with another component to give a device of the invention e.g. as shown in FIG. 46.

References 32 to 34 disclose methods for the in situ synthesis of nucleic acids using electrochemical deprotection of a growing chain. Such methods are particularly useful with the present invention. Where these methods use benzoquinones, one improvement is to include a washing step using aqueous hydrogen peroxide between reaction steps. It has been found that during acid generation, one of the intermediate species (a benzoquinone derivative) can sometimes form an insoluble complex with the cationic species (tetra(alkyl) ammonium) in the supporting electrolyte, and that this complex precipitates preferentially onto the cathodes. This precipitation gradually causes resistance of the electrodes to increase between reaction cycles. Hydrogen peroxide can be used to remove this complex and prevent the resistance increase e.g. using a mixture of 3% $H_2O_2$ in water. It is thought that the presence of an aqueous solution helps dissolving the ionic complex, whereas the presence of $H_2O_2$ helps re-oxidation of the partially reduced benzoquinone species.

Where platinum or iridium electrodes are used, a further improvement uses a keying layer in order to enhance adhesion of the electrodes to silicon. The keying layer is a thin layer (10-200 nm thick) of chromium or titanium. Care has to be taken that the keying layer is shielded from the electrolyte, as both chromium and titanium are electroactive and (a) prone to electrochemical dissolution during the current/acid generation step, (b) form a galvanic element with the noble electrode material (FIG. 63). During the fabrication, therefore, the edges of the electrodes are covered using a layer of insulating silicon dioxide. This also shields the keying layer from the electrolyte.

As an alternative to electrochemical methods, reference 46 discloses a method for forming a line of a reagent on a surface, comprising the steps of: (a) forming a contact between a reaction surface on a reaction substrate and an open microfluidic channel on a channel substrate; (b) introducing a reagent into the microfluidic channel such that the reagent contacts the reaction surface along a contact line formed by the contact between the reaction surface and the open microfluidic channel; and (c) separating the reaction surface and the microfluidic channel, leaving the reagent immobilised along the contact line on the reaction surface. This method can be used with the present invention.

This method can be used to guide nucleotide precursors down contact lines, to build up nucleic acids by in situ synthesis methods. As an alternative, however, it can be used to guide activated pre-synthesised nucleic acids down channels to allow them to interact with reactive sites on a substrate surface. By containing an activated nucleic acid within the microfluidic channels in contact with the reactive surface then it is possible to induce localised covalent attachment into areas defined by the channels. For example, a glass substrate with a reactive NHS-ester surface (e.g. the Schott Nexterion H product) can be combined with a structure defining parallel microfluidic channels, and then amino-modified nucleic acids can be passed down the channels. Each channel can receive a separate nucleic acid, thereby providing a substrate having stripes of immobilised nucleic acids. This procedure is illustrated in FIG. 64, where two different amino-labelled 70mers are passed along two parallel sealed channels over a reactive NHS-ester surface (pH>7.0).

Rather than use a physical barrier to separate stripes, selective activation can be used. For instance, the surface of a substrate can be activated with a photocleavable protecting group (e.g. NVOC [47]). Patches of stripes on this surface can be deprotected by using a suitable patterning mask, to leave a reactive group that can react with a pre-synthesised nucleic acid. Methods of this type using interference patterning are described in, for example, reference 48. By using an appropriate light source and optical workstation, stripes as narrow as 1 µm can be illuminated, resulting in closely packed oligonucleotide stripes.

Selective activation by electrochemical means can also be used to prepare stripes. References 32 to 34 and 49 disclose the generation of fine stripes of acid in an electrolyte. These methods can be used in combination with an acid-labile protecting group to selectively activate stripes on a support surface for subsequent attachment of nucleic acids.

While laying down stripes of analysis reagents, it is useful to utilise a gasket, particularly when using electrochemical methods. A gasket can separate the electrodes (that are being used to generate and/or confine the reactive substances) from the reaction substrate at a fixed distance (e.g. between 10-50 µm), and can also confine the reagents being used during synthesis by acting as a flow cell. It is therefore important that a gasket should not be attacked by any of the chemicals used during synthesis, and that it should forms a good seal. For instance, a gasket can be made from PTFE, cut from a sheet of PTFE using a die, which is then placed between the electrodes and the substrate. Alternatively, it can made photolithographically and permanently attached to the electrodes. Inert gaskets of 10-50 µm thickness can also be made using the photoresist SU8.

Dimensions and Parameters

The dimensions and parameters of the various features of the devices of the invention can be very important, but will vary according to particular needs and applications.

The input end of a channel is adapted such that an intact cell of interest cannot enter. This is generally achieved by having an aperture at the input end that is smaller than the cell's size. Typical cell dimensions are given in the following table, with some example organelle and virus sizes for comparison:

| Cell | Dimensions | Volume |
| --- | --- | --- |
| S. cerevisiae | 5 µm | 66 µm³ |
| S. pombe | 2 × 7 µm | 22 µm³ |
| Mammalian cell | 10-20 µm | 500-4,000 µm³ |
| Human T lymphocyte | 6-8 µm | |
| E. coli | 1 × 3 µm | 2 µm³ |
| Mammalian mitochondrion | 1 µm | 0.5 µm³ |
| Mammalian nucleus | 5-10 µm | 66-500 µm³ |
| Plant chloroplast | 1 × 4 µm | 3 µm³ |
| Bacteriophage λ | 50 nm (head only) | $6.6 \times 10^{-5}$ µm³ |
| Ribosome | 30 nm diameter | $1.4 \times 10^{-5}$ µm³ |
| Globular monomeric protein | 5 nm diameter | $6.6 \times 10^{-8}$ µm³ |

Depending on the cells to be analysed, therefore, the input end of a channel will typically have a width of between 1 µm and 50 µm, preferably between 2 µm and 20 µm.

The same size range characterises the smaller diameter of a tapered cell trapping site. The larger diameter of a taper will typically be in the range of 10 µm to 500 µm.

The cross-sectional area of a channel is preferably about the same as the area of the aperture i.e. it does not expand after the aperture.

Where present, an expansion chamber preferably increases the width of its input aperture at least 2-fold (e.g. at least 3-, 4-, 5-fold or more). It must be larger in volume than the cell contents being treated, but small enough that diffusion of the bolus of delivered treatment reagents diffuses quickly to interact with the cell contents. It should also be shaped to allow efficient mixing e.g. its surface may carry protrusions or baffles to stir the contents of the chamber if they are moved backwards and forwards by pulsating pressure waves.

Sensitive detection means are provided (e.g. see further below), but a target can be detected only if it has been captured. One aim of the invention is to capture as many target molecules (i.e. the analytes for which analytical components are provided in a channel) as possible, preferably at least 50% (e.g. ≧60%, ≧70%, ≧80%, ≧90%, ≧95%, ≧99%, or even 100%) of the mRNA targets within a cell, and typically substantially all of a particular target transcript. This is particularly important for rare transcripts. This aim has implications for various features of the device and its use e.g. the size of a capture patch, the density of nucleic acids within a patch, the dimensions of a channel, flow rate through the device, etc.

Taking a moving cross-section through the channel, at any given time a target can be located at any x,y position in the cross-section e.g. towards the top or bottom of the channel. If probes are attached only to the bottom of the channel then the region of the cross-section above the probes is unproductive at any particular point in time. It is therefore useful to reduce the height or a channel and increase the width, such that the capture reagents cover as much of the cross-section as possible. Preferably, therefore, the cross-sectional area of an analysis channel is rectangular. Having a rectangle rather than a square, with the long end as the base (h<w, FIG. 18), means that molecules travelling through the channel diffuse quickly to probes attached to the surface(s) of the channel base and/or walls. The ratio of h:w is preferably at least 1:2 e.g. 1:3, 1:4, 1:5, 1:6, etc. The height of a channel is preferably <50 μm (e.g. <40 μm, <30 μm, <20 μm, <10 μm, <5 μm, <2 μm, etc.). Moreover, having capture reagents on a flat base facilitates signal detection when compared to a curved base, particularly in relation to a detector arranged perpendicular to the base.

To further reduce the unproductive portion of a cross-section, capture reagents should cover as much of the cross-section as possible. Thus using nucleic acids immobilised solely as a monolayer on the base of the channel may be less preferred than using nucleic acids attached to linkers of different lengths e.g. to linkers with a range of lengths, thus allowing capture at various heights within the cross-section. A three-dimensional linker which extends into the cross-section and through which target can travel can also be used (e.g. polyacrylamide). Three-dimensional polymer pads have a capacity 100-1000 times greater than a monolayer of probe synthesized on glass, and this sort of arrangement is seen e.g. in references 50, 51, etc. In reference 51, oligonucleotides are attached to 20 μm-thick pads of polyacrylamide, each 40 μm×40 μm. If detection based on flow reversal if used (see above), however, only a single linker should be used per immobilised oligonucleotide, as cross-linking can mean that the change in alignment will not adequately take place. Longer linkers permit a greater shift in signal between the two directions.

The height of an analysis channel will generally be smaller than the height of any pre-trapping site channels e.g. of a delivery line.

The flow rate of material through the channel can also be controlled. If flow is too rapid then targets will be swept along without having chance to come into useful contact with a capture probe. With a slow enough flow rate then targets will be captured at the leading edge of a capture patch. Captured density is thus highest at the proximal edge of the patch and diminishes exponentially towards the distal edge. For instance, FIG. 30 shows the distribution of captured probes in a patch for three different flow rates. In all cases the capture is biased towards the leading edge of the patch, with the bias being greater at slower flow rates. This asymmetrical distribution of signal provides a number of advantages: sensitivity of detecting small amounts of target is enhanced by concentrating the capture to a confined area; the characteristic exponential decay helps distinguish true hybridisation signal from noise; and a uniform, high signal across the patch indicates that the probe has been saturated.

In a prototype device arranged as depicted in FIG. 13, channels are 10 μm wide and have a centre-to-centre separation of 50 μm. A 200-channel device will therefore be 1 cm wide. To keep a square device, the channels can be 1 cm long (or slightly shorter, to accommodate the size of the delivery line, trapping site, waste line, etc.). 500 different oligonucleotide stripes can be applied, each being 10 μm wide and having a centre-to-centre separation of 20 μm (i.e. 10 μm gap between stripes). A 1 cm$^2$ device can thus simultaneously analyse 500 different mRNA transcripts in 200 individual cells. Larger devices with narrower channels can analyse hundreds or thousands of cells in parallel, and can detect cells which occur at low frequency, mixed with a majority of other cells e.g. mitotic cells in a cycling population.

Each oligonucleotide patch has an area of 10 μm×10 μm on the channel's surface. With a channel height of 10 μm, a flow rate of 12.5 pl/sec is adequate to capture approximately 80% of a complementary RNA target in this 10 μm×10 μm patch.

As mentioned above, a 10 μm×10 μm oligonucleotide capture patch can accommodate in the order of $10^5$ transcripts per patch. Even superabundant transcripts would rarely (if ever) exceed $10^5$ per cell, and so a 10 μm×10 μm patch is adequate. If the patch decreases in area by 100-fold, however (e.g. 1 μm×1 μm) then only $10^3$ transcripts could be captured which would be inadequate for the most abundant transcripts. Thus the abundance of a particular target transcript can dictate the size of a capture patch. If a target is known to have a particularly high or low density then the size of the capture patch can be adjusted accordingly, and so patches within channels in devices of the invention need not all have the same size.

Serial In Situ Reverse Transcription

As mentioned above, a preferred procedure for analysing a cell's contents involves capture of mRNA within a channel by hybridisation to an immobilised capture DNA, followed by in situ reverse transcription of the mRNA to give a labelled cDNA, using the immobilised hybridised DNA as a primer. In combination with an appropriate detector (see above), this technique advantageously allows even rare transcripts to be detected. Transcripts can broadly be classified as superabundant, abundant and rare. Rough characteristics of each of these three classes are as follows:

|  | Super-abundant | Abundant | Rare |
| --- | --- | --- | --- |
| mRNA mass | 15-90% | 50-75% | <25% * |
| Contribution to RNA diversity | Negligible | <5% | 95% |
| No. structural gene transcripts | <10 | 200-1000 | Many |
| Transcripts per cell per sequence | >5000 | 500-2500 | 1-10 |
| Found in cell types | Highly specialised | Most | Most |
| Proteins visible by PAGE | Yes | Yes | No |

* Each transcript is <0.01% of total mRNA mass

The in situ reverse transcription method described above can be used to detect even these individual mRNA transcripts in the extract of a single cell, even though the extract may contain fewer than 10 of the transcripts. For rare transcripts (e.g. those present at fewer than 100 copies per cell, and particularly those with <10 copies/cell), where signal intensity will be very low, the invention provides an improved technique for improving the amount of detectable signal.

In this improved technique, repeated rounds of reverse transcription are performed. After a cDNA has been synthesised, the hybrid is melted (e.g. by heating) such that the mRNA is released. If the melting conditions are mild, however, or if they are quickly reversed (e.g. by cooling to below the $T_m$ of a polyA/polyT duplex), then the released mRNA can quickly re-anneal to a nearby non-extended primer (FIGS. 14A & 14B). Furthermore, if the immobilised nucleic acids are complementary to a portion of a mRNA's poly-A tail, the relatively-unstable rA-dT heteroduplex portion of the hybrid will melt at a temperature lower than that required to melt the rest of the molecule, constraining diffusion. Once the hybrid has been melted (in whole or in part) then re-annealing is frequent because non-extended primers are in large excess on the surface.

Thus a single mRNA molecule can be used as the template for the synthesis of multiple labelled cDNA molecules, and the cDNA products seeded by any single mRNA molecule will be in close proximity. A single labelled hybrid involving a low-abundance mRNA can therefore be amplified to give a more readily-detectable spot of label (FIG. 14C). The overall number of spots in a single patch is not increased, and so the quantitative nature of the assay is not lost, but the size of each labelled spot is amplified, facilitating hybrid detection. The fluorescent signal, measured conventionally, will increase in proportion to the degree of amplification. if amplification has been sufficient. The mRNAs may then be measured by counting the number of fluorescent spots in each oligonucleotide patch, as described above.

In order to achieve repeated rounds of reverse transcription in this way, a thermostable reverse transcriptase [52,53] can be used if heating is used to disrupt duplexes. Preferred reverse transcriptases used with the invention preferably have reduced RNase H activity.

This aspect of the invention can be performed separately from other aspects, and so the invention provides a process for performing a nucleic acid hybridisation assay, comprising the steps of: (i) providing a hybridisation substrate comprising immobilised nucleic acids; (ii) applying free nucleic acid to the hybridisation substrate under conditions that permit the free nucleic acid to form hybrids with the immobilised nucleic acids, wherein the free nucleic acid has a single-stranded overhang in the hybrid; (iii) extending the immobilised nucleic acid in the hybrid using the single-stranded overhang as a template, wherein the extension reaction incorporates a detectable label into the immobilised nucleic acid; (iv) melting at least a portion of the hybrid and allowing the melted portion to re-anneal to an immobilised nucleic acid, to form a new hybrid in which the free nucleic acid has a single-stranded overhang; and (v) repeating step (iii) at least n times, where n is an integer $\geq 1$, provided that where n>1 then step (iv) is performed after at least the first n−1 repeats of step (iii).

The hybridisation substrate used in step (i) can be a device as described herein, or can be a standard nucleic acid array as known in the art. The immobilised nucleic acids will generally be DNA.

The free nucleic acid applied in step (ii) can be DNA or RNA, and is preferably mRNA. Where it is mRNA then the immobilised nucleic acid may comprise a poly-T sequence e.g. a stretch of at least 10 (e.g. 20, 30, 40, 50 or more) consecutive T nucleotides. The poly-T sequence will be at or near the 5' end of the immobilised sequence.

Extension in step (iii) can be enzymatic or non-enzymatic, and can be achieved by polymerisation or ligation. Enzymatic polymerisation is preferred e.g. using a DNA polymerase (including both DNA-dependent DNA polymerases and RNA-dependent DNA polymerases i.e. reverse transcriptases), a RNA polymerase (including both DNA-dependent RNA polymerases and RNA-dependent RNA polymerases), etc. An appropriate enzyme will be chosen according to the primer being used (e.g. DNA or RNA) and the extension desired (e.g. DNA or RNA). The detectable label is preferably a fluorescent label.

In step (iv), nucleic acid hybrids are melted (at least in part) and re-annealed. After partial melting, the melted strand can re-anneal with a new primer in the vicinity of the previous hybrid. Full melting of an existing duplex can be used, but diffusion then interferes with re-annealing, and so partial melting is preferred e.g. melting of the portion of a hybrid that includes the polyA portion of a captured mRNA. The process is most advantageous where re-annealing takes place rapidly e.g. within $10^d$ seconds of the melting in step (iv), wherein d is selected from 0, −1, −2, −3, −4, −5 or less. Similarly, the re-annealing in step (iv) may take place (viewed from above) within $10^e$ meters of the previous hybrid, wherein e is selected from −4, −5, −6, −7, −8, −9 or less.

As specified in step (v), steps (iii) and (iv) can be repeated at least once, preferably at least twice, three times, etc. Thus n is preferably at least 2, 3, 4, 5, 10, 20, 30, 40, 50 or more. Each repeat of step (iii) is followed by step (iv), except that the final (i.e. the $n^{th}$) repeat does not have to be followed by step (iv). In many situations, however, even the nth repeat of step (iii) will be followed by a $n^{th}$ repeat of step (iv).

The invention also provides the modified hybridisation substrate obtained by this process.

The process may comprise the further step of (vi) detecting label on the modified hybridisation substrate.

Second Strand cDNA Synthesis

After in situ reverse transcription has been performed, there is initially a RNA/DNA hybrid, wherein the DNA will typically include a label for detection. In some embodiments of the invention, the RNA strand in this hybrid is removed e.g. using RNAse H. This removal step leaves a single-stranded DNA, which has been prepared by extension of an immobilised primer. After the removal step, this single-stranded cDNA can be used as the template for synthesis of the complementary cDNA strand, thereby giving double-stranded cDNA.

Synthesis of this second strand will be initiated using a primer that is complementary to the existing cDNA strand. After the initial reverse transcription, only DNA that had been extended as far as the location of this primer will be available for priming second strand synthesis. The second cDNA strand may also be synthesised to incorporate label, and the label can be the same as or different from the label used during synthesis of the first strand.

This technique is illustrated in FIG. 59, showing hybridisation to two immobilised oligo-DNA strands. In step (a), mRNA target hybridises to both strands. Reverse transcription takes place in step (b), but is complete for only one of the two oligo-DNA primers. The mRNA templates are removed in step (c), and then second strand primers are added in step (d). Only one of the extended immobilised DNAs can act as a template for the second strand synthesis.

Further Features

As well as analysing cellular contents, it may be preferred to analyse single organelles in eukaryotic cells, and particularly nuclei (e.g. for transcription factors), mitochondria and plastids (e.g. chloroplasts). Organelles can be prepared from cells prior to introducing them to the device of the invention, or they may be released from cells by lysis in situ. The organelles can then be further captured and treated in the same way as described above for whole cells. An arrangement for achieving this is shown in FIG. 19—a cell is trapped, its organelles are released, then the organelles are trapped while other material is washed away (a double-tapered trap). Isoelectric focusing of mitochondria is disclosed in ref. 22.

A similar cumulative-tapering setup is shown in FIG. 21 for removing large cells from a complex sample (e.g. a needle biopsy) and allowing small cells to reach the analysis channels, but this device becomes easily clogged. An alternative arrangement for separating cells based on size is shown in FIG. 22.

A delivery line may split cells into different fractions depending on size, and then the differently-sized cells can be directed to differently-sized cell trapping sites. Thus a single device can deal with a variety of differently-sized cells. A suitable size-fractionation arrangement is shown in FIG. 20.

Because devices of the invention have a very small scale, they can easily become blocked by contaminants such as dust. Filtration of samples prior to analysis is therefore preferred. A filter can be integral with the device of the invention or may be separate.

Once cells have been trapped, they may be examined under a microscope for features such as size and shape. For more detailed characterisation, they may be stained, for example with fluorescent antibodies, before microscopic examination. Such information is useful for association with molecular characterisation, the main objective of the invention.

General

The term "comprising" encompasses "including" as well as "consisting" e.g. a composition "comprising" X may consist exclusively of X or may include something additional e.g. X+Y.

The term "about" in relation to a numerical value x means, for example, x±10%. Where necessary, the term "about" can be omitted.

The word "substantially" does not exclude "completely" e.g. a composition which is "substantially free" from Y may be completely free from Y. Where necessary, the word "substantially" may be omitted from the definition of the invention.

The use of terms such as "diameter" and "circumference" in relation to an element does not necessarily imply that the element is circular (or, in a three-dimensional context, spherical).

The term "antibody" includes any of the various natural and artificial antibodies and antibody-derived proteins which are available, and their derivatives, e.g. including without limitation polyclonal antibodies, monoclonal antibodies, chimeric antibodies, humanized antibodies, human antibodies, single-domain antibodies, whole antibodies, antibody fragments such as F(ab')$_2$ and F(ab) fragments, Fv fragments (non-covalent heterodimers), single-chain antibodies such as single chain Fv molecules (scFv), minibodies, oligobodies, dimeric or trimeric antibody fragments or constructs, etc. The term "antibody" does not imply any particular origin, and includes antibodies obtained through non-conventional processes, such as phage display. Antibodies of the invention can be of any isotype (e.g. IgA, IgG, IgM i.e. an α, γ or μ heavy chain) and may have a κ or a λ light chain.

BRIEF DESCRIPTION OF THE DRAWINGS

FIG. 3 shows alternative arrangements for physically trapping cells.

FIG. 4 illustrates movement of material by electroosmosis.

FIG. 5 illustrates a device similar to the FIG. 1 device, but electroosmosis is being used to draw cells into the tapers, rather than suction.

FIG. 6 illustrates different ways of lysing cells that are trapped at an inlet: (a) application of a lysis solution; (b) mechanical rupture; and (c) electroporation.

FIG. 7 illustrates a partially-extended cell that has been drawn into a tapered inlet by the application of a potential.

FIG. 8 shows a cell being drawn into a channel by the application of suction.

FIG. 12 illustrates the preferred patch width relative to the channel width.

FIG. 13 illustrates a device of the invention having a plurality of channels running horizontally and a plurality of stripes of immobilised oligonucleotide probes running vertically. A cross section (X-X) along one of the channels is also shown.

In FIG. 16 the lid is flat, but in FIG. 17 it has a cut away portion which forms part of the channel.

FIG. 32 illustrates the use of antibodies during cell capture. In FIG. 32A, a trapped cell is retained by a capture antibody (illustrated as a 'Y' shape). In FIG. 32B, one end of a tube is coated with capture antibodies.

FIG. 33 shows a plan layout of microfluidic channels in a device of the invention.

FIG. 38 shows hybridisation and reverse transcription on a microarray.

FIG. 39 illustrates a test system for simultaneously assessing hybridisation and reverse transcription with a tethered oligonucleotide.

FIGS. 43 to 45 show the effect of oligo-dT length on reverse transcription.

FIG. 50A shows ink that has passed partially through 10 of the 20 channels. In FIG. 50B, using similar channels, ink has passed fully along several channels.

FIG. 60 shows hybridisation of mRNA to an array with a variety of treatments.

FIG. 61 shows images of a 100×100 pixel area of a surface. The X & Y axes show the position in μm. The gradient on the right is fluorescence intensity on an arbitrary linear scale.

FIG. 62 shows the results of an experiment involving second strand cDNA synthesis.

In FIG. 64 the nucleic acids are confined on the surface using physical means, whereas in FIG. 66 the surface is selectively activated using UV light. FIG. 65 shows fluorescence of nucleic acids attached by the FIG. 64 method, while

In FIG. 70, part of a living cell is extending into the channel.

FIG. 71 shows a liquid front moving through the FIG. 53 device. The fronts enter the channels uniformly.

FIG. 73 shows a time trace of fluorescence intensity over a period of 10 seconds (X axis) for three arbitrarily selected positions on the support shown in FIG. 61. 100 images were collected using 100 ms exposure time, each at maximum laser power. The digital levels (i.e. the number of fluorescent dye molecules) are indicated by the horizontal lines.

MODES FOR CARRYING OUT THE INVENTION

Microfabricated Device

Figure 1:
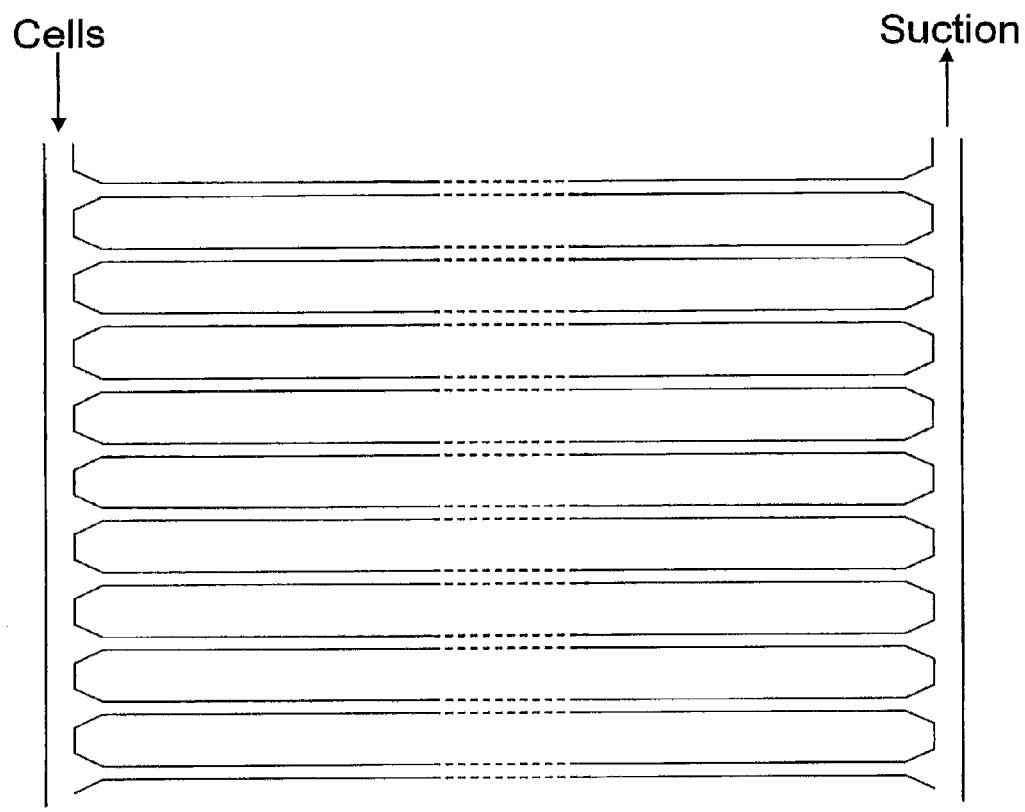
FIG. 1 is an illustration of a device of the invention, with a plurality of channels, tapered inlets for trapping cells, and using suction to draw cells into the tapers.
Figure 2:
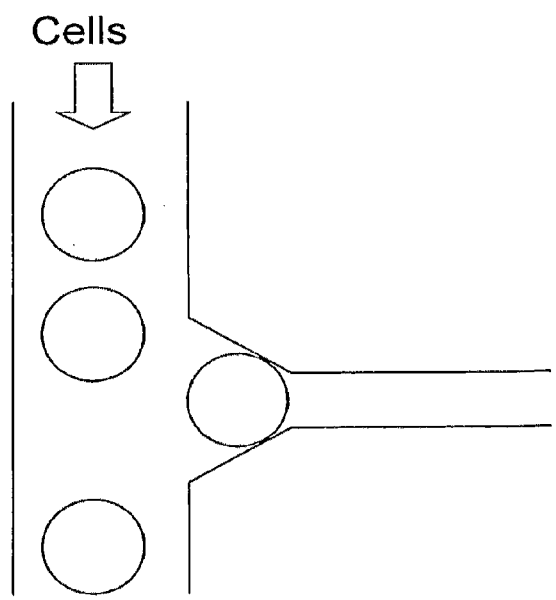
FIG. 2 illustrates a cell being trapped in a tapered inlet.
Figure 9:
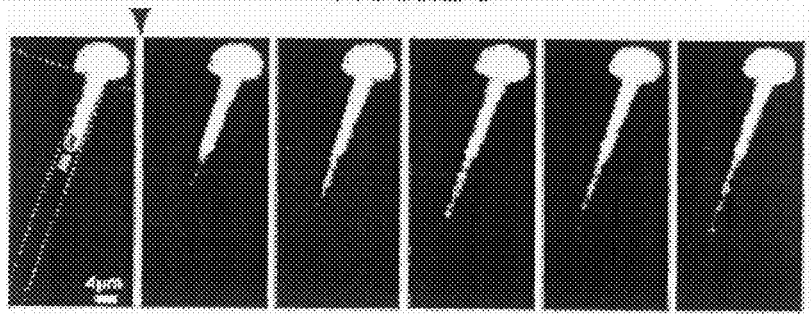
FIG. 9 shows a cells fluorescently-labelled contents being removed and drawn into a channel by electroporation.
Figure 10:
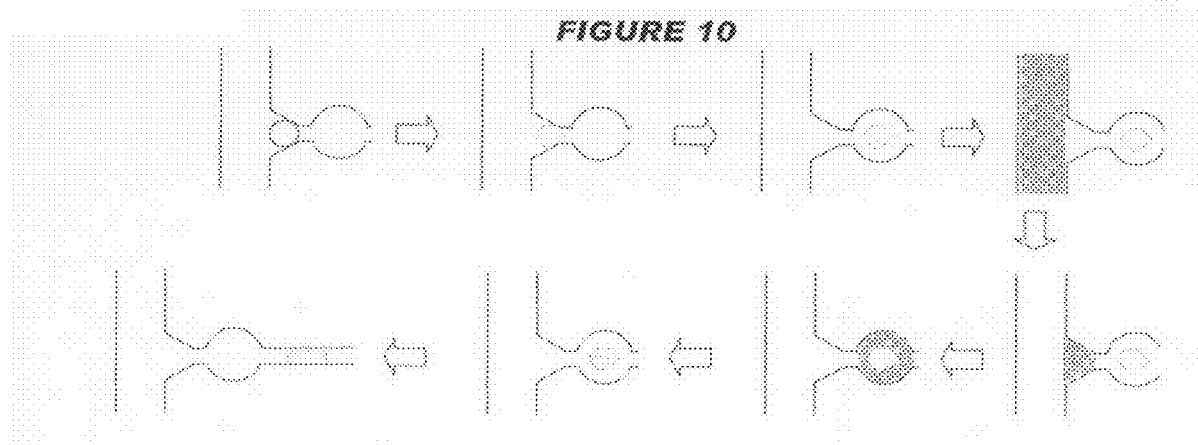
FIG. 10 illustrates the operation of an expansion chamber for treating cellular contents.
Figure 11:
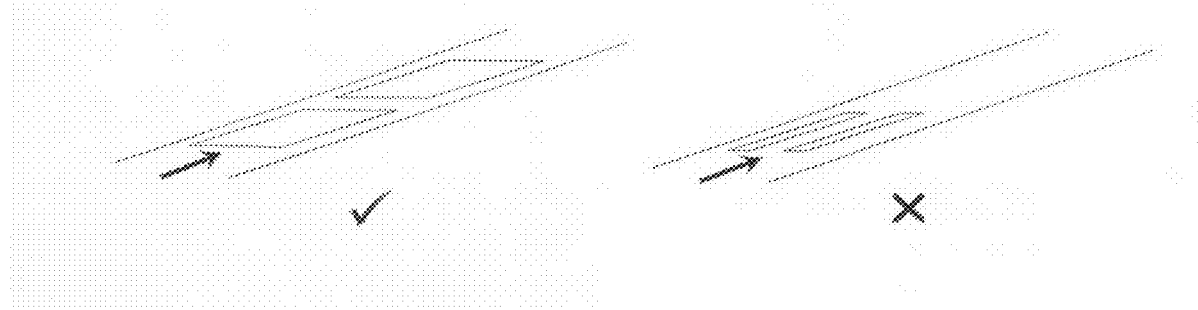
FIG. 11 illustrates the preferred arrangement of neighbouring patches along a channel.
Figures 14, 14A:
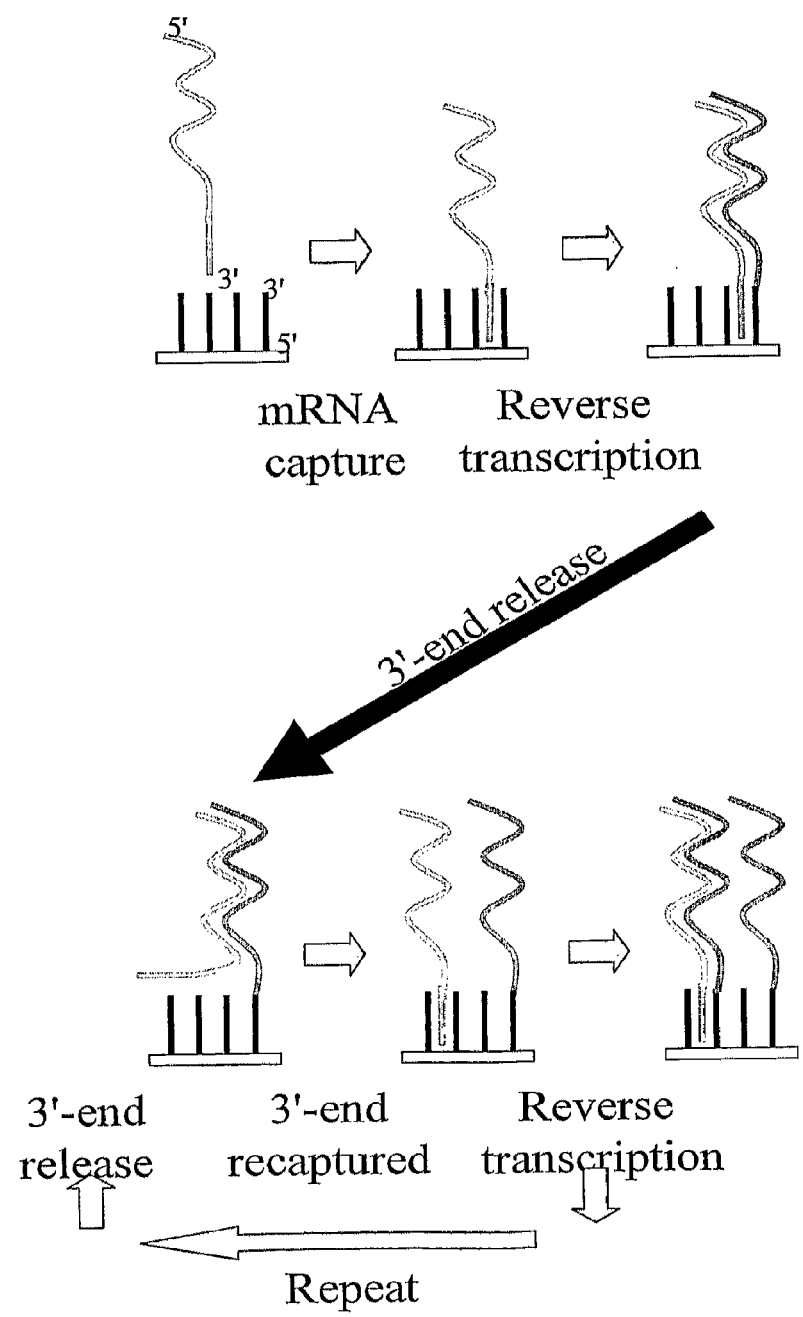
FIG. 14 illustrates the serial reverse transcription aspect of the invention.
FIG. 14A illustrates the early-to-middle stages.
Figure 14B:
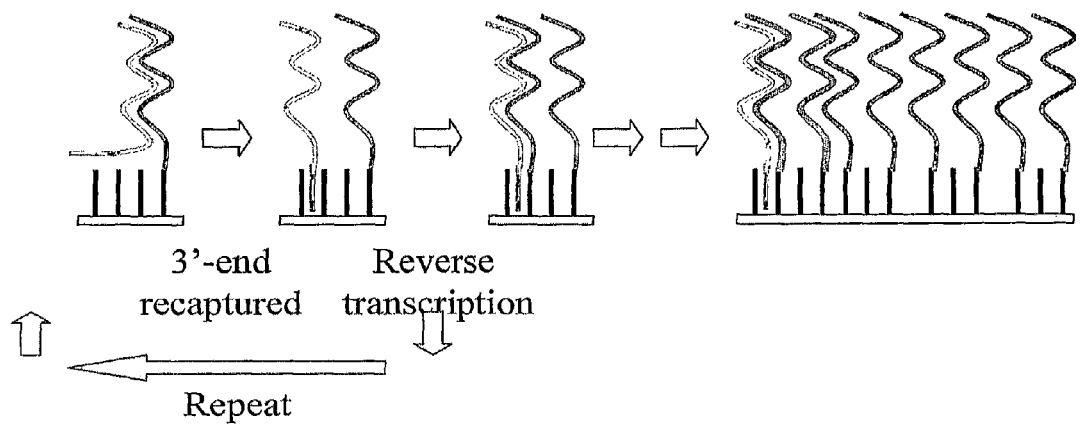
FIG. 14B shows the middle-to-late stages.
Figure 14C:
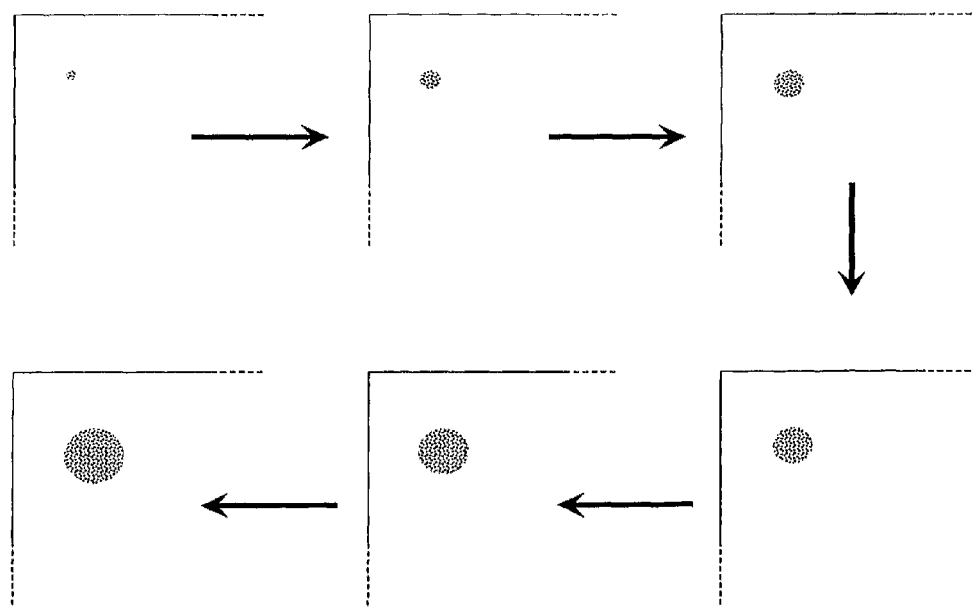
FIG. 14C illustrates how a small spot of label can be amplified in this way.
Figure 15A:
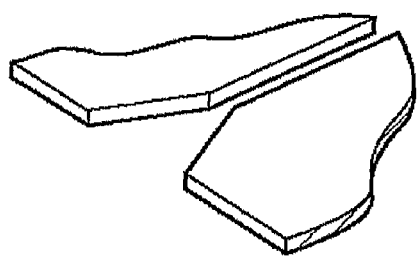
FIG. 15 illustrates two types of tapered inlet, narrowing in either (a) one dimension or (b) two dimensions.
Figure 15B:
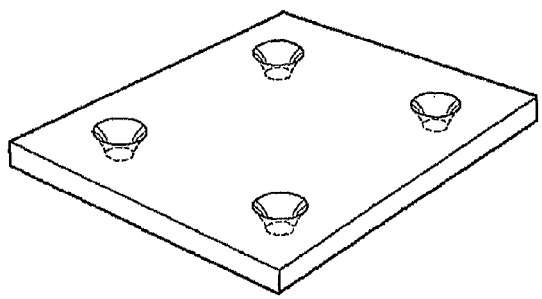
Figures 15, 16:
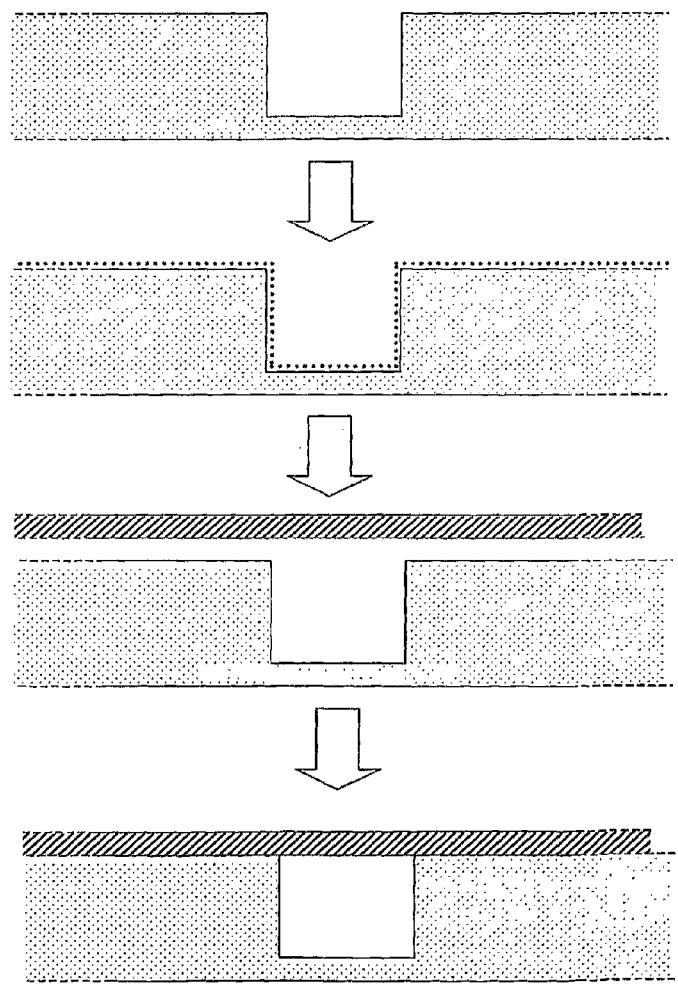
FIG. 16 illustrates how a device can be assembled. A substrate with a channel is selected, then a line of DNA probes is applied orthogonally to the channel. A lid is then applied to the device to seal the channel.
Figure 17:
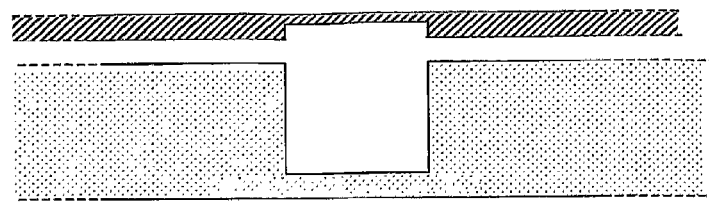
Figure 18:
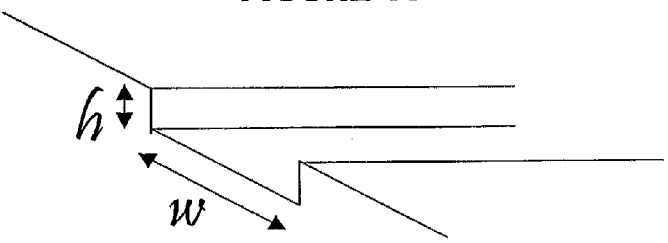
FIG. 18 illustrates dimensions of channels.
Figure 19:
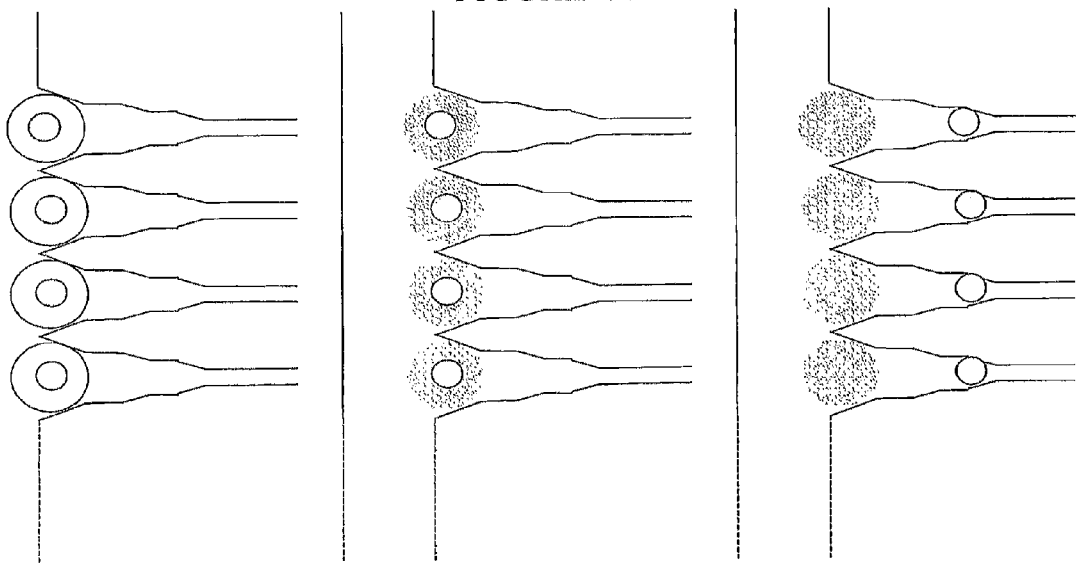
FIG. 19 illustrates the release of organelles at a trapping site.
Figure 20:
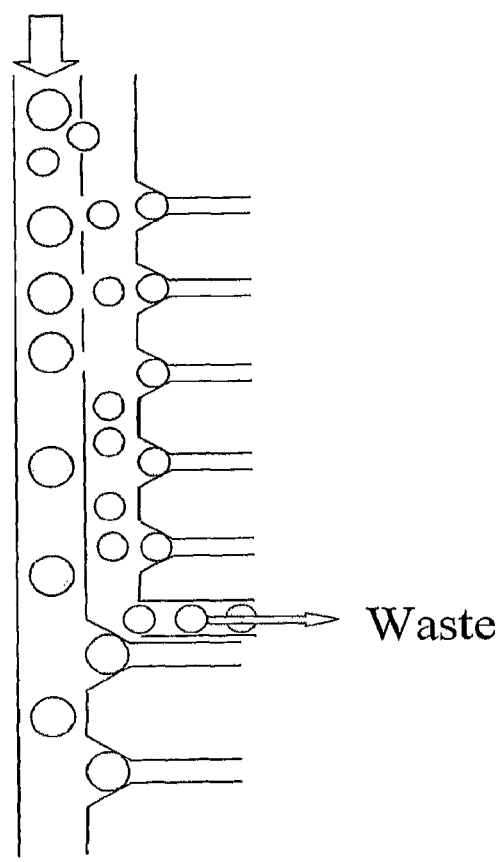
FIG. 20 illustrates size-fractionation of cells before trapping.
Figure 21:
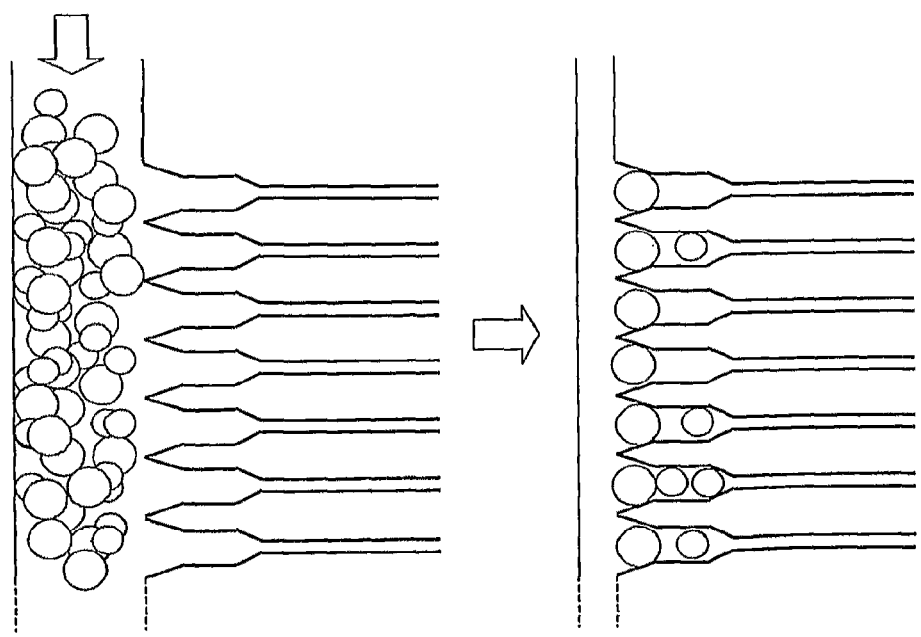
FIG. 21 also illustrates size-based separation of cells, using a series of tapers.
Figure 22:
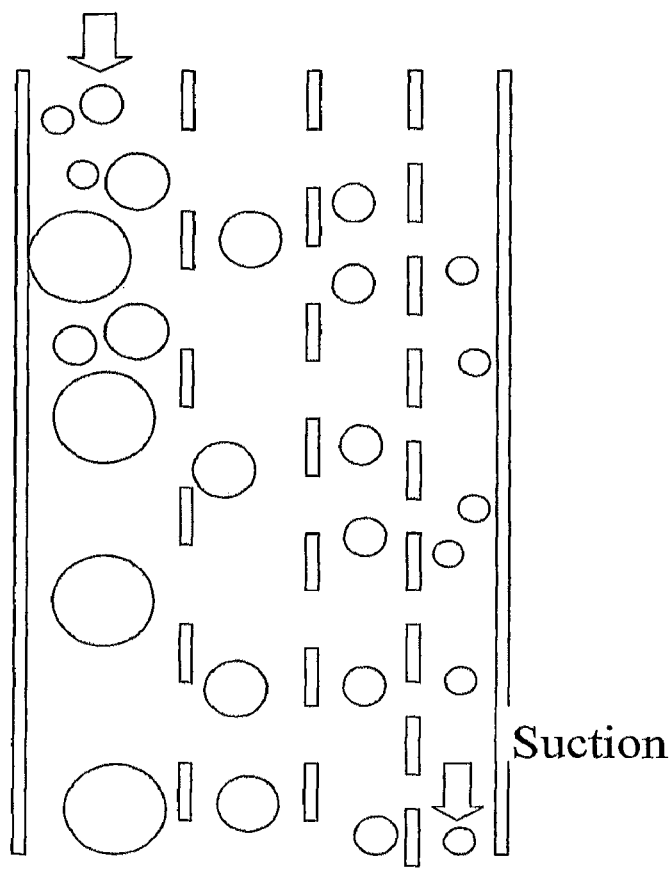
FIG. 22 illustrates a further size fractionation method.
Figure 23:
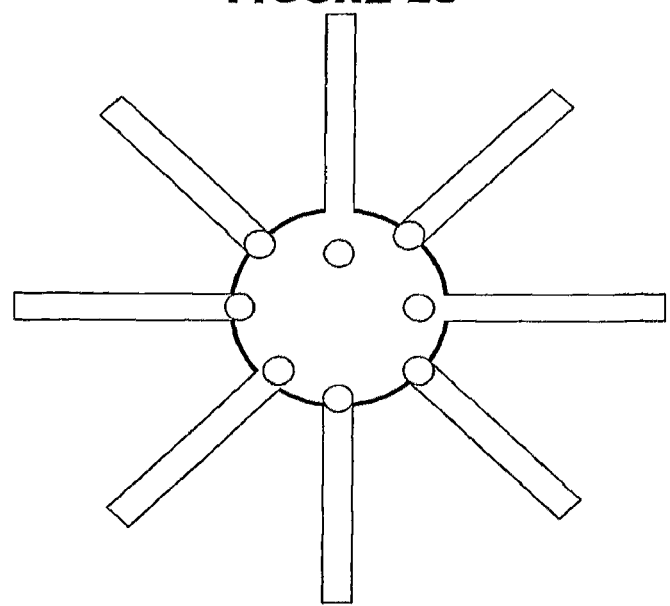
FIG. 23 illustrates a device in which channels extend radially from a central point.
Figure 24:
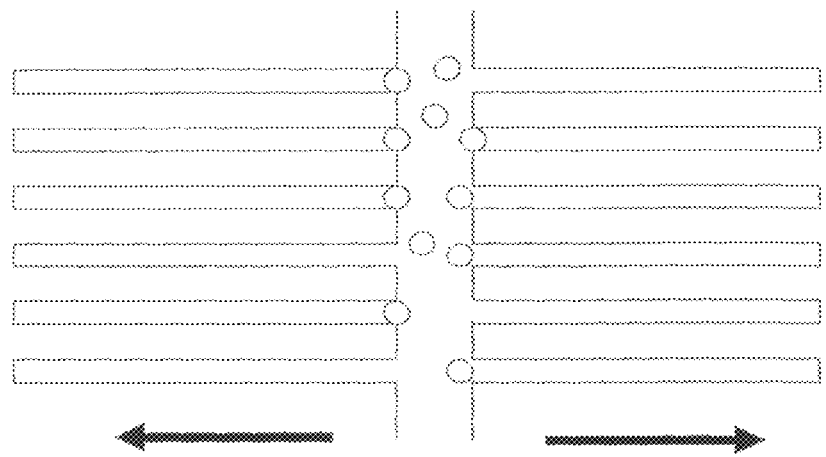
FIG. 24 illustrates a device with parallel channels extending in opposite directions from a central delivery line.
Figure 25:
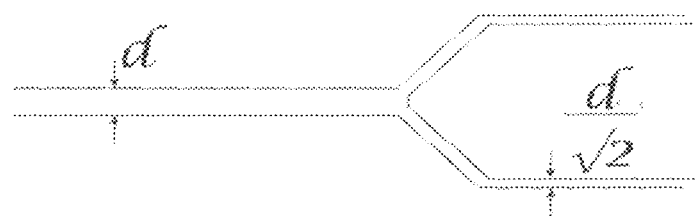
FIG. 25 illustrates a channel which branches into two sub-channels. The channels shown have a circular cross-section, and so the diameter decreases by $\sqrt{2}$ to maintain a constant cross-sectional area. With square or rectangular cross-sections then the width of a channel would simply halve.
Figure 26:
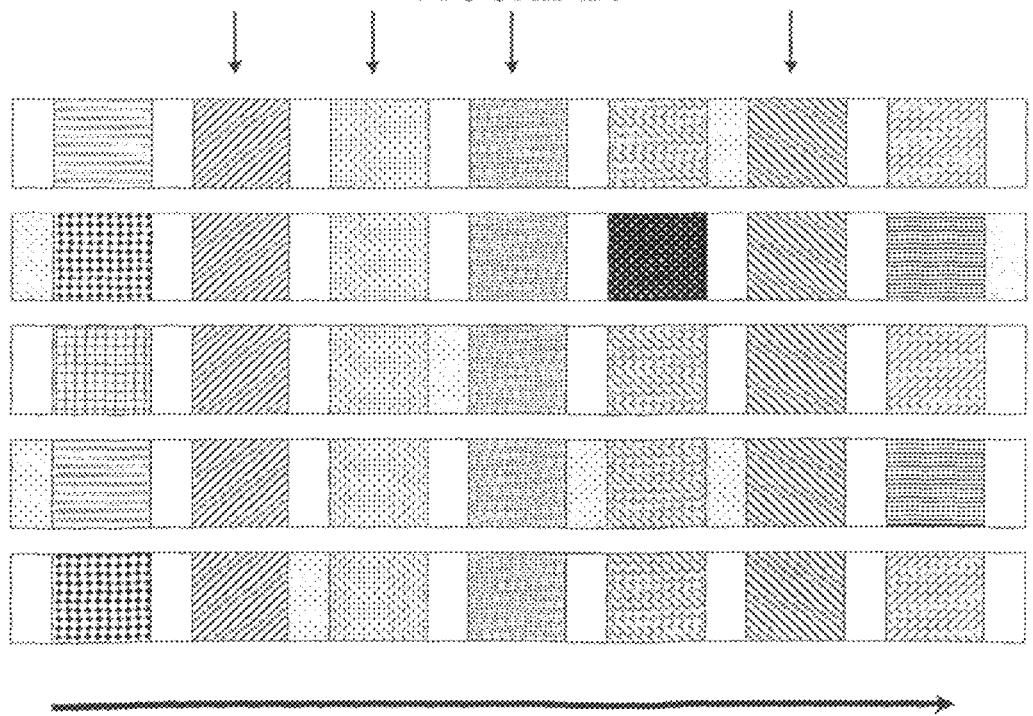
FIG. 26 illustrates five channels, each having seven analysis patches. The four patches marked with arrows are common analytical components.
Figure 27:
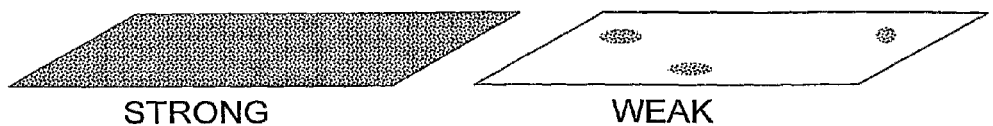
FIG. 27 illustrates a patch which has hybridised to a large number of transcripts ('strong') and a patch which has hybridised to a small number of transcripts ('weak').
Figure 28:
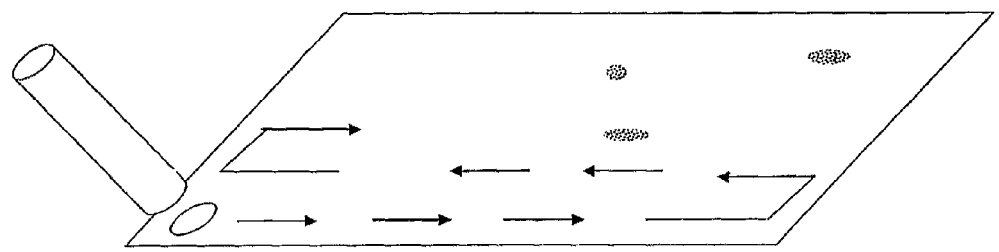
FIG. 28 shows a laser spot scanning a spot with three hybridisation signals.
Figure 29:
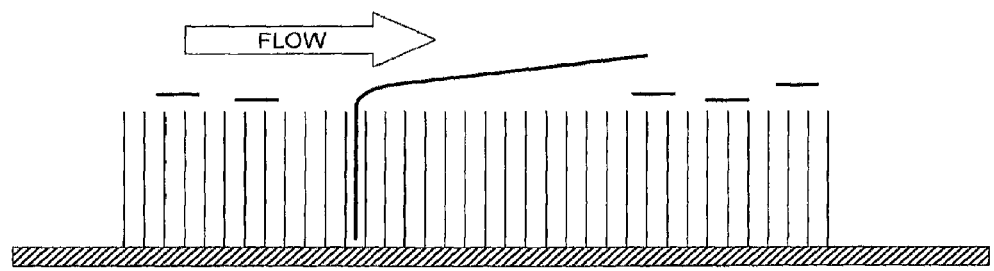
FIG. 29 shows the effect of flow direction on a hybridised transcript, whereby non-specific signal (short black horizontal bars) can be distinguished from true signal.
Figure 29:
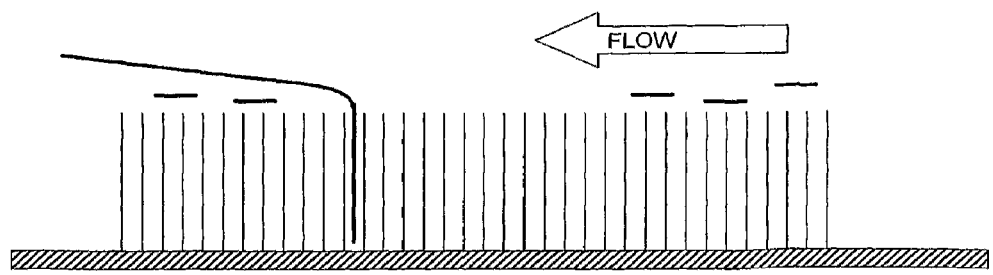
Figure 30:
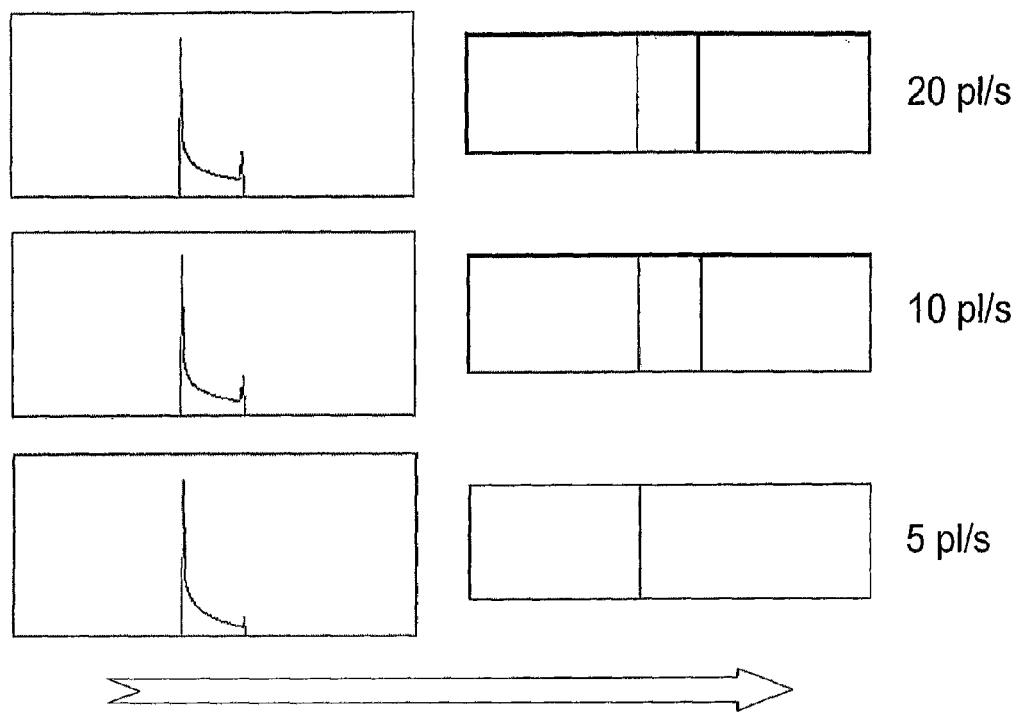
FIG. 30 shows the distribution of mRNA target captured on a patch of immobilised complementary DNA at three different flow rates (picoliters per second). The left graph shows density from the side, and the next panel shows density viewed from above.
Figure 31:
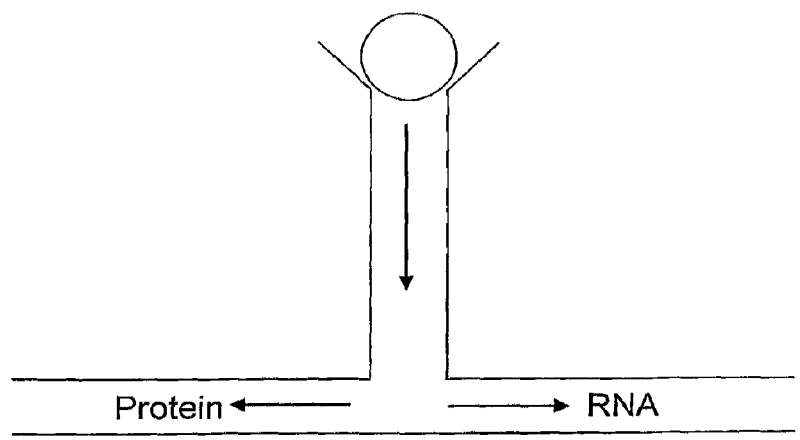
FIG. 31 shows a branched channel in which proteins move one way and RNA moves another.
Figure 34:
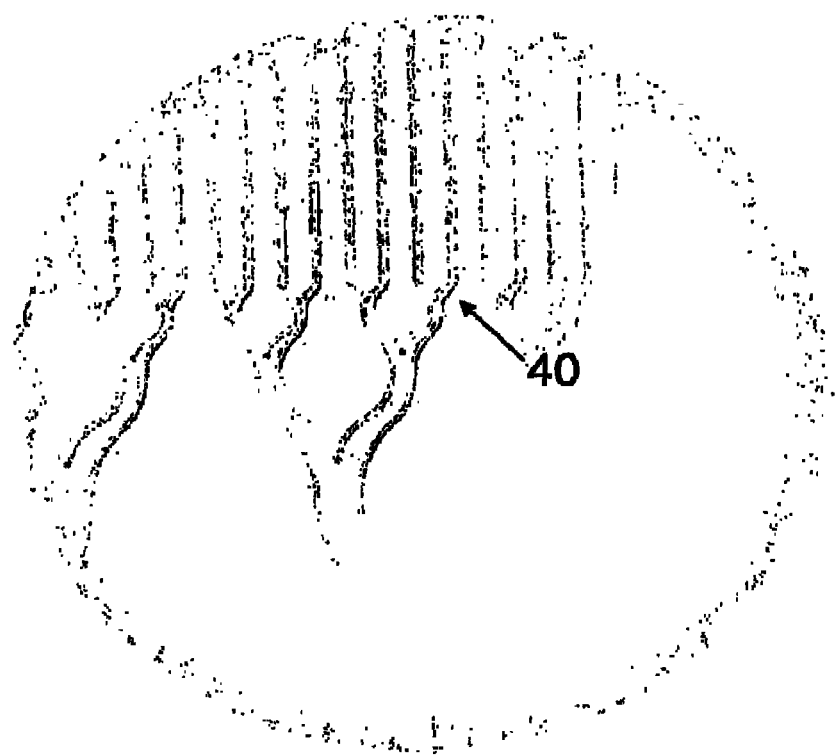
FIGS. 34 to 36 show magnified detail of features of the device when made in PDMS.
Figure 35:
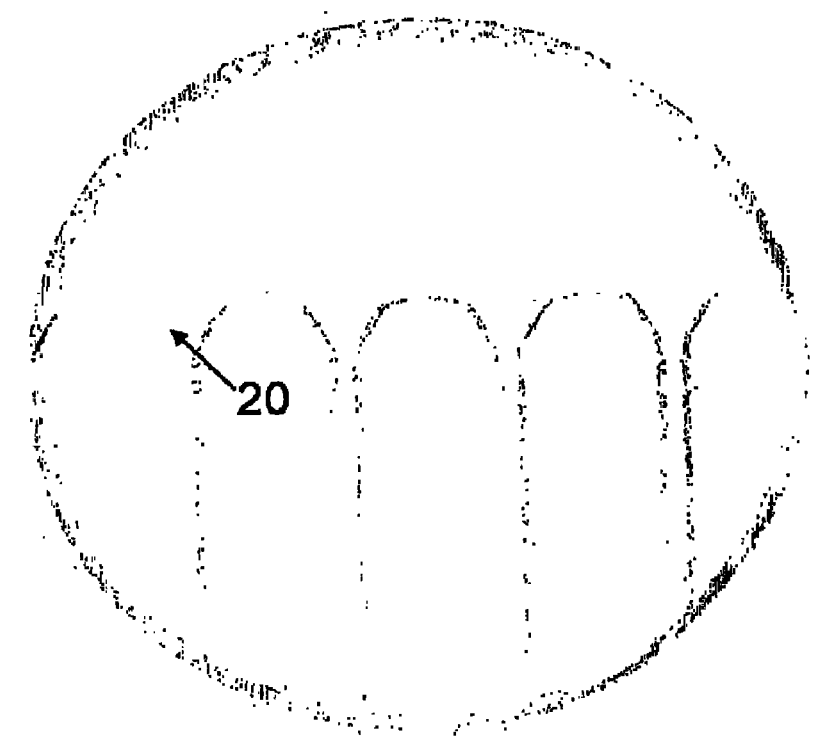
Figure 36:
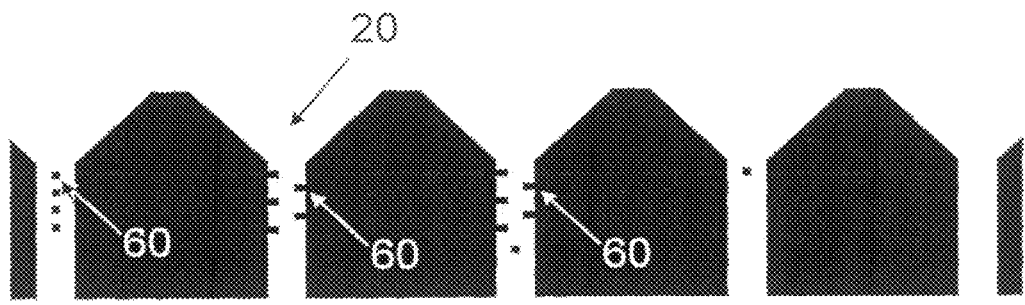

A microfluidic network (1) with a plan view as shown in FIG. 33 was made within a PDMS slab. Cells enter at the top of the device, along delivery line (10). Single cells are trapped at the tapered entrances (20) of multiple parallel channels (30) and their contents travel in the direction shown by the arrow. After travelling along the channels (30), reagents leave the output ends (40) of the device (1) by exhaust (50). An enlarged view of the output ends (40) in the final PDMS device (1) is shown in FIG. 34. An enlarged view of the tapered entrances (20) in the final PDMS device (1) is shown in FIG. 35. Detail of the regions downstream of entrances (20), including various arrangements of projections (60) for trapping cells, is shown in FIG. 36. The channels (30) have a rectangular cross-section, being 10 μm wide and, depending on the thickness of PDMS used, from 2-20 μm high. Adjacent channels are separated by 60 μm. The entrances (20) taper from 50 μm to 10 μm. Projections (60) are either posts (2 μm×2 μm) in a channel or baffles (2 μm×3 μm) projecting from a wall.

Figure 53:
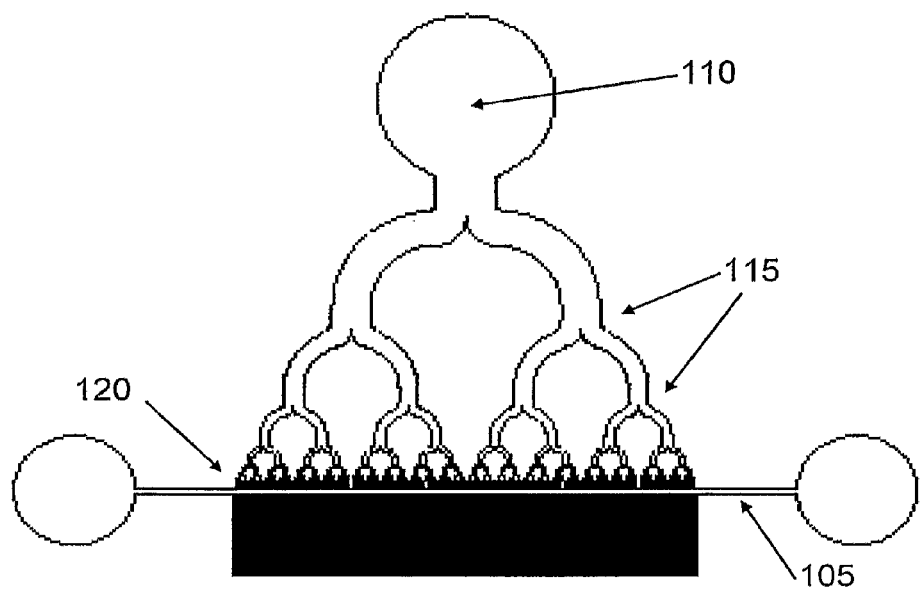
FIGS. 53 to 55 show an alternative arrangement to FIG. 33, showing only the inlet area.
Figure 54:
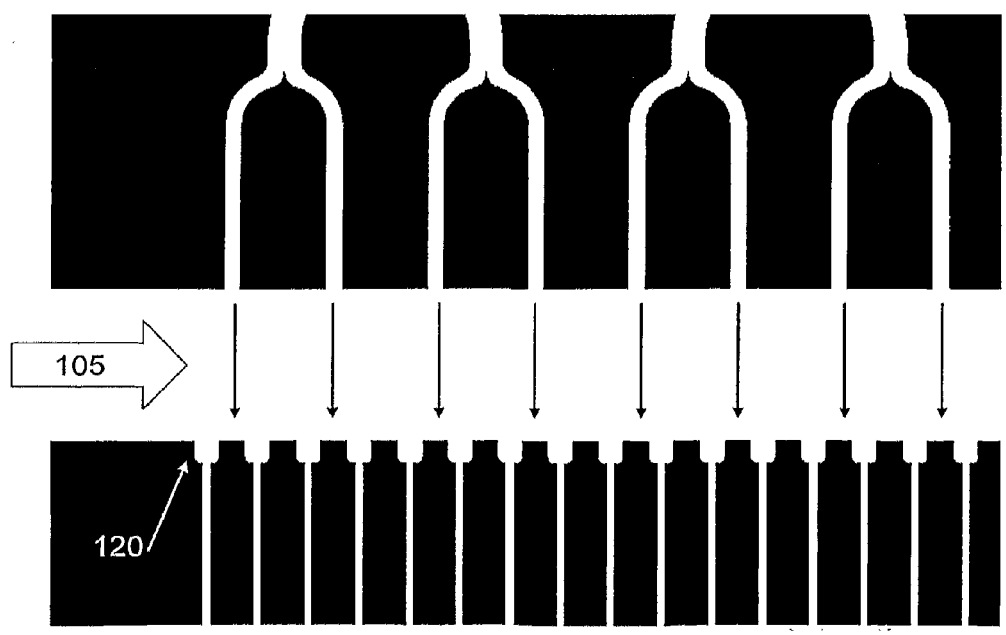
Figure 55:
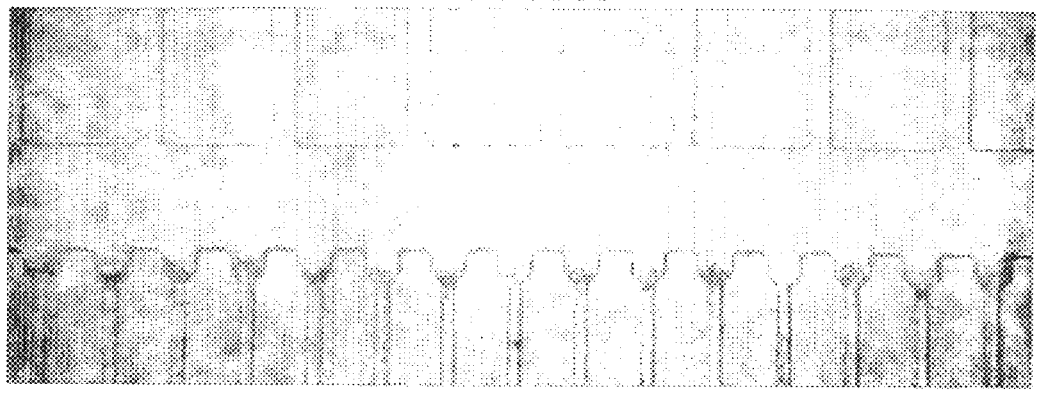

An alternative arrangement for the pre-trapping part of a device is illustrated in FIG. 53. A suspension of cells enters the device via delivery line (110) and flows through a flow-splitter with bifurcating channels (115), designed to distribute the flow and cells equally prior to delivering them to a series of cell trapping sites (120). Liquid can pass uniformly through the bifurcating delivery line channels (FIG. 71). These channels decrease from 1 mm wide down to, for example, 25 μm. In contrast to the arrangement shown in FIG. 33, therefore, the cells flow into the cell trapping sites in a direction parallel to the analysis channels, rather than in a direction perpendicular to them (FIG. 54). A perpendicular busline (105) is still present, however, and can be used to flow reagents passed the trapped cells e.g. to perform lysis, or to expose the cells to chemical stimuli. This line (105) is typically 50-500 μm wide. Where the number of cells in a sample is low, such that capture efficiency is important, this arrangement is more useful that the FIG. 33 arrangement. It can also reduce shear-induced rupture of cells compared to the FIG. 33 arrangement. FIG. 55 shows a microscope image corresponding to FIG. 54.

The devices are made out of PDMS that is bonded to a glass surface with holes corresponding to the inlet holes. The glass surface provides mechanical support for the PDMS, but also for the fluidic connectors that are attached to the inlet holes. The microchannels are made by casting them into PDMS using a silicon+SU8 mould carrying the master pattern. After curing the PDMS the mould is removed, leaving an imprint of the is pattern in the PDMS. The depth of the channels is determined the thickness of the SU8. The total thickness of the PDMS is determined by strips of polyimide tape attached to the glass surface, onto which the mould is rested during the curing process.

For one mould, a 100 mm <100> n-type silicon wafer with 900 nm of thermally grown oxide was dehydration baked for 15 min at 110C on a hotplate. 10 ml of SU8-25 was spun onto the wafer using a commercial spinner and a two-step spin process to a thickness of 50 μm (deposition step). The wafer was baked at 65° C. for 3 min and then at 95° C. for 15 min (pre-baking step). After cooling, the wafer was exposed through a chrome-on-glass mask to 10 mW/cm$^2$ of broadband UV light for 30s using a mask aligner, then post-exposure baked at 65° C. for 1 min followed by 95° C. for 4 min (post-baking step). The wafer was subsequently developed for 5 min using two baths of 1-methoxy-2-propanol acetate, each wafer submerged for 2.5 min per bath and agitated, followed by rinsing in propan-2-ol before blow drying with dry nitrogen. Post-baking was performed at 150° C. for 10 min and then protected using a spun layer of S1818 photoresist, baked at 110° C. for 1 min. The wafer was then diced using a wafer saw with a S1025 diamond saw blade. The moulds were manually separated and the photoresist protection layer removed by rinsing first in acetone and then in propan-2-ol before blow drying with dry nitrogen. After separation the moulds were inspected by eye for any major defects or gross damage.

This method gave a SU8 structure of uniform thickness. To allow for deeper inlet channels (e.g. in order to facilitate cell transport), dual-depth SU8 structures can be used. These can be obtained by successive processing (deposition, prebaking, exposure, postbaking) of several SU8 layers on top of each other, followed by a single development step (as in single-depth fabrication. The fabrication of such dual-depth SU8 structures is described in ref. 54.

The moulds were then used to fabricate PDMS structures using soft lithography [55]. Briefly, PDMS was prepared by mixing base polymer and curing agent with a ratio of 10:1, followed by a degassing step under reduced pressure for 30 min. A small amount of this pre-polymer mixture was poured onto both a SU8 mould and a pre-treated microscope slide, acting as the support. Pre-treatment of the microscope slide was carried out using an adhesion promoter. Moulds were supported by a strip of 5-mm-thick polycarbonate in order to improve their durability in addition to ease of handling. The overall thickness of the cast, which was minimized in order to avoid swelling under the influence of solvents, was controlled by having the mould supported by strips of Kapton tape on either side of the mould, giving an overall thickness of ~180 μm. The total thickness of the PDMS part is determined by the thickness of two strips of tape that are attached to the glass. The microscope slide and mould were brought into contact, sandwiching a film of PDMS and held firmly in place while the PDMS was allowed to cure. On completion, the mould was gently lifted off the cast and the strips of Kapton tape were removed prior to use.

After removing the SU8 mould, the inlet holes in the supporting surface are filled with PDMS and need to be cleared. The plug of PDMS was removed using a hole punch with a diameter slightly smaller than the diameter of the inlet hole. Care needs to be taken during removal of the plug in order not to generate debris with dimensions larger than the channel dimensions. A template slide with identical hole positions protects the structure against microscopic dust particles and debris generated during the punching process, and helps to guide the hole punch. The hole punch is a needle shaft which is sharpened from the inside on one end, in order to provide a cleaner cut. The shaft is pulled fully through the hole, rather than being pulled back, in order to prevent debris being pulled back and into the structure. A 19G needle (0.9 mm) mates well with the inlet holes (1 mm).

Figure 72D:
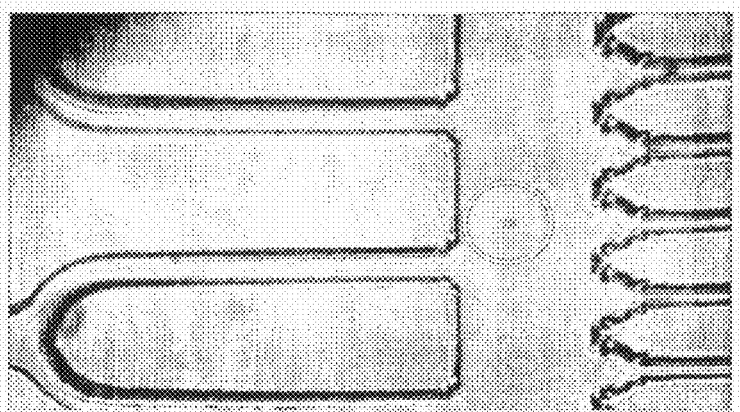
FIG. 72 shows six stills from a video of the delivery line, reagent supply line and cell trapping sites of a device of the invention. A cell is circled in frames B to F, showing its movement from entry to trapping.
Figure 72E:
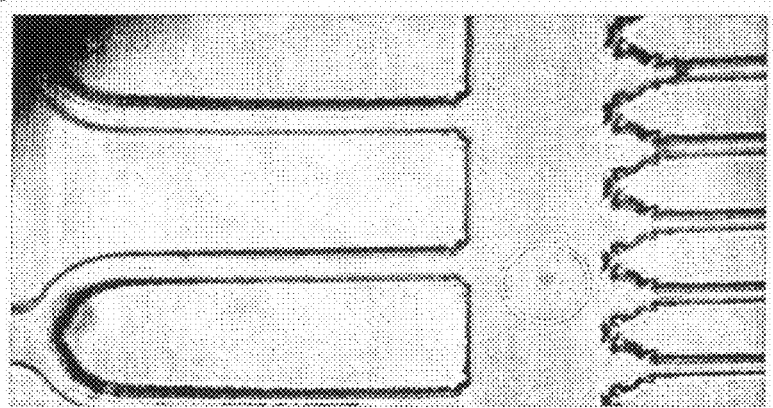
Figure 72F:
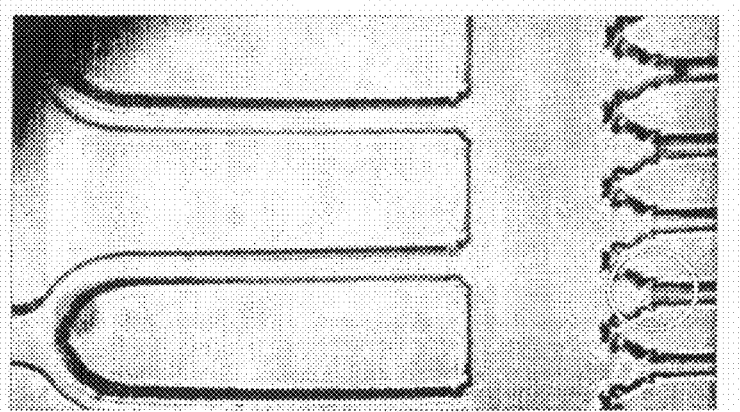

FIG. 72 shows a cell entering a FIG. 53 device and being captured in a tapered trapping site. The device was 25 μm high and was supplied by a syringe loaded with 50 μL buffer, 10 μL Trypan blue, 10 μL buffer, 5 μL cell suspension (100 cells/μL) and 10 μL buffer. The flow rate was 1 μL/min during the sequence shown in FIG. 72.

Figure 37:
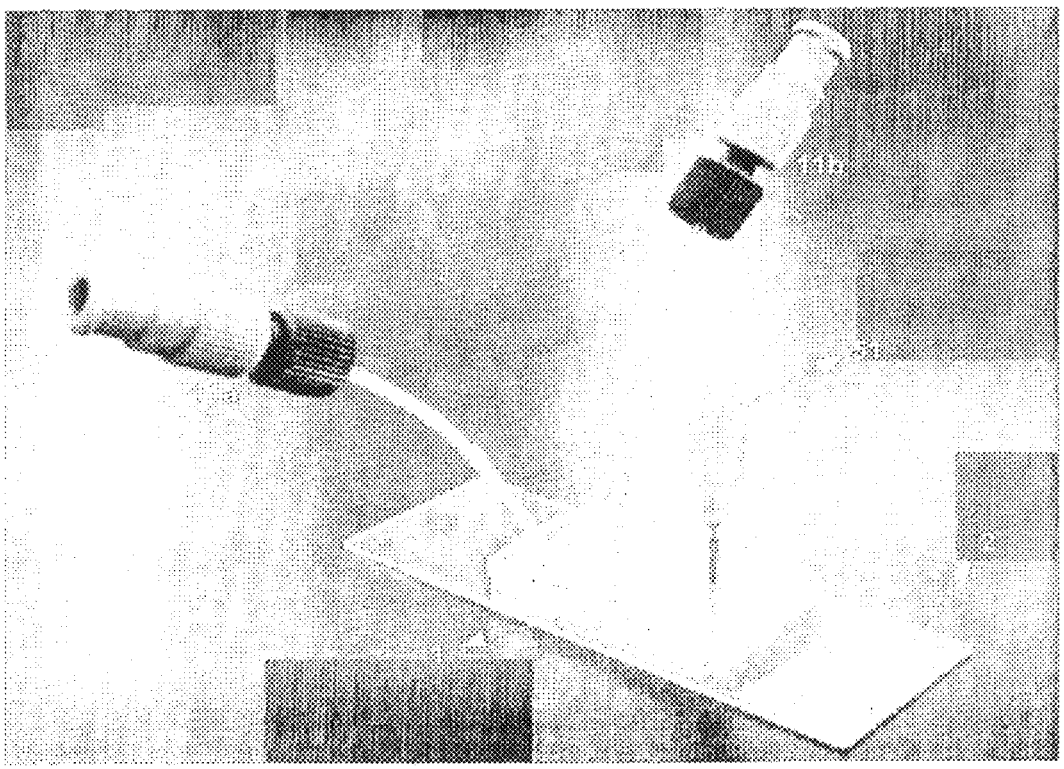
FIG. 37 shows the device with input and output tubes, attached to a DNA microarray.

As shown in FIG. 37, the device (1) was placed in contact with a DNA microarray which had been prepared on a glass microscope slide (2). The PDMS formed a seal against the glass, thereby preventing leakage of aqueous solutions without requiring any application of pressure. Pipes (11a & b) leading in and out of channel (10) were inserted into the PDMS device (1), and an exhaust pipe (51) was also inserted.

A suspension of cells, such as human leukocytes, can be introduced into delivery line (10) via pipe (11a). Bulk fluid leaves via pipe (11b) but, due to slight suction through exhaust pipe (51), some fluid gets drawn into channels (30). Individual cells enter tapered entrances (20), but are too large to enter channels (30), and so they become trapped in entrances (20). While maintaining the suction pressure, lysis solution is introduced into delivery line (10) via pipe (11a). This lyses cells trapped in entrances (20), releasing their contents to flow down channels (30), where they can interact with the microarray probes on slide (2).

Figure 56:
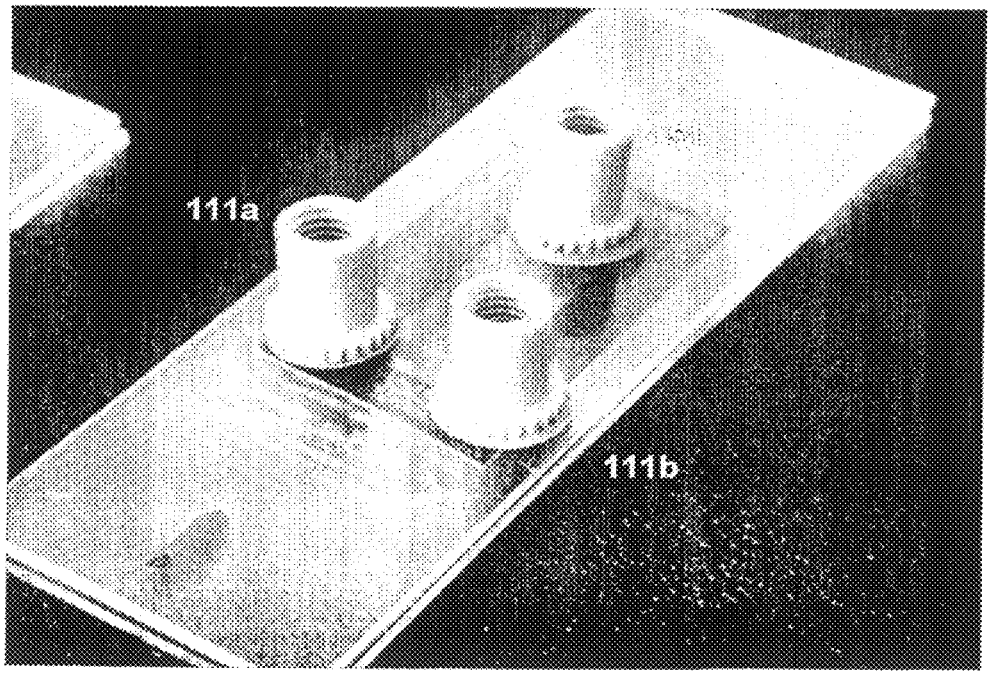
FIG. 56 shows a device with attached fluid connectors.

As a more robust way for fluidic connections, commercially available connectors can be used. A typical assembly consists of a port and a matching connector. The ports are positioned over the inlet holes on the glass support piece, aligned with the aid of a syringe needle and piece of matching PTFE tubing, and glued down with epoxy resin. The epoxy resin is cured overnight, after which the syringe needle and piece of PTFE tubing are removed. FIG. 56 shows a device with such connectors attached. Using this device, a Harvard PHD2000 dual syringe pump was attached to connectors 111a, 111b and 151 and was used to load the device with a suspension of cells. The pistons of both syringes move in parallel using this pumping arrangement. Using a number of valves, the sample can be moved around in any direction quite easily.

Figure 46:
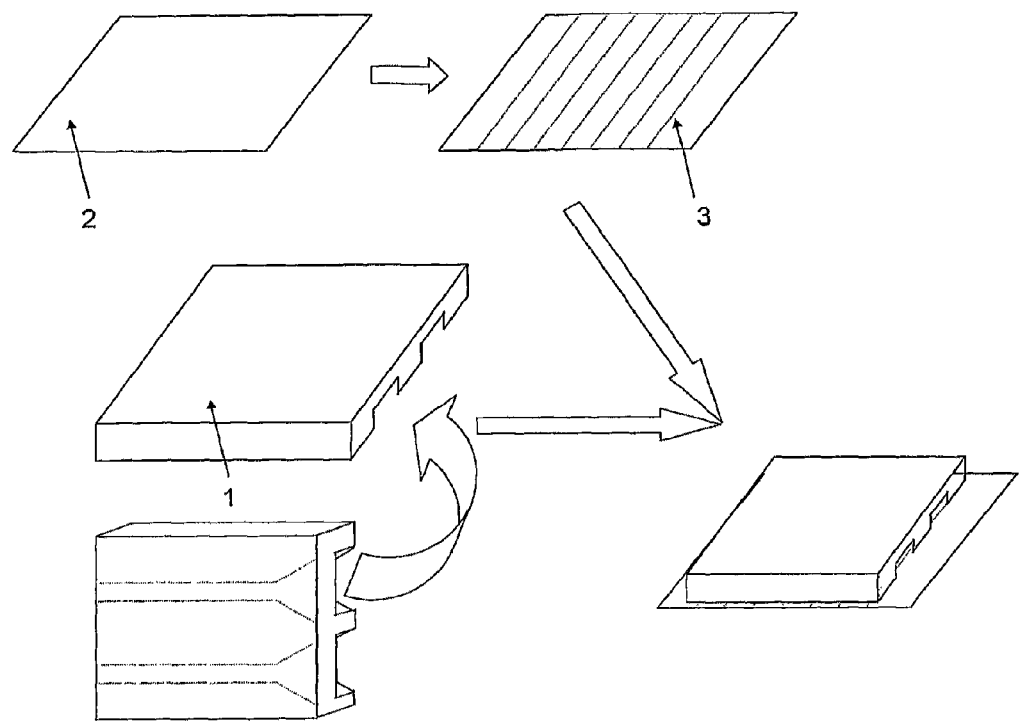
FIG. 46 shows construction of a simple device. Channels are made in PDMS (1). Parallel stripes (3) of oligonucleotide probes are applied to a slide (2). The PDMS channels are placed over the slide, with the channels parallel to the stripes.
Figure 47:
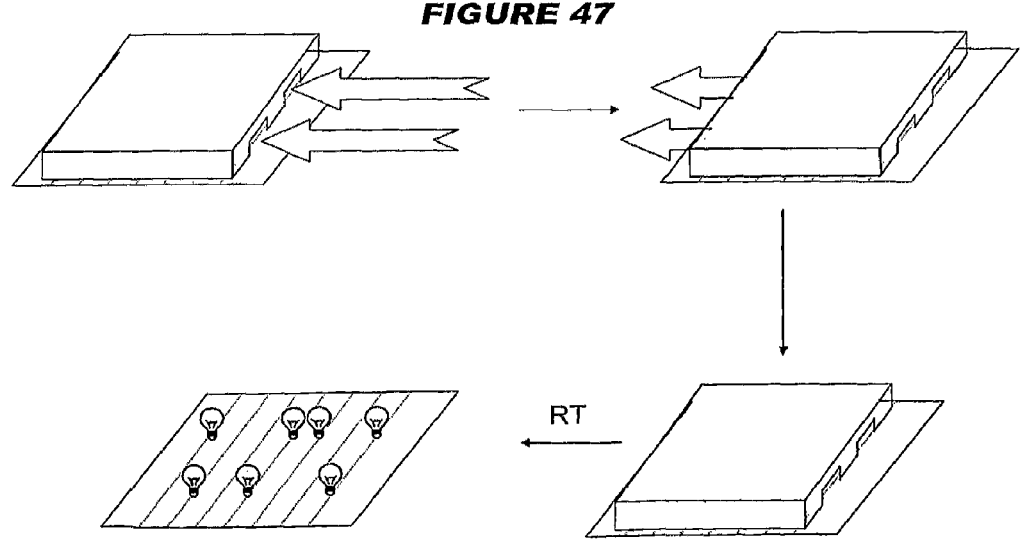
In FIG. 47, the mRNA contents of two cells pass through separately through two channels. Reverse transcription takes place with incorporation of fluorescent labels, which are then visualised. The different cells show different fluorescence patterns.
Figure 48:
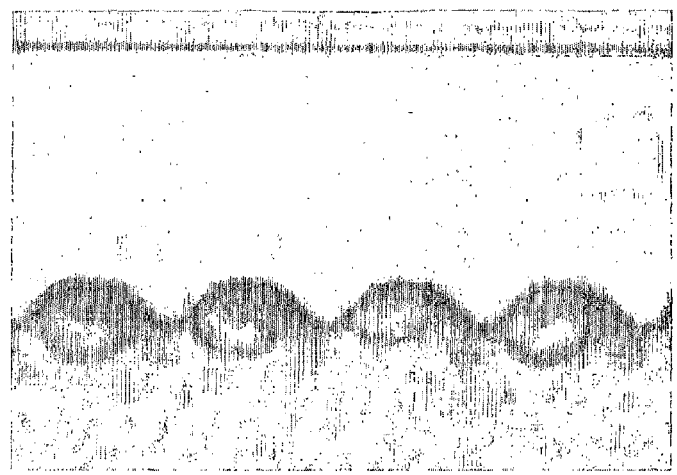
FIG. 48 shows four cells individually trapped in a microfluidic device.
Figure 69:
FIGS. 69 and 70 show cells trapped in devices of the invention, after staining of dead cells with Trypan Blue.
Figure 70:
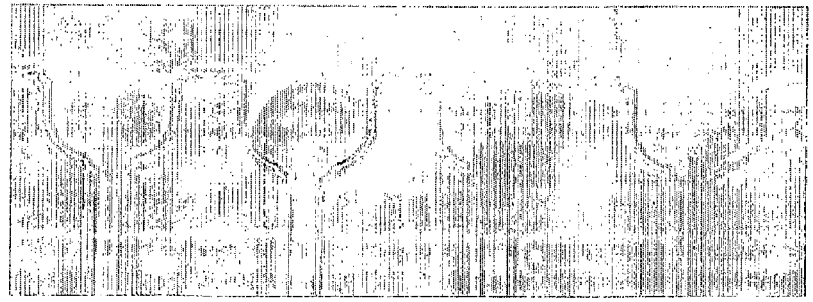

An array of substantially parallel lines (3) of nucleic acid probes can conveniently be made using the electrochemical methods disclosed in reference 34. As shown in FIG. 46, the PDMS device (1) can be arranged such that its channels are substantially orthogonal to the lines on the arrays. Individual cells can be trapped at the entrances to the channels (e.g. as shown in FIGS. 8, 48 & 69), lysed in situ, and their mRNA contents can flow down separate channels, each encountering the same series of nucleic acid probes. Hybridised mRNA is reverse transcribed after hybridisation, with fluorescent bases being incorporated during reverse transcription (FIG. 39). The channel device (1) can then be removed and fluorescence on the array (2) can be read by standard techniques (FIG. 47). Depending on the size of the stripes and the concentration of mRNA, the array can be visualised using either a standard microarray reader or a high-resolution reader which is capable of detecting single molecules and can be used for sensitive high resolution fluorophore detection, such as the CytoScout™ reader.

In Situ Cell Lysis

For lysing cells, two buffers were used.

The first lysis buffer was a lithium dodecyl sulphate lysis buffer, containing: 100 mM Tris (pH 7.5); 500 mM lithium chloride; 10 mM EDTA; 1% lithium dodecyl sulphate; and 5 mM DTT. The LiDS detergent allows histones to remain bound to the genomic DNA, keeping it compact. Addition of a RNase inhibitor will prevent degradation of mRNA.

The second buffer was a guanidinium thiocyanate lysis buffer, containing: 3M GuSCN; 2 mM sodium citrate; 2% β-mercaptoethanol; 1% Triton X-100; 1 M NaCl; 10 mM Tris (pH 7.5); and 1 mM EDTA. The chaotropic lysis agent GuSCN disrupts hydrogen bonding, salt bridges and hydration of all proteins. As a result, histones are stripped from the genomic DNA and supercoiling is unwound. It also denatures cellular RNases.

These buffers were applied to cells that had become trapped on a solid surface and lysis was observed using a microscope. Using the first buffer, the concentration of intact cells had decreased about 10-fold in 10 seconds, and after 30 seconds all cells had lysed. The second buffer was stronger, as no intact cells were visible after 10 seconds. The choice of lysis buffer will dictate how long cells should be held in the tapered inlets before lysis is complete e.g. up to 30 seconds.

Fluid Movement Through and Hybridisation within Sealed Microfluidic Channels

Figure 49:
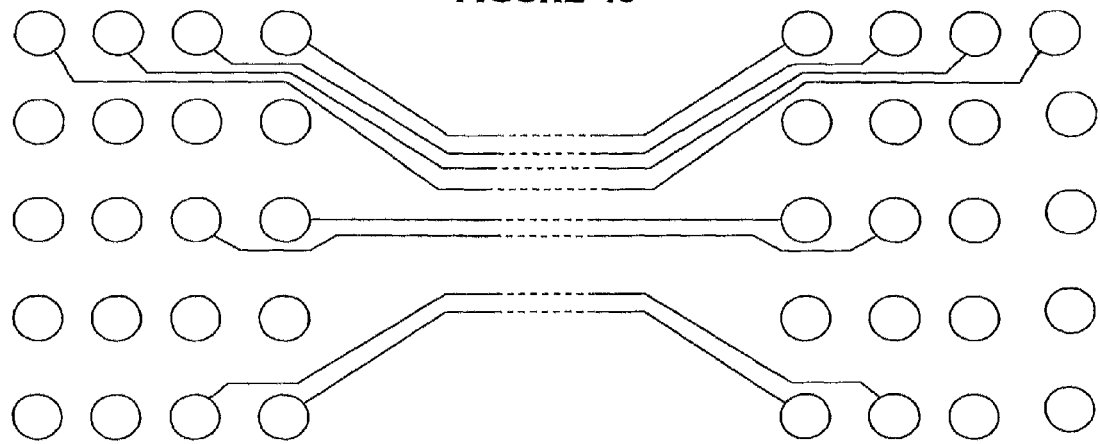
FIG. 49 is an illustration of a device with 20 channels, each channel having circular input and output holes arranged in 5×4 arrays. Only eight channels are shown.

Parallel channels were embossed in a flat piece of PDMS. The PDMS structure had 20 parallel channels. The two ends of each channel terminate in a circular hole having an axis running perpendicular to the plane of the PDMS. Thus there are 20 input holes at one end of the PDMS structure and 20 output holes at the other end, with the holes arranged in a 5×4 array. FIG. 49 illustrates this arrangement, showing only 8 of the 20 channels.

The PDMS structure is pushed against a glass slide to close the channels, except for the input and output holes. The glass and PDMS were found to remain firmly fixed together due to the 'stickiness' of PDMS.

To test the basic working of the device fluidics, and in particular to confirm that fluid can move through the channels without spilling out through the PDMS/glass interface and without distorting the channel walls, coloured ink was injected into the channels via the input holes. FIG. 50A shows results of this experiment, visually confirming that fluids can pass down the channels in good fluidic motion without leakage into neighbouring channels.

Absence of leakage between neighbouring channels was confirmed using a fluorescent label and fluorescence microscopy.

To confirm that nucleic acid hybridisation can take place within channels, a 5'-CTACGC hexamer probe was attached to a patch on the surface of a glass slide using conventional chemistry. Briefly, a Schott epoxy slide was ring-opened using 10 minutes agitation in 10% HCl aq. The hexamer was synthesised using a PPDMS gasket, LongPC®uple cycle, ABI deblock and oxidiser. Deprotection was at 60° C. for 25 minutes in 50/50 EtOH/Ethanolamine, followed by rinse with EtOH/$N_2$. The glass slide and a channelled PDMS structure were rinsed with MeOH/$N_2$ and pushed together, as before.

Even-numbered channels received 100 µl of a Cy5-labelled target complementary to the immobilised hexamer probe sequence, spotted at one end of the PDMS channel structure. Odd-numbered channels received buffer only. The two outer channels (1 and 20) were not used. Wicking took ~5 minutes to ensure each channel was filled (wick speed ~1 mm/s once it started). After 30 minutes, liquid was blotted from the channels, and the glass and PDMS structures were separated. Rinsing was performed by 5 minutes of rocking in full strength buffer, then 5 minutes of rocking in ½ strength buffer, then centrifugation to dry. An Agilent scanner was used to visualise the slide.

Hybridisation was evident in the channels that received the Cy5-labelled target. There was very low leakage between neighbouring channels. By comparing the odd- and even-numbered channels, leakage could be quantified. The signal/noise ratio of target/buffer averaged 50:1 (20,000 vs. 400), with the highest being 160:1 (32,500 vs. 200) and the lowest being 11:1 (9,000 vs. 800).

Figure 51:
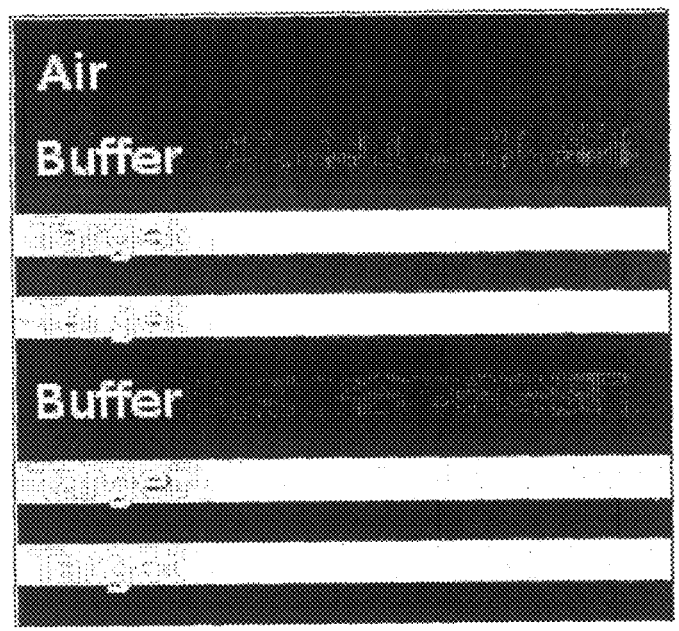
FIG. 51 shows hybridisation signal in 7 adjacent channels of a device.

In a similar experiment, channels received, in order: air; buffer; target; target; buffer; target; target; etc. Results are shown in FIG. 51. Fluorescent signal can be seen only in those channels receiving the target, with no cross-talk between adjacent channels.

Figure 52:
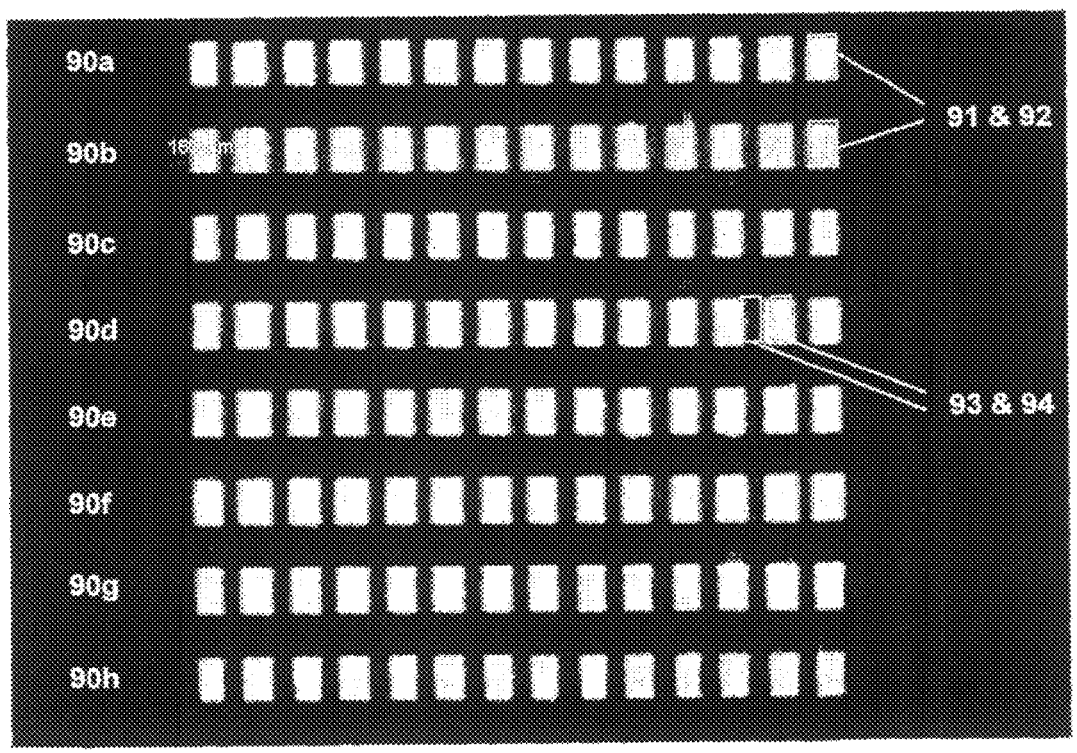
FIG. 52 shows hybridisation signal in 8 adjacent channels arranged orthogonally to 14 stripes of oligonucleotide probes.

In further experiments, an array of oligonucleotides was synthesised electrochemically [34]. Probes were arranged in parallel stripes, with separation between adjacent lines. Channels in the PDMS were 160 µm wide, and were arranged perpendicularly to the oligonucleotide stripes. The effect of overlaying the channels on the stripes is to form a series of oligonucleotide cells along the length of a channel. Labelled target was passed through the channels to permit hybridisation. FIG. 52 shows results in 8 neighbouring channels (90a, 90b, ... 90h). By comparing signal in cells 91 and 92, leakage between adjacent channels was assessed. Similarly, by comparing signal in cells 94 with signal in the gap 94 between adjacent cells, the signal/noise ratio of hybridisation was assessed.

Thus hybridisation can occur in channels without leakage of label into neighbouring channels, and without Cy5-labelled target seeping into unfilled channels. The signal/noise ratio of hybridisation was good. The results show that each channel can be used independently, allowing separate analyses in neighbouring channels.

Electrokinetic Movement

Figure 57:
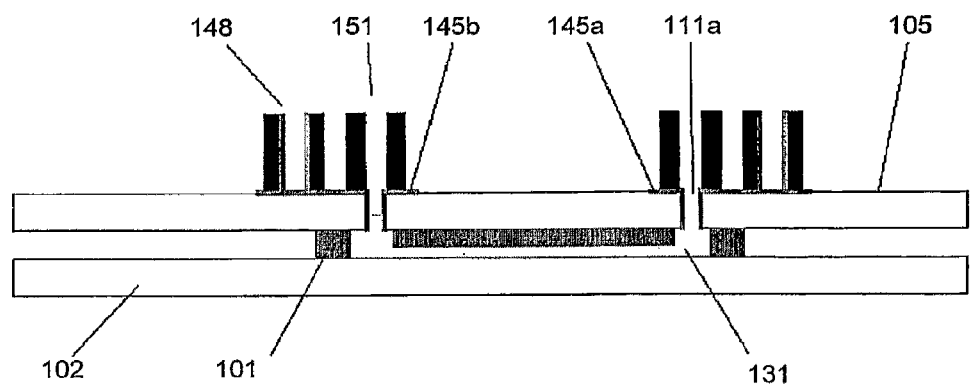
FIGS. 57 and 58 illustrate how electrical connectors are introduced into a device of this type.

To adapt the FIG. 56 device to permit electrokinetic movement of materials within the device (e.g. of the cell suspension and/or cell lysates), electrical contact needs to be established with the liquid inside the microfluidic device. The device was thus adapted as shown in FIG. 57.

The PDMS structure (101) is supported on a glass slide (105), and is in contact with a microarray (102). A cell sample (131) can enter the device via inlet port (111a) and exit via port (151). Ports (111a, 111b, 151) are through the support (105). Using sputter deposition, a metallic film (145a, 145b) is deposited onto the backside of the support (105). Sputter deposition is used in preference to other physical vapour deposition techniques such as electron beam evaporation because it allows one to deposit not only on the flat surface supporting the microfluidic device, but also onto the sidewalls of the inlet holes (111a, 111b). It is through this conductive layer lining the wall of the inlet holes (111a, 111b) that electrical contact can be established with the solution (131) inside the device.

As the metallic film will be in contact with a liquid during the application of a potential and passage of current, it is important that the metal is inert. Noble metals such as gold and platinum can be used for this purpose. A chromium keying layer is deposited first in order to improve adhesion of the noble metal. The film is deposited through a shadow mask, so that only areas in the proximity of the ports are covered. The areas covered with metal act as bond pads. To each bond pad, an electrical socket (148) is attached using silver-loaded epoxy resin.

Figure 58:
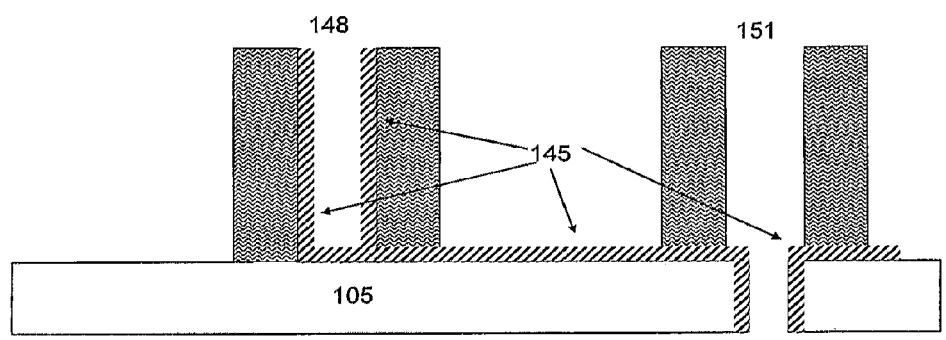

Thus there is an electrically conducting surface through each of ports 111a, 111b and 151, and the surface extends to a nearby electrical connector (e.g. 148) for attachment to a power source. FIG. 58 illustrates this arrangement, showing a metal film layer (145) in contact with the two connectors (148, 151) and support (105).

mRNA Capture from Cell Lysates

After a cell has been trapped in devices of the invention, it is lysed, and its lysed contents are then analysed within a channel. For mRNA analysis, the cell's mRNA will be analysed by hybridisation. Experiments were performed to see if the lysis reagents and/or the released non-mRNA contents would interfere with hybridisation.

FIG. 60A shows hybridisation of a labelled mRNA to an array in two different lysis buffers and in the presence of an increasing concentration of cell lysate. Samples were flowing from left to right. From top to bottom, the 11 samples were: (1) control hybridisation buffer; (2) LiDS buffer+contents of 2 lysed cells; (3) LiDS buffer+50 cells; (4) LiDS+100 cells; (5) LiDS; (6) GuSCN buffer+2 cells; (7) GuSCN+50 cells; (8) GuSCN+100 cells; (9) GuSCN; (10) control buffer; (11) control buffer.

FIG. 60B shows hybridisation in channels of a labelled mRNA to a patch of oligonucleotide coupled to a glass support. The support was clamped against a microfluidic device similar to that shown in FIG. 53. Cells in 1×PBS were pumped into the device followed by a plug of 1×PBS (to keep the lysis buffer separate from the cells) and finally 1% Triton X-100 lysis buffer containing labelled synthetic mouse HPRT mRNA. The cells were lysed and the contents together with the synthetic mRNA present in the lysis buffer were pumped down the channels. The synthetic mRNA hybridised to the oligonucleotide in the area exposed by the channels. The channels were 5 μm wide by 25 μm high.

Thus hybridisation is possible in the presence of lysis buffer and cell lysate. The purification steps used before a conventional microarray hybridisation experiment are thus not required when using the invention, and it is possible to achieve and detect hybridisation in the channels of the device after chemical lysis of the individual cells while both the lysis buffer and the lysate remain present.

In Situ Reverse Transcription

Conventional microarray techniques require mRNA to be purified, reverse-transcribed, amplified, labelled, and purified again before hybridising to probes on the array. In other techniques, purified mRNA is hybridised directly to the array. The duplexed probe, tethered to provide a free 3' end, then acts as a primer for in situ enzymatic extension by reverse transcription [56]. A fluorescently-labelled dNTP is included in the reaction so that the resulting product is a covalently array-bound labelled cDNA copy of the mRNA. Since the extended labelled product is covalently attached to the array through the primer, any unincorporated nucleotides can be removed by simply washing the array, with no subsequent loss in product yield.

This method provides a simple alternative to the more complex purification and labelling of solution-based target preparations, and incorporation of an enzyme step into array-based analysis can improve specificity. The requirement of the enzyme for perfect base-pairing between the template and the primer, particularly at the terminal bases of the extending end of the primer, complements the specificity of the hybridisation reaction alone.

Implementation of the method targets the junction between the poly-A tail and the 3' end of the mRNA-specific sequence. This region is least likely to be affected by secondary structure in the target and steric interference.

Before custom synthesis of microarrays by ink-jet fabrication, several preliminary experiments were performed. Patches of DNA oligonucleotide probe (20×20 mm) were synthesized using an ABI 394 DNA synthesizer onto an epoxy-derivatised glass slide derivatised with polyethylene glycol 200 (15 atoms), equivalent to a length of 2.5 nucleotides. The DNA probe sequence 5'-dT$_{25}$oligo$_{21}$-3' was synthesized in the "reverse" orientation, 5' to 3', to allow primer extension from the free 3'-OH. In an initial experiment a human β-globin polyA$_{15}$ IVT (in vitro transcription, obtained using T7 RNA polymerase) $^{33}$P-labelled mRNA was hybridised to the array, imaged (FIG. 38A), washed and incubated in reverse transcription mix. Removal of the RNA followed by successful hybridisation of a Cy5-labelled probe comprising the 20-mer sequence from the 5' end of the mRNA showed that reverse transcription from the tethered primer extension had gone to completion (FIG. 38B).

Adding a reverse transcription step to a microarray experiment offers advantages over conventional hybridisation. For primer extension to proceed, the enzyme requires near perfect base-pairing at the end of the extending primer. This is a region of the oligonucleotide probe that is known to have relatively small effect on hybridisation, as confirmed in the studies described above. Therefore a target with mismatches at the 3' end of the probe could form a relatively stable hybrid giving rise to a significant level of hybridisation intensity, but is unlikely to be extended by reverse transcriptase. Furthermore, this primer extension method is less likely to produce errors in expression level analyses as a result of errors incorporated during the preparation of a labelled copy of the target. Studies using hybridisation of mRNA populations to a DNA microarray require that the mRNA is copied (and in some cases amplified) and labelled before hybridisation to the array. Copying and amplification are both steps that have the possibility of introducing incorrect bases into the mRNA sequence. For example, a study of RT-PCR using four different reverse transcriptases and DNA polymerase enzymes produced clones in which between 4 and 20% of the clones contained mutated sequences.

Aside from specificity, direct copying of the mRNA in situ on the array simplifies the process for obtaining expression analysis data. A purified poly-adenylated mRNA is hybridised directly to the array. Upon hybridisation the perfectly matched target:probe complexes are extended via reverse transcriptase incorporating a fluorescently labelled dNTP via direct incorporation. The extended, labelled product is covalently attached to the array so that unincorporated nucleotides and any unextended target can be removed from the array by stringent washing. There is no need to copy, amplify or pre-label the mRNA before hybridisation. There is no loss of sample during the purification of the labelled copy.

In further experiments, cells were lysed in situ on a glass slide covered with oligo-dT(30). The lysis buffer contained 320 mM sucrose, 5 mM MgCl$_2$, 10 mM Hepes and 1% Triton-X100. The slide was incubated in lysis buffer for 90 mins at room temp, washed and then incubated in reverse transcriptase mix for 2 hrs at 45° C. using Superscript III enzyme and a red fluorophore.

The results confirmed that mRNA could hybridise to the immobilised oligonucleotides, even in the presence of the lysis buffer and the cell lysate, and also that reverse transcription could take place under these conditions.

Figure 59:
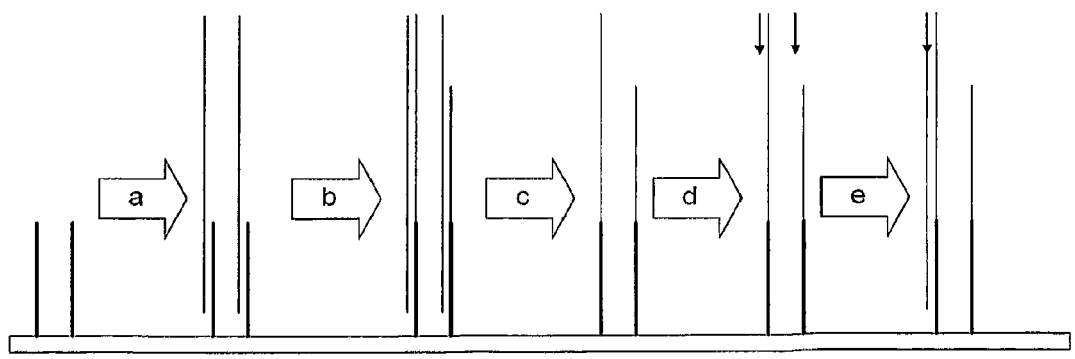
FIG. 59 shows second strand cDNA synthesis after in situ reverse transcription.
Figure 63:
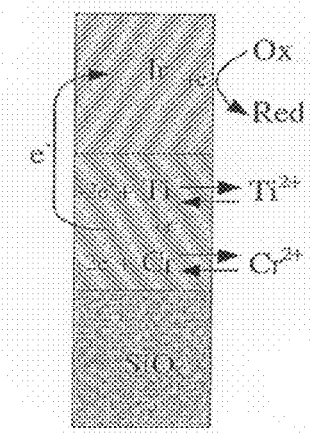
FIG. 63 shows the formation of a galvanic element between the keying layer (Cr or Ti), and the noble electrode material (Ir). Ox can be $O_2$, $I_2$ or $H_2O_2$.

After reverse transcription, which initially gives a mRNA/cDNA hybrid, it is possible to remove the mRNA and synthesise a second strand of cDNA (FIG. 59). FIG. 62 shows the results of an experiment in which second strand synthesis was performed.

An oligo-DNA complementary to bases 800-859 of the mouse HPRT mRNA was immobilised on a NHS-derivatised glass slide. A chamber of fixed shape was used to constrain the oligo-DNA to a specific region of the slide surface. A Cy3-labelled synthetic 1200 base RNA target was hybridised to the slide. Hybridisation took place within the same chamber, but it had been offset slightly in order to determine any non-specific binding of the RNA to the slide. The slide was scanned (FIG. 62A). Hybridisation took place for 1 hour at 37° C. Reverse transcription mix was then applied, with incubation for 1 hour at 50° C. Cy5 label was incorporated into DNA during reverse transcription. The slide was then washed and scanned (FIG. 62B).

The array was then treated under standard RNAse H conditions to remove the Cy3 RNA, was washed and then scanned (Cy3 channel =FIG. 62C; Cy5 channel =FIG. 62D). The RNase treatment removed ~75% of the Cy3 signal.

Two areas of the patch were incubated in a second strand synthesis step. FIG. 62E illustrates how the patch was segregated in this step—one square ('+pol') was incubated with the necessary reagents for DNA synthesis, one square omitted the DNA polymerase ('−pol'), and the surrounding region was not treated. The two squares contained 60 μm dNTPs and 20 μM Cy3-dCTP. The second strand primer was complementary to the extreme 3' end of the fully-extended cDNA sequence. Thus only full-length extension products of reverse transcription would be able to direct second strand synthesis.

FIG. 62F shows that the '+pol' square is brighter in the Cy3 channel than both the '−pol' square and the surrounding regions. Through the Cy5 channel, however, there is no difference in signal (FIG. 62G). Thus there was a significant amount of full length primer extension (800 bases) in the reverse transcription step.

Effect of polyA/polyT Interactions on Hybridisation and Reverse Transcription

Optimal hybridisation on DNA oligonucleotide microarrays is a compromise between specificity and sensitivity; specificity arises from shorter oligonucleotides whilst sensitivity increases with the length of the oligonucleotide. For expression analysis the ideal would be to increase the sensitivity without decreasing the specificity A comparison of the signal intensities of the beta globin IVT with (polyA+) and without (polyA−) the 15 base polyA tail suggested that the poly rA:dT interaction had a very significant effect on hybridisation yield.

A dual-labelling method was employed that allowed simultaneous analysis of both the hybridisation and reverse transcription reactions. The human β-globin IVT was labelled by direct incorporation using CY3-dCTP. The on-array reverse transcript was labelled by direct incorporation of CY5-UTP. A schematic representation of the array based hybridisation and reverse transcription reactions is shown in FIG. 39. An immobilised probe is attached at its 5' end via a linker (91) to a solid support and has a poly-dT region (92) and a target-specific sequence (93) of up to 21 nucleotides. A mRNA target has a poly-A tail (94) at its 3' end and a coding sequence (95). In the test system, Cy3 label (96) is incorporated during transcription for assessing hybridisation (step A). In step B, reverse transcription takes place in the presence of Cy5-labelled dCTP. The extended probe therefore includes Cy5 label (97).

To study the effect of a poly-dT tract which could act both as a spacer and interact with the mRNA tail to "catch" polyadenylated mRNA, $dT_{0-25}$ was added to 5' end of tethered probes in increments of five up to a maximum $dT_{25}$.

Hybridisations to the β-globin IVT target were carried out in either 1 M NaCl/20% formamide buffer or the Superscript II reverse transcription enzyme 1× reaction buffer at 42° C. and 50° C. All hybridisation reactions were set up at room temperature and then incubated at the required temperature for 90 minutes.

1×1 M NaCl hybridisation mix contained: 1×MES*, 1 M NaCl, 20% formamide, 20 mM EDTA (pH 8.0), 0.5 mg/ml BSA, 1% Triton X-100, 140-280 units RNasinT™ Ribonuclease Inhibitor (Promega), 8 nM CY3 labelled IVT target and $H_2O$ to a volume of 250 μl.

1 X Superscript II hybridisation mix contained: 50 mM Tris-HCl, pH 8.3, 75 mM KCl, 3 mM MgCl2, 20 mM DTT, 140-280 units RNasin™ Ribonuclease Inhibitor, 0.5 mg/ml BSA, 8 nM CY3 labelled IVT target and $H_2O$ to a volume of 250 μl.

The mixes were applied to two sections of a hybridisation chamber through a syringe and needle. The array was incubated in a rotating hybridisation oven at 42° C. or 50° C. for 90 minutes. After incubation the slide was removed from the holder and washed. Wash (1) was in 6×SSPE, 0.005% N-lauryl-sarkosine (50 ml at room temperature for five minutes). Wash (2) 0.06×SSPE, 0.18% PEG 200 (50 ml at room temperature for five minutes). The slide was then either dried under compressed air and scanned in an Agilent G2565BA scanner or set up in a reverse transcription reaction.

Reverse transcription of the hybridised target was mostly done post-hybridisation and washing of the slide; in one case hybridisation and reverse transcription were done together in a one step reaction. Superscript II enzyme (Invitrogen) was used in the reactions at 42° C. and Thermoscript (Invitrogen) was used for the higher temperature 60° C. reactions. Reverse transcription reaction using the Superscript II enzyme at 42° C. was set up as follows; the reaction mix contained 50 mM Tris-HCl, pH 8.3, 75 mM KCl, 3 mM $MgCl_2$, 20 mM DTT, 140-280 units RNasin™ Ribonuclease, 100 μM of each dNTP, 8 μM Cy5-dCTP, 0.5 mg/ml BSA, 4000 units Superscript II enzyme and $H_2O$ to a volume of 250 μl. The mixes were applied to the arrays in dual hybridisation chambers at room temperature and then incubated at 42° C. in a rotating oven for two hours. When the hybridisation and reverse transcription were done in a single reaction, IVT RNA target to 8 nM final concentration was added to the reaction mix.

The reaction buffer for the Thermoscript enzyme contained 50 mM Tris acetate (pH 8.4) 75 mM potassium acetate, 8 mM magnesium acetate. All other components of the mix were the same. The reaction mix and the slide were incubated at 60° C. separately for 15 minutes, so that both were up to temperature before the mix was added to the array. The array was incubated for two hours at 60° C. After incubation the slide was removed from the chamber washed in 6×SSPE, 0.005% N-lauryl-sarkosine (50 ml at room temperature for five minutes) and then 0.06×SSPE, 0.18% PEG 200 (50 ml at room temperature for five minutes). The slide was dried under compressed air before scanning.

Figure 40:
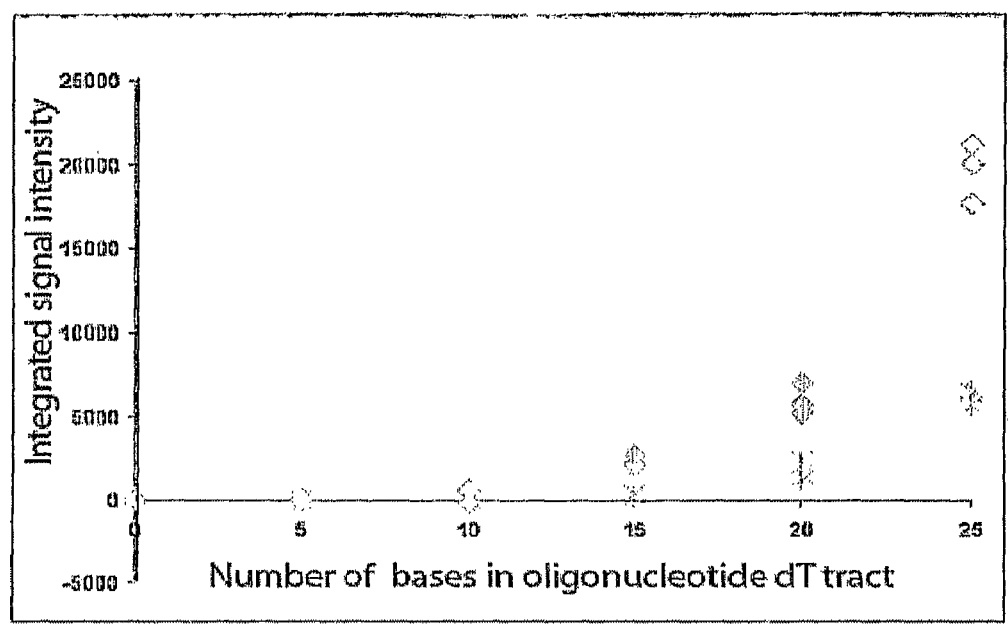
FIGS. 40 & 41 shows the effect of oligo-dT length on hybridisation efficiency.
Figure 40:
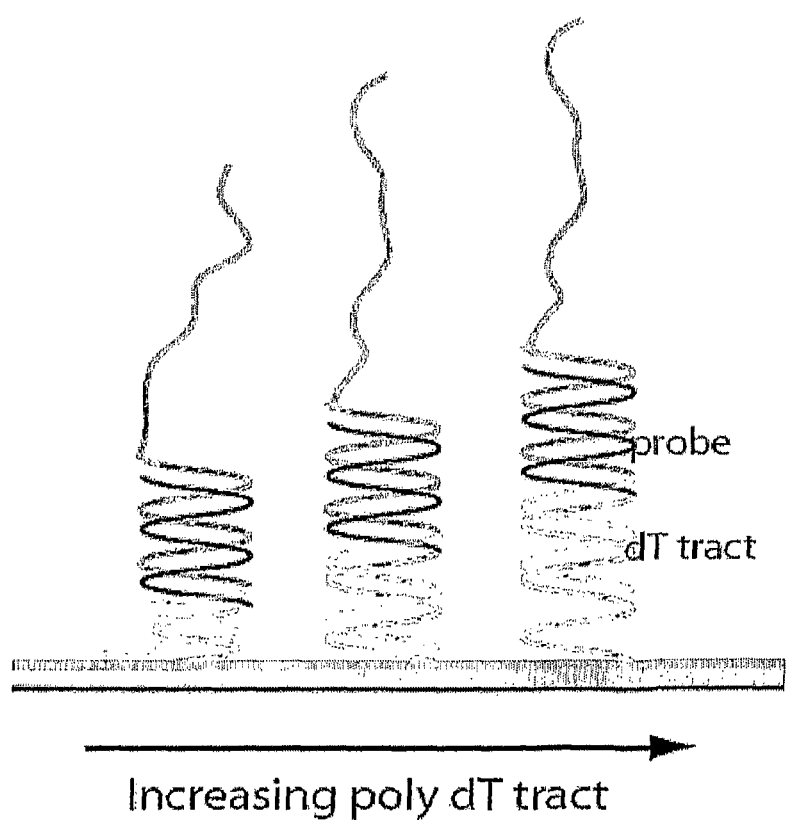

The effect of adding an increasing length of poly-dT spacer between the oligonucleotide probe and solid support is shown in FIG. 40. In both the 1M NaCl/formamide and Superscript buffers, the poly-dT tract gives a four to five fold increase in hybridisation intensity relative to the hexaethylene-glycol linker at equivalent lengths of polymer. The $dT_{15}$ tract is equivalent in length to the maximum HEG5 linker.

By far the greatest effect on hybridisation, ~100-fold over the intensity for the conventional linker, is seen when the poly-dT tract exceeds the length of the 15 base poly-A tail.

With a probe length of 20 bases, a poly $dT_{25}$ sequence, consisting of 15 bases hybridised to the poly-A tail and ten bases of additional 'spacer', the addition of a further spacer of 5 HEG units produced a four fold increase in hybridisation signal. In comparison, addition of five units of HEG onto a $dT_{10}$ tract produces very little increase in hybridisation. This result shows the benefit of adding a long poly-dT spacer to capture poly-A terminated mRNA targets. There is an approximately 300 fold increase in intensity as compared to the conventional linker.

Figure 42:
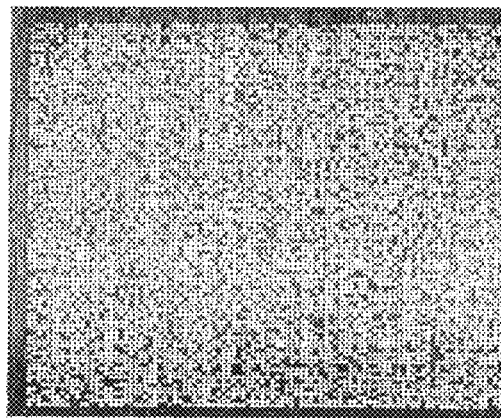
FIG. 42 shows the effect on hybridisation of including a polyA tail in mRNA.
Figure 42:
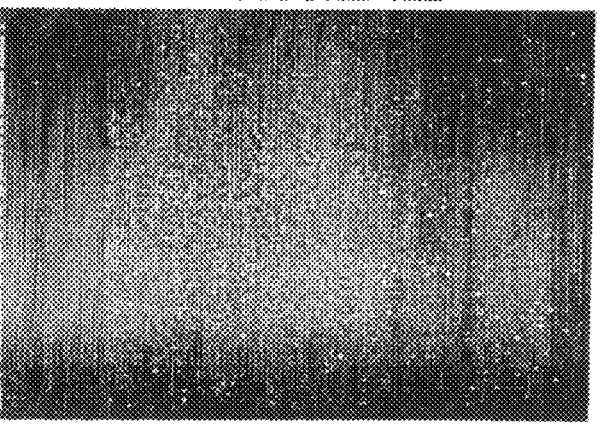

To investigate further the significance and role of the poly-A/poly-dT interaction in the hybridisation process, the hybridisation properties an IVT without the poly-A tail (42B) were compared to those of the IVT with the poly-A tail (42A). The hybridisations were performed on two arrays on the same slide. The Superscript 11 buffer was used as the hybridisation buffer and the hybridisation temperature was 42° C. A scanned image of the arrays is shown in FIG. 42. It is clear that the overall hybridisation is significantly reduced in the absence of the poly-A tail (i.e. in FIG. 42B).

Figure 41:

Comparison between the two targets of the effect on hybridisation yield of an increasing length of poly dT-tract introduced into the 5' end of the 20mer probe on its own and in combination with HEG spacer is shown in FIG. 41. For the polyA– IVT, where the dT sequence is acting simply as a spacer, a relatively small and linear increase in intensity is seen, up to the maximum $dT_{25}$ and is similar in magnitude to that seen for the addition of equivalent numbers of atoms of HEG spacer. The most significant observation was the effect of increasing length of dT on the polyA+ target. At $dT_{15}$ and below, the hybridisation intensity values of the polyA+ target are less than those of the polyA– despite the fact that the dT tract can form duplex with the polyA tail. When the length of dT tract exceeds the length of the polyA tail, a logarithmic increase in hybridisation intensity is observed. The hybridisation intensity of the target with the polyA tail is three fold that of the target without the polyA tail at $dT_{25}$.

Effects of dT tract length on reverse transcript yield were measured and compared to that of hybrid yield. There was little effect on product yield by adding up to five units of a hexaethylene glycol spacer to the oligonucleotide primer. In contrast, there was a significant effect on cDNA product yield by placing a poly $dT_{0-25}$ tract between the solid support and the base oligonucleotide primer. FIG. 43 compares the RT and hybrid yields. In both NaCl/formamide (43A) and Superscript II (43B) buffers the intensity yields of the extended cDNA products are similar to those of the target:probe heteroduplexes. Shorter probes also show the same effect.

Figure 44:
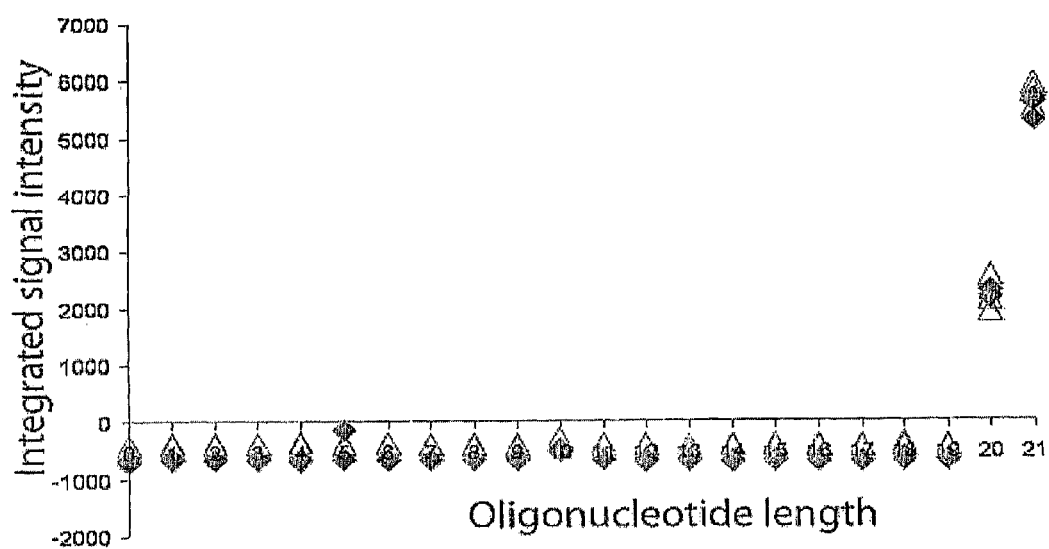

The role of polyA/polyT interaction in the reverse transcription was investigated by a comparison of the product yield from the p-globin IVT with and without the polyA tail. The experiment was carried out in duplicate. One experiment showed significant extension (FIG. 44) The second experiment showed no significant extension from either the 20 of 21 base probes, but both hybridisation and reverse transcription were believed to have failed in the second experiment for an unknown reason.

Figure 45:
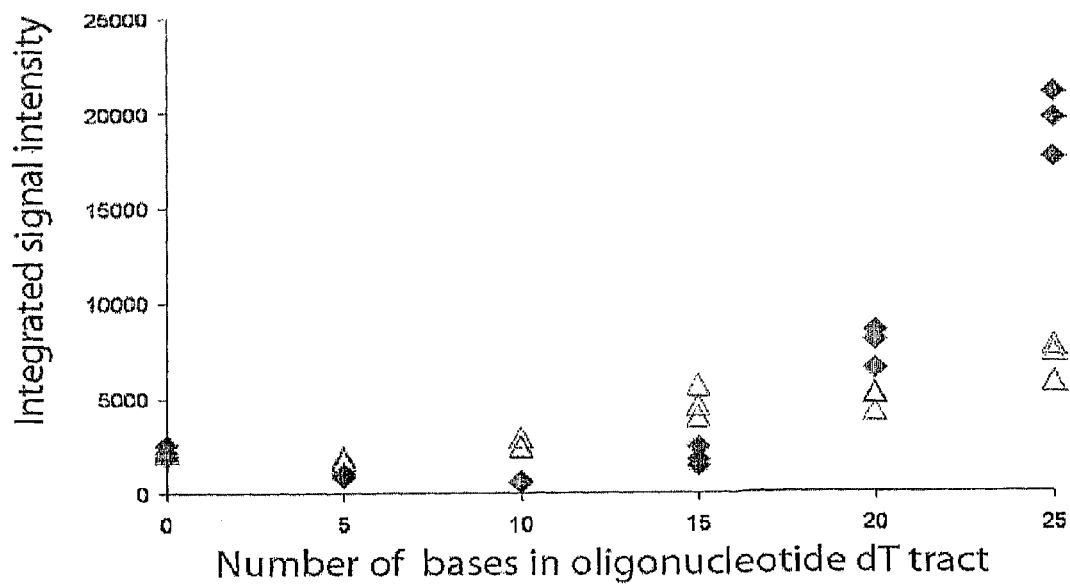

The results of adding an increasing length of poly-dT tract to the oligonucleotide probe is shown by FIG. 45. Between one and five units of $dT_5$ were inserted 5' of the oligonucleotide primer. The results for reverse transcription closely followed what was seen for hybridisation.

Overall, the poly-dT:poly-rA interaction enhances yield by increasing stability of hybrids and/or rate of hybridisation at the expense of reduced specificity. However, including reverse transcription greatly increases specificity and can give near perfect discrimination at high temperatures.

Single Molecule Detection

For sensitive detection of fluorophores, a scanner was operated at a pixel resolution of about 130 nm and a diffraction limited resolution of between 300 nm (using Sparrow's criterion) and 370 nm (using Raleigh's criterion) at a wavelength of 580 nm (Cy3 emission wavelength). Thus the full diffraction limited resolution is usable within the Nyquist criterion. The excitation wavelength was 532 nm. The emitted light was harvested using a cooled 12 bit-per-pixel CCD with commercial dry microscope optics.

Positioning of the sample perpendicular to the optical axis was controlled with a resolution of 100 nm using linear encoders. The micropositioning stages were actively controlled and operated in a closed loop.

Using an excitation density of about $1\ kW/cm^2$, the homogeneous excitation generates (if a single pixel is analysed) about 55 CCD counts per fluorescing dye molecule in the single pixel in the centre of the peak. The excitation time for this result was 100 ms. The noise under identical conditions is about 10 counts per pixel, giving a signal:noise ratio of ~5:1 for the detection of single molecules in a single pixel. As the diffraction limited spots are larger (roughly 9 pixel), the SNR can exceed this value using proper analysis.

Using this scanner, emission could be measured from single dye molecules. FIG. 61 shows an image of a 100×100 pixel area (equivalent to $(13\ \mu m)^2$) captured at a single horizontal sample position using 100 ms exposure time at maximum laser power. Eventually, photobleaching of dye molecules was seen. The small high intensity spots visible in FIG. 61 correspond to single cDNA molecules.

FIG. 73 shows that bleaching did not occur in smooth analog transitions, but was quantised whenever a dye molecule is either bleached or re-emitting. Thus quantising means that molecule counting does not need to rely on spatial discrimination alone, as intensity discrimination can be used as well. Hence, more than one molecule can be counted at a single position.

Forming Oligonucleotide Stripes

As discussed above, various methods can be used to immobilise stripes of oligonucleotides onto a solid support.

Figure 64:
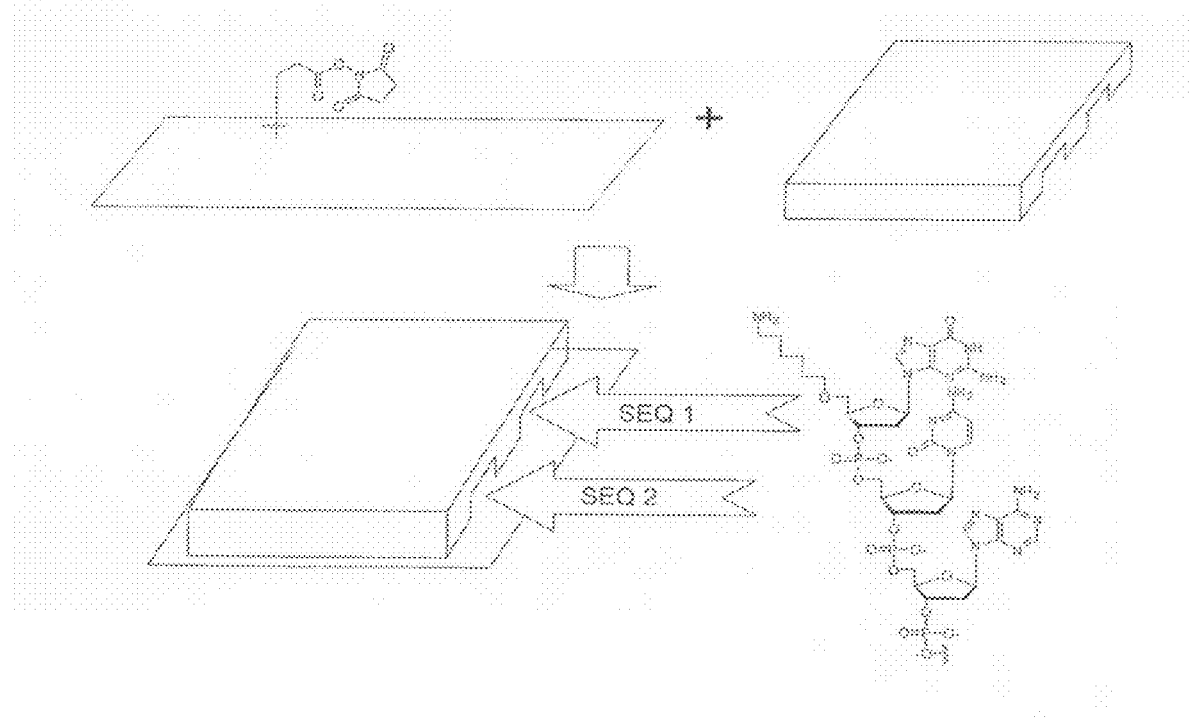
FIGS. 64 and 66 illustrate attachment of pre-synthesised nucleic acids to an activated surface.
Figure 65:
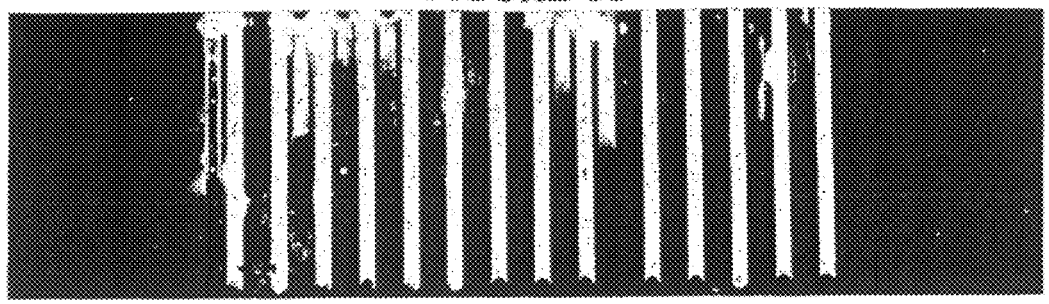

In an embodiment of the method illustrated in FIG. 64, pre-synthesised oligonucleotides have been covalently attached to NHS-coated glass slides. A 3'—$NH_2$—C7 modified 16mer labelled at the 5' end with Cy5 was passed down channels over the surface of the slides. The oligonucleotides were used at various concentrations in the range 0.1-10 µM oligonucleotides, in 0.2 M phosphate buffer at pH 9.0/ DMSO. FIG. 65 shows a fluorescent image of the resulting slide, confirming efficacy of this attachment method.

Figure 66:
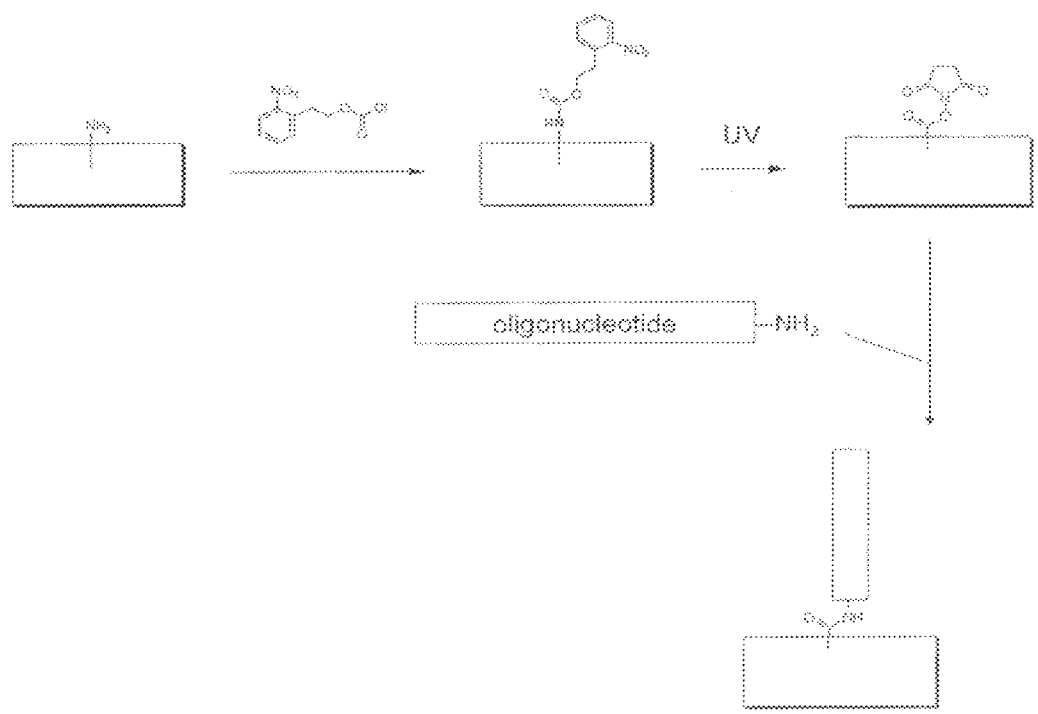
Figure 67:
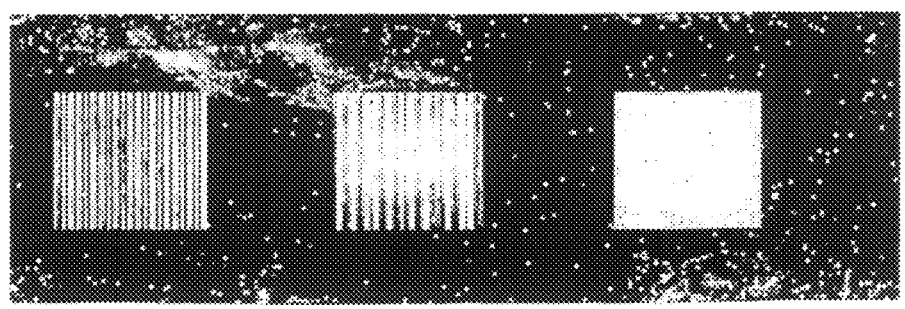
FIGS. 67 and 68 shows fluorescence of nucleic acids attached by the FIG. 66 method.
Figure 68:
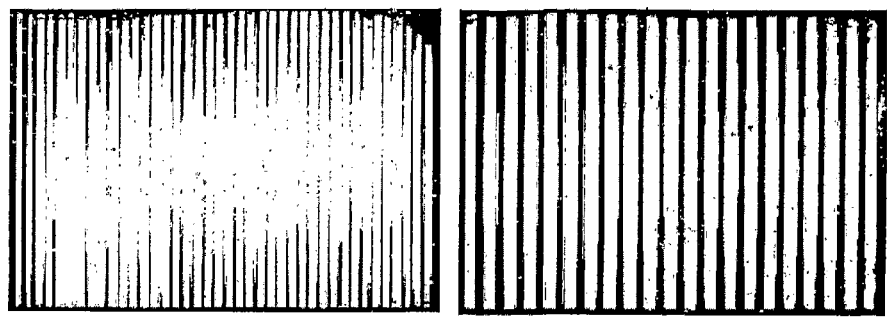

A method using photocleavable protecting groups is shown in FIG. 66. An amino-coated surface is derivatised as shown. The resulting photosensitive surface is exposed to UV light an appropriate mask, removing the photolabile protecting group and exposing stripes of reactive NHS-ester groups. The surface is then exposed to a suitable amino-modified oligonucleotide for covalent coupling to the surface. The fluorescent-labelled probes used in FIG. 65 were also used in this technique, with three different widths of UV stripes being used for deprotection, and the results are shown in FIG. 67. A complementary Cy3-labelled oligonucleotide was used to confirm the orientation of the immobilised oligonucleotide and its availability for hybridisation. Results are in FIG. 68.

A similar method can be performed using acid-labile protecting groups, with stripes of acid being generated using the electrochemical methods of references 32 to 34 and 49.

Computer Modelling

A computer model was prepared for a target flowing through a channel of width 80 μm over a probe patch of length and width 40×80 μm, at a range of channel heights and flow rates. A diffusion coefficient of 19 μm²/s was used, corresponding to a target length of 250 bp. An infinite on rate constant was used for target-probe hybridization, with a zero off rate constant, so that all target which reaches the probe surface hybridizes immediately and remains there.

According to the model, if mRNA molecules flow past a patch 80 μm in length in a channel of height 1-5 μm at a flow rate of 12.5 μm/s, more than 99% of molecules will be taken up. Whether the molecules migrate under piston flow (electrophoresis) or by laminar flow (mass transport of the solution), there is little difference in the proportion captured.

This flow rate can be achieved by electrophoresis at around 2 V/cm. At this flow rate, it would take around 800 secs to traverse a channel 1 cm in length, passing ~100-200 probes. For a target flowing through a channel of width 80 μm over a probe of width 80 μm and of lengths 10, 20 and 40 μm at a range of channel heights and flow rates, using a uniform velocity profile (piston flow) and a diffusion coefficient of 19 μm²/s, the model indicates that ≧95% hybridisation can readily be achieved.

It will be understood that the invention has been described by way of example only and modification of detail may be made without departing from the spirit and scope of the invention.

References (the full contents of which are incorporated herein by reference)

[1] Cossman et al. (1999) *Blood* 94:411-16.
[2] Krylov et al. (1999) *Cytometry* 37:14-20.
[3] Bao & Suresh (2003) *Nature Materials* 2:715-725.
[4] Andersson & van den Berg (2004) *Curr Opin Biotechnol* 15:44-49.
[5] U.S. Pat. No. 6,524,456.
[6] U.S. Pat. No. 6,538,810.
[7] Wu et al. (2004) *PNAS USA* 101:12809-13.
[8] Fu et al. (2002) *Analytical Chem* 74:2451-7.
[9] Munce et al. (2004) *Anal. Chem.* 76:4983-9.
[10] Khine et al. (2005) *Lab on a chip* 5. 'A single cell electroporation chip'.
[11] Braff et al. (2002) Microsystems Technology Laboratories, MIT, *Annual Report May* 2002. 'Microfabricated Cell Analysis Device'.
[12] WO01/35071. Also U.S. Pat. No. 6,692,952.
[13] Cheung et al. (2002) pages 71-75 of *2nd Annual International IEEE-EMBS Special Topic Conference on Microtechnologies in Medicine and Biology*.
[14] Kitagawa et al. (1995) *Electrophoresis* 16:1364-8.
[15] Di Carlo et al. (2003) *Lab on a Chip* 3:287-291.
[16] Przekwas et al. (2001) pages 214-217 of *Modeling and Simulation of Microsystems*. ISBN 0-9708275-O-4.
[17] U.S. Pat. No. 6,156,576.
[18] Sims et al. (1998) *Anal Chem* 70:4570-7.
[19] US 2002/0142323.
[20] Prinz et al. (2002) *Lab Chip* 2:207-12.
[21] Leffhalm et al. (2005) *AKB* 200.15 *Di* 17.00 *Poster TU C.* Berlin 2005, "Physik seit Einstein", Deutsche Physikalische Gesellschaft.
[22] Lu et al. (2002) Microsystems Technology Laboratories, MIT, Annual Report May 2002. 'Microfabricated Fluidic Devices for Cell Lysis and Subcellular Component Separations'.
[23] Lu et al. (2001) pages 297-8 of *Micro Total Analysis Systems*. Eds. Ramsey et al.
[24] U.S. Pat. No. 6,846,306.
[25] Tsong (1991) *Biophys. J.* 60:297-306.
[26] Lettieri & de Rooij (2003) *Centre Suisse d'Electronique et de Microtechnique (CSEM) Scientific and Technical Report* 2003, page 83.
[27] Lee et al. (2004) *J. Micromech. Microeng.* 14:1390-1398.
[28] Lee et al. (2005) *J. Micromech. Microeng.* 15:1215-1223.
[29] Utz et al. (2005) *Immunol Rev* 204:264-82.
[30] Gershon (2003) *Nature* 424:581-7.
[31] Le et al. (2005) *Front Biosci* 10:1654-60.
[32] WO93/22480.
[33] WO03/020415.
[34] WO2005/037425.
[35] WO2004/033629.
[36] Nie et al (1994) *Science* 266:1018-21.
[37] Schmidt et al. (1996) *Proc. Natl. Acad. Sci. USA* 93:2926-9.
[38] Hesse et al. (2004) *Anal Chem* 76:5960-4.
[39] WO00/25113. See also US-2002/0030811.
[40] Yin et al. (2005) *Anal Chem* 77:527-33.
[41] Wong et al. (2004) *IEEE/ASME Transact Mechatron* 9:366-76.
[42] Hou-Pu et al. (1999) *Proc. Natl. Acad. Sci. USA* 96:11-13.
[43] Chiou et al. (2005) *Nature* 436:370-2.
[44] Dai et al. (2002) *Nucl Acids Res* 30:e86
[45] U.S. Pat. No. 6,420,105.
[46] WO2005/043154.
[47] Koglin et al. (2003) *J. Med. Chem.* 46:4369ff.
[48] Yin et al. (2004) *Nucleic Acids Res* 32(14):e118.
[49] Egeland & Southern (2005) *Nucleic Acids Res* 33:e125.
[50] WO03/000433
[51] Yershov et al., (1996) *Proc Natl Acad Sci USA* 93:4913-8.
[52] Roche Molecular Biochemicals (1998) *Biochemica* number 3, pages 12-14.
[53] U.S. Pat. No. 6,406,891.
[54] Bohl et al. (2005) *J. Micromech. Microeng.* 15 1125-30.
[55] Duffy et al. (1998) *Anal. Chem.* 70:4974-84.
[56] Beier & Hoheisel (2002) *J Biotechnol* 94:15-22.

The invention claimed is:

1. A device for individually analysing cells of interest, comprising:

a plurality of channels, each of which is for receiving the contents of a cell of interest, wherein each channel has an input end and an output end; and a cell trapping site in proximity to the input end of each channel, wherein:

the cell trapping site of each channel is arranged to allow a single cell of interest to be individually trapped;

the input end of each channel is adapted such that an intact cell of interest cannot enter the channel;

each channel contains a sequence of analytical component(s) arranged in discrete patches along the channel for analysing the contents of the cell of interest;

the discrete patches of analytical components are discrete patches of immobilised binding reagents; and the contents of the cell of interest can be moved along the channels, in a direction from the input end towards the output end, and wherein:

(i) the cross-sectional area and/or the cross-sectional shape of each channel; and (ii) the dimensions and arrangement of the patches of immobilised binding reagents along each channel, are configured to permit analysis of the contents of a single cell.

2. The device of claim 1, wherein the channels are substantially identical to each other such that, during use, cells in different channels are separately subjected to substantially the same treatment and analysis as each other.

3. The device of claim 2, wherein the sequence of analytical components in one channel is the same as in another channel.

4. The device of claim 1, wherein the channels are substantially parallel to each other.

5. The device of claim 4, wherein the channels are arranged next to each other within a single plane.

6. The device of claim 1, wherein the channel(s) have a substantially constant cross-sectional area and/or a substantially constant cross-sectional shape.

7. The device of claim 1, wherein the channel(s) have a rectangular cross-sectional shape.

8. The device of claim 1, wherein the channel(s) have a height <50 μm.

9. The device of claim 1, wherein the channel(s) are closed except in the direction of flow from input end to output end.

10. The device of claim 1, wherein the cell trapping site(s) is/are in the form of a tapered inlet before the input end of a channel.

11. The device of claim 10, wherein a cell can be moved into the tapered inlet by the use of electrokinesis.

12. The device of claim 1, wherein a channel includes an expansion chamber either (i) between its cell trapping site and its input end or (ii) immediately downstream of its input end.

13. The device of claim 1, wherein a channel comprises a polydimethylsiloxane wall.

14. The device of claim 1, wherein a channel comprises a glass wall.

15. The device of claim 14, wherein a channel is formed from polydimethylsiloxane mounted on a flat glass support.

16. The device of claim 1, wherein the analytical component(s) are covalently immobilised.

17. The device of claim 1, wherein the binding reagents include nucleic acids for hybridisation.

18. The device of claim 17, wherein the nucleic acids can retain mRNA transcripts.

19. The device of claim 17, wherein the nucleic acids are DNA.

20. The device of claim 17, wherein the nucleic acids are <200 nt.

21. The device of claim 1, wherein the binding reagents include immobilised proteins.

22. The device of claim 1, wherein the binding reagents include immobilised antibodies.

23. The device of claim 1, wherein the analytical reagent(s) are immobilised along only one side of a channel.

24. The device of claim 1, comprising at least 100 different analytical reagents per channel.

25. The device of claim 1, wherein different immobilised binding reagents are arranged in discrete patches.

26. The device of claim 25, wherein each patch of immobilised reagent has an area of less than $10^{-8}$ m$^2$.

27. The device of claim 25, wherein the centre-to-centre separation of adjacent patches is preferably less than $10^{-3}$ m.

28. The device of claim 25, wherein the patches have a rectangular shape.

29. The device of claim 25, wherein the patches are arranged singly in series along a channel's length from input end to output end.

30. The device of claim 25, wherein the patches occupy the full width of a channel.

31. The device of claim 1, comprising a plurality of channels and a plurality of immobilised analysis reagents, wherein the channels intersect lines of immobilised analysis reagents.

32. The device of claim 31, wherein the channels are straight and are substantially parallel to each other.

33. The device of claim 31, wherein the lines of immobilised analysis reagents are straight and are substantially parallel to each other.

34. The device of claim 31, wherein the lines of immobilised analysis reagents run substantially orthogonal to the channels.

35. The device of claim 1, including a delivery line in communication with the cell trapping site(s).

36. The device of claim 35, wherein the delivery line runs perpendicular to the channel(s).

37. The device of claim 35, wherein the delivery line runs parallel to the channel(s).

38. The device of claim 1, including a reagent supply line in communication with the cell trapping site(s).

39. The device of claim 35, wherein the delivery line is taller than the channels.

40. The device of claim 1, including an exhaust in communication with the output end(s) of the analysis channel(s).

41. The device of claim 1, including a pump for moving liquids through the channel(s).

42. The device of claim 1, including one or more electrodes, or connectors for attachment of electrodes.

43. The device of claim 42, wherein the electrodes can be used to generate an electrical potential along a channel.

44. The device of claim 1, including a light source.

45. The device of claim 1, including a camera.

46. The device of claim 18, wherein the nucleic acids comprise immobilised poly-T nucleic acids.

47. The device of claim 19, wherein the nucleic acids comprise immobilised poly-T nucleic acids.

48. The device of claim 20, wherein the nucleic acids comprise immobilised poly-T nucleic acids.

49. The device of claim 38, wherein the reagent supply line is taller than the channels.

50. A process for making the device of claim 1, wherein the channels are formed within a polymeric material.

51. The process of claim 50, wherein the polymeric material is photopolymerisable.

52. The process of claim 50, wherein the channels are formed by casting or injection molding of the polymeric material.

53. The process of claim 50, wherein the polymeric material is PDMS.

54. The process of claim 50, wherein the analytical component(s) is/are immobilised nucleic acids for hybridisation.

55. The process of claim 54, wherein the nucleic acids are attached to a surface of the device using an in situ synthesis method.

56. The process of claim 54, wherein the nucleic acids are synthesised before being attached to a surface of the device.

57. The process of claim 55, wherein the nucleic acids are applied to a surface of the device by forming a contact between a reaction surface on a reaction substrate and an open microfluidic channel on a microfluidic channel substrate; (b) introducing a reagent into the microfluidic channel such that the reagent contacts the reaction surface along a contact line formed by the contact between the reaction surface and the open microfluidic channel; and (c) separating the reaction surface and the microfluidic channel, leaving the reagent immobilised along the contact line on the reaction surface.

58. The process of claim 55, wherein the nucleic acids are applied to a surface of the device by deprotecting a region on the surface of a substrate to expose a reactive group, and applying pre-synthesised nucleic acids to the substrate to allow them to bind to the exposed reactive groups.

59. The process of claim 58, wherein the deprotection is photo-deprotection.

60. The process of claim 58, wherein the deprotection is electrochemical deprotection.

61. A process for individually analysing cells of interest, comprising the steps of:
  individually trapping a cell at a cell trapping site in proximity to the input end of a channel that has an input end and an output end, wherein the cell trapping site is arranged to allow a single cell of interest to be individually trapped, and the input end is adapted such that the cell of interest cannot enter the channel intact;
  releasing the cell's contents such that they enter the input end of the channel;
  allowing the released contents to move from the input end towards the output end, such that they interact with one or more analytical component(s) within the channel,
  thereby permitting analysis of the contents; said process using a device comprising
  a plurality of channels, each of which is for receiving the contents of a cell of interest, wherein each channel has an input end and an output end; and
  a cell trapping site in proximity to the input end of each channel,
wherein:
  the cell trapping site of each channel is arranged to allow a single cell of interest to be individually trapped;
  the input end of each channel is adapted such that an intact cell of interest cannot enter the channel;
  each channel contains a sequence of analytical component(s) arranged in discrete patches along the channel for analysing the contents of the cell of interest;
  the discrete patches of analytical components are discrete patches of immobilised binding reagents; and
  the contents of the cell of interest can be moved along the channels, in a direction from the input end towards the output end,
and wherein:
  (i) the cross-sectional area and/or the cross-sectional shape of each channel; and
  (ii) the dimensions and arrangement of the patches of immobilised binding reagents along each channel,
are configured to permit analysis of the contents of a single cell.

62. The process of claim 61, wherein the contents of a cell are moved along the channel by electrokinesis.

63. The process of claim 61, wherein the contents of a cell are moved along the channel by pumping.

64. The process of claim 61, wherein the analytical component(s) can capture mRNA from a cell by nucleic acid hybridisation.

65. The process of claim 64, wherein mRNA captured by analytical component(s) are reverse transcribed.

66. The process of claim 65, wherein analysis comprises the steps of (i) permitting the mRNA to hybridise to immobilised nucleic acids in a channel, such that the mRNA has a single stranded overhang in the hybrid; (ii) extending the immobilised nucleic acid in the hybrid using the single stranded overhang as a template, wherein the extension reaction incorporates a detectable label into the immobilised nucleic acid.

67. The process of claim 66, wherein analysis further comprises: (iii) melting the hybrid and allowing the free nucleic acid to re-anneal to an immobilised nucleic acid, to form a new hybrid in which the free nucleic acid has a single stranded overhang; and (iv) repeating step (ii) at least n times, where n is an integer >1, provided that where n>1 then step (iii) is performed after at least the first n−1 repeats of step (ii).

68. The process of claim 64, wherein a DNA/mRNA hybrid is detected using an apparatus that can identify single fluorophores.

69. The process of claim 64, wherein at least 80% of the mRNA targets within a cell are captured for analysis.

70. The process of claim 64, wherein the analytical component is an immobilised poly-T nucleic acid.

71. The process of claim 70, wherein mRNA captured by analytical component(s) are reverse transcribed.

72. The process of claim 65, wherein the reverse transcription reaction incorporates labelled nucleotides.

73. The process of claim 66, wherein the reverse transcription reaction incorporates labelled nucleotides.

74. The process of claim 67, wherein the reverse transcription reaction incorporates labelled nucleotides.

75. The process of claim 72, wherein the reverse transcription uses dNTPs labelled with fluorophores.

76. The process of claim 73, wherein the reverse transcription uses dNTPs labelled with fluorophores.

77. The process of claim 74, wherein the reverse transcription uses dNTPs labelled with fluorophores.

78. The process of claim 75, wherein the 1, 2, 3 or 4 of dATP, dCTP, dGTP and dTTP are labelled.

79. The process of claim 76, wherein the 1, 2, 3 or 4 of dATP, dCTP, dGTP and dTTP are labelled.

80. The process of claim 77, wherein the 1, 2, 3 or 4 of dATP, dCTP, dGTP and dTTP are labelled.

81. The process of claim 65 wherein, after reverse transcription has formed a RNA/DNA hybrid, the RNA strand in the hybrid is removed to leave a single-stranded cDNA prepared by extension of an immobilised primer.

82. The process of claim 71 wherein, after reverse transcription has formed a RNA/DNA hybrid, the RNA strand in the hybrid is removed to leave a single-stranded cDNA prepared by extension of an immobilised primer.

83. The process of claim 81, wherein the single-stranded cDNA is used as the template for synthesis of a complementary cDNA strand (second strand) using a primer that is complementary to the existing cDNA strand.

84. The process of claim 82, wherein the single-stranded cDNA is used as the template for synthesis of a complementary cDNA strand (second strand) using a primer that is complementary to the existing cDNA strand.

85. The process of claim 81, wherein the second cDNA strand is synthesised to incorporate label.

86. The process of claim 82, wherein the second cDNA strand is synthesised to incorporate label.

87. The process of claim 65, wherein a captured nucleic acid is sequenced.

88. The process of claim 71, wherein a captured nucleic acid is sequenced.

* * * * *